US009790524B2

(12) United States Patent
Srivastava et al.

(10) Patent No.: US 9,790,524 B2
(45) Date of Patent: Oct. 17, 2017

(54) DESIGNER CELLS FOR ENANTIOSELECTIVE REDUCTION OF KETONES AND USE THEREOF IN EFFICIENT PRODUCTION OF ENANTIOENRICHED ALCOHOLS

(71) Applicant: Council of Scientific & Industrial Research, New Delhi (IN)

(72) Inventors: Gautam Srivastava, Chandigarh (IN); Suneet Kaur, Chandigarh (IN); Ravinder Singh Jolly, Chandigarh (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 0 days.

(21) Appl. No.: 14/785,286

(22) PCT Filed: Apr. 17, 2014

(86) PCT No.: PCT/IN2014/000247
§ 371 (c)(1),
(2) Date: Oct. 16, 2015

(87) PCT Pub. No.: WO2014/170917
PCT Pub. Date: Oct. 23, 2014

(65) Prior Publication Data
US 2016/0289713 A1    Oct. 6, 2016

(30) Foreign Application Priority Data
Apr. 17, 2013 (IN) .......................... 1146/DEL/2013

(51) Int. Cl.
*C12N 9/04* (2006.01)
*C12N 1/20* (2006.01)
*C12N 15/00* (2006.01)
*C12P 7/04* (2006.01)
*C12P 7/62* (2006.01)
*C12P 41/00* (2006.01)
*C12P 7/22* (2006.01)
*C12P 13/00* (2006.01)

(52) U.S. Cl.
CPC .............. *C12P 7/62* (2013.01); *C12N 9/0006* (2013.01); *C12P 7/22* (2013.01); *C12P 13/008* (2013.01); *C12P 41/002* (2013.01); *C12Y 101/01184* (2013.01); *C12Y 101/01047* (2013.01)

(58) Field of Classification Search
CPC ...... C12P 7/00; C12P 7/22; C12P 7/12; C12N 9/0006; C12Y 101/01047
USPC ........ 435/252.2, 257.2, 320.1, 189.146, 147, 435/157
See application file for complete search history.

(56) References Cited

U.S. PATENT DOCUMENTS

| 4,710,468 A | 12/1987 | Sih |
| 4,933,282 A | 6/1990 | Hasegawa et al. |
| 5,413,921 A | 5/1995 | Onishi et al. |
| 5,559,030 A | 9/1996 | Matsuyama et al. |
| 5,700,670 A | 12/1997 | Yamagishi et al. |
| 7,816,111 B2 | 10/2010 | Davis et al. |
| 7,897,366 B2 | 3/2011 | Lee et al. |
| 2007/0254368 A1 | 11/2007 | Lee et al. |
| 2009/0004720 A1 | 1/2009 | Hua et al. |
| 2010/0028972 A1 | 2/2010 | Davis et al. |

FOREIGN PATENT DOCUMENTS

| WO | WO 2005/017135 | 2/2005 |
| WO | WO 2010/151593 | 12/2010 |

OTHER PUBLICATIONS

Aoki, T., et al., "GFP-Display", an easy detection method for single amino acid changes in a target polypeptide: Application to random mutagenesis. *Analytical Biochemistry* 2002, 300, 103-106.
Bae, w., et al., Enhanced bioaccumulation of heavy metals by bacterial cells displaying synthetic phytochelatins. *Biotecnhology and Bioengineering* 2000, 70, 518-524.
Bae, w., et al., Cell surface display of synthetic phytochelatins using ice nucleation protein for enhanced heavy metal bioaccumulation. *J Inorg Biochem* 2002, 88, 223-227.
Chao, G., et al., Isolating and engineering human antibodies using yeast surface display. *Nat. Protocols* 2006, 1, 755-768.
Dhillon, J.K., et al., Bacterial surface display of an anti-pollutant antibody fragment. *Lett Appl Microbiol* 1999, 28, 350-354.
He, J.-Y., et al., Biocatalytic synthesis of ethyl (S)-4-chloro-3-hydroxy-butanoate in an aqueous-organic solvent biphasic system using Aureobasidium pullulans CGMCC 1244. *Process Biochemistry* 2006, 41, 244-249.
Kaliaperumal, T., et al., Asymmetric synthesis of (S)-4-chloro-3-hydroxybutanoate using *andida parapsilosis* ATCC 7330. *J Ind Microbiol Biotechnol* 2010, 37, 159-165.
Kaluzna, I. A., et al., Systematic investigation of *Saccharomyces cerevisiae* enzymes catalyzing carbonyl reductions. *J Am Chem Soc*, 2004, 126, 12827-12832.
Kataoka, M., et al., Gene cloning of an NADPH-dependent menadione reductase from Candida macedoniensis, and its application to chiral alcohol production. *Enzyme and Microbial Technology* 2006, 38, 944-951.
Kita, K., et al., Purification and characterization of new aldehyde reductases from *Sporobolomyces salmonicolor* AKU4429. *Journal of Molecular Catalysis B: Enzymatic* 1999, 6, 305-313.

(Continued)

*Primary Examiner* — Tekchand Saidha
*Assistant Examiner* — Md. Younus Meah
(74) *Attorney, Agent, or Firm* — Workman Nydegger

(57) ABSTRACT

The present invention is to provide a preparation of variant recombinant whole cell biocatalysts, referred herein as "designer cells" having significantly enhanced carbonyl reductase activity for use in the efficient production of variant industrially important enantiomerically enriched alcohols. More specifically, the alcohol is optically pure ethyl (S)-4-chloro-3-hydroxybutyrate, which is useful as chiral building block and an intermediate for the production of hydroxymethylglutaryl-CoA (HMG-CoA) reductase inhibitors.

17 Claims, 6 Drawing Sheets

(56) References Cited

OTHER PUBLICATIONS

Kizaki, N., et al., Synthesis of optically pure ethyl (S)-4-chloro-3-hydroxybutanoate by *Escherichia coli* transformant cells coexpressing the carbonyl reductase and glucose dehydrogenase genes. *Applied Microbiology and Biotechnology* 2001, 55, 590-595.

Lee, S., et al., Microbial cell-surface display. *Trends in Biotechnology* 2003, 21, 45-52.

Ma, S.K., et al., A green-by-design biocatalytic process for atorvastatin intermediate. *Green Chemistry* 2010, 12, 81-86.

Saratani, Y., et al., Stereoselective reduction of ethyl 4-chloro-3-oxobutanoate by fungi. *Biosci Biotechnol Biochem* 2001, 65, 1676-1679.

Shibasaki, S. S., et al., Creation of cell surface-engineered yeast that display different fluorescent proteins in response to the glucose concentration. *Applied Microbiology and Biotechnology* 2001, 57, 528-533.

Shibasaki, S., et al., Intelligent yeast strains with the ability to self-monitor the concentrations of intra- and extracellular phosphate or ammonium ion by emission of fluorescence from the cell surface. *Applied Microbiology and Biotechnology* 2001, 57, 702-707.

Shimazu, M., et al., Cell Surface Display of Organophosphorus Hydrolase Using Ice Nucleation Protein. *Biotechnology Progress* 2001, 17, 76-80.

Shimazu, M., et al., Simultaneous degradation of organophosphorus pesticides and p-nitrophenol by a genetically engineered *Moraxella* sp. with surface-expressed organophosphorus hydrolase. *Biotechnology and Bioengineering* 2001, 76, 318-324.

Sousa, C., et al., Metalloadsorption by *Escherichia coli* cells displaying yeast and mammalian metallothioneins anchored to the outer membrane protein LamB. *Journal of Bacteriology* 1998, 180, 2280-2284.

Sundby, E., et al., The enantioselectivity of reduction of ethyl 4-halo-3-oxobutanoate catalyzed byGeotrichum candidum depends on the cofactor. *Journal of Molecular Catalysis B: Enzymatic* 2003, 21, 63-66.

Wada, M., et al., Purification and characterization of NADPH-dependent carbonyl reductase, involved in stereoselective reduction of ethyl 4-chloro-3-oxobutanoate from *Candida magnoliae*. *Biosci Biotechnol Biochem* 1998, 62, 280-285.

Wang, L. J., et al., ighly efficient synthesis of chiral alcohols with a novel NADH-dependent reductase from *Streptomyces coelicolor*. *Bioresource Technology* 2011, 102, 7023-7028.

Xu, Z., et al., Display of polyhistidine peptides on the *Escherichia coli* cell surface by using outer membrane protein C as an anchoring motif. *Appl Environ Microbiol* 1999, 65, 5142-5147.

Xu, Z., et al., Construction of a two-strain system for asymmetric reduction of ethyl 4-chloro-3-oxobutanoate to (S)-4-chloro-3-hydroxybutanoate ethyl ester. *Applied Microbiology and Biotechnology* 2006, 70, 40-46.

Yamamoto, H., et al., Purification and properties of a carbonyl reductase useful for production of ethyl (S)-4-chloro-3-hydroxybutanoate from *Kluyveromyces lactis*. *Biosci Biotechnol Biochem* 2002, 66, 1775-1778.

Yamamoto, H., et al., A novel NADH-dependent carbonyl reductase from *Kluyveromyces aestuarii* and comparison of NADH-regeneration system for the synthesis of ethyl (S)-4-chloro-3-hydroxybutanoate. *Biosci Biotechnol Biochem* 2004, 68, 638-649.

Yasohara, Y., et al. Synthesis of optically active ethyl 4-chloro-3-hydroxybutanoate by microbial reduction. *Applied Microbiology and Biotechnology* 1999, 51, 847-851.

Yasohara, Y., et al. Molecular cloning and overexpression of the gene encoding an NADPH-dependent carbonyl reductase from *Candida magnoliae*, involved in stereoselective reduction of ethyl 4-chloro-3-oxobutanoate. *Biosci Biotechnol Biochem* 2000, 64, 1430-1436.

Ye, Q., et al., Construction and co-expression of a polycistronic plasmid encoding carbonyl reductase and glucose dehydrogenase for production of ethyl (S)-4-chloro-3-hydroxybutanoate. *Bioresource Technology* 2010, 101, 6761-6767.

Ye, Q., et al., A novel carbonyl reductase from *Pichia stipitis* for the production of ethyl (S)-4-chloro-3-hydroxybutanoate. *Biotechnol Lett* 2009, 31, 537-542.

Ye, Q., et al., A new member of the short-chain dehydrogenases/reductases superfamily: purification, characterization and substrate specificity of a recombinant carbonyl reductase from *Pichia stipitis*. *Bioresource Technology* 2009, 100, 6022-6027.

Zhang, J., et al., Coupling of permeabilized microorganisms for efficient enantioselective reduction of ketone with cofactor recycling. *Chemical Communications* 2006, 398-400.

Zhu, D., et al., Stereoselective enzymatic synthesis of chiral alcohols with the use of a carbonyl reductase from *Candida magnoliae* with anti-Prelog enantioselectivity. *The Journal of Organic Chemistry* 2006, 71, 4202-4205.

Sambrook, J., Russell, D. W., Molecular Cloning: A Laboratory Manual. Cold Spring Harbor Laboratory Press.1989; vol. 2., Chapters 1, 6, 7, 12-16, and Index.

Yuning Su; et al. "Two-Enzyme Coexpressed Recombinant Strain for Asymmetric Synthesis of Ethyl (R)-2-Hydroxy-4-phenylbutyrate" Chinese Journal of Catalysis, Sep. 1, 2012 Elsevier—ISSN 1872-2067; vol. 33, Nr:9-10, pp. 1650-1660; Sep. 1, 2012 (Sep. 1, 2012);http://dx.doi.org/10.1016/S1872-2067(11)60436-1.

Ye Ni, et al. "Scalable biocatalytic synthesis of optically pure ethyl ®-2-hydroxy-4-phenylbutyrate using a recombinant *E. coli* with high catalyst yield"; Journal of Biotechnology, pp. 493-497 (Jul. 19, 2013).

Depository Certificates, Institute of Microbial Technology; Mar. 13, 2013.

PCT/IN2014/000247, Oct. 7, 2014, International Search Report and Written Opinion.

PCT/IN2014/000247, May 6, 2015, International Preliminary Report on Patentability.

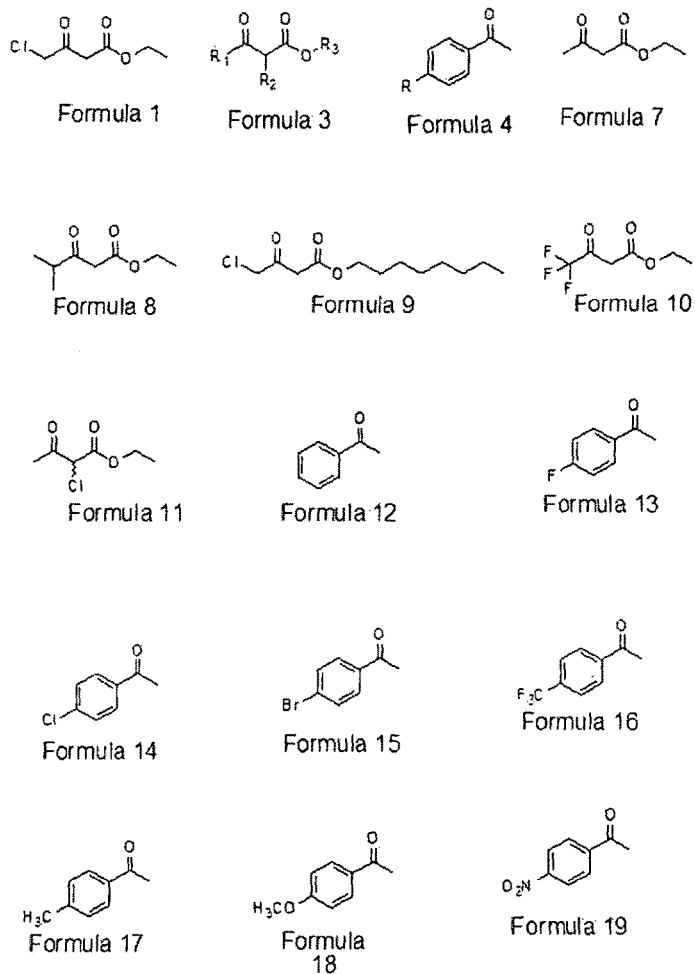
Figure 1: Examples of aliphatic and aromatic compounds serving as substrates

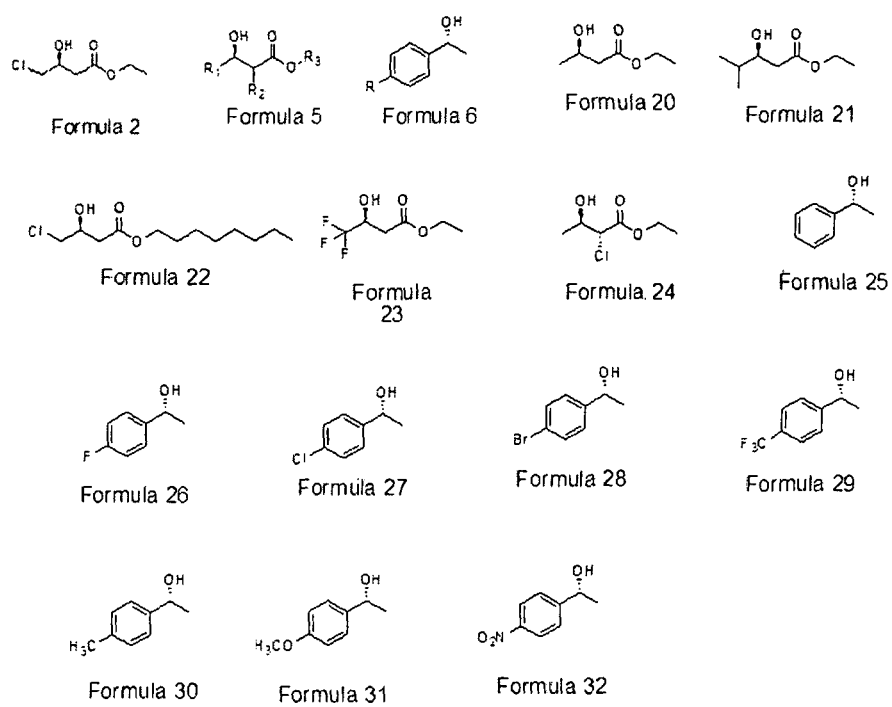
Figure 2: Examples of compounds serving as products

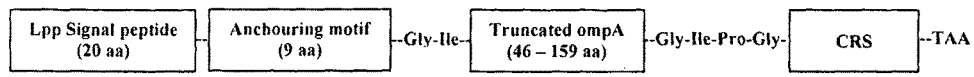
Figure 3: Schematic representation of 'CRS polypeptide' corresponding to SEQ ID No.1, 3, 5 or 7.
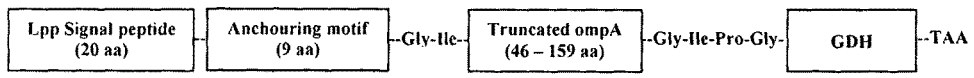
Figure 4: Schematic representation of 'CRS polypeptide' corresponding to SEQ ID No.9, or 11.

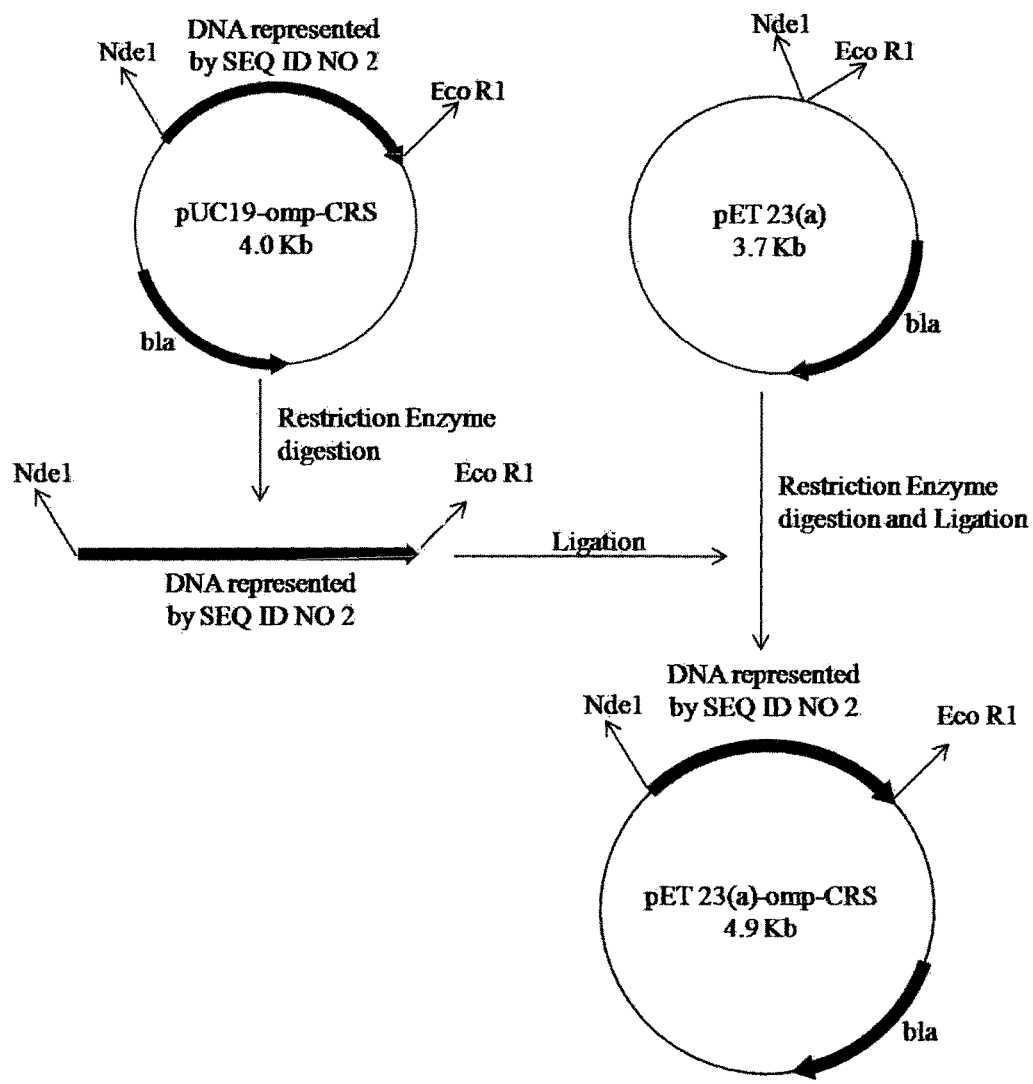
Figure 5: Recombinant Vector pET239a)-omp-CRS

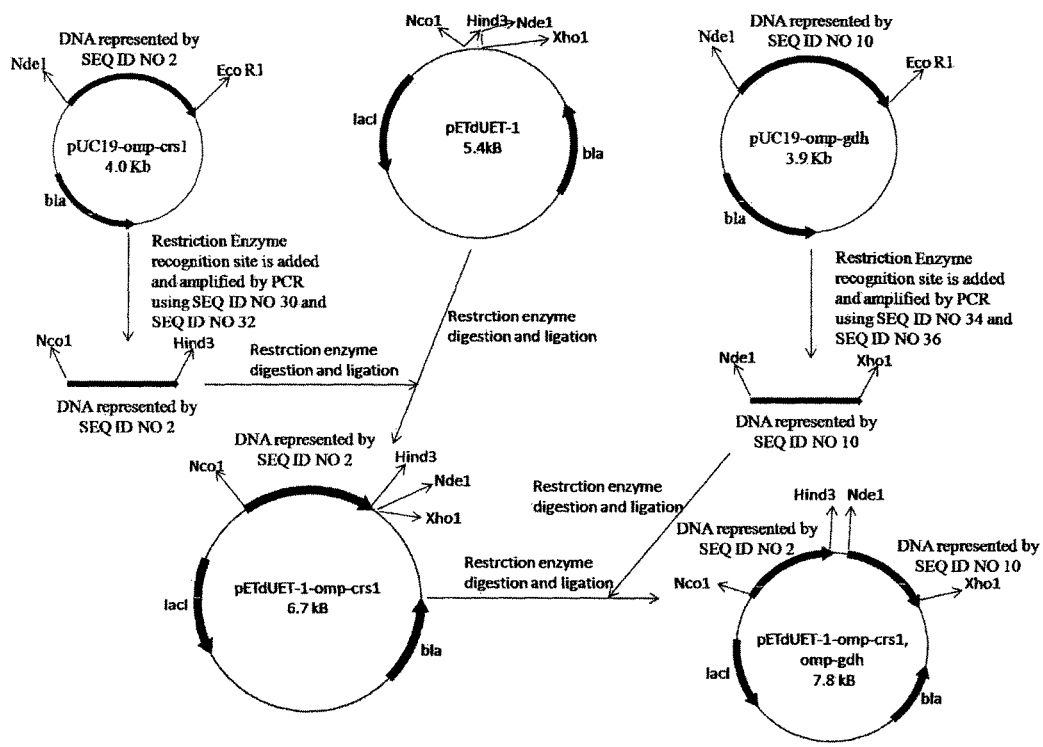
Figure 6: Recombinant Vectors pETDuet1-omp-CRS, omp-GDH

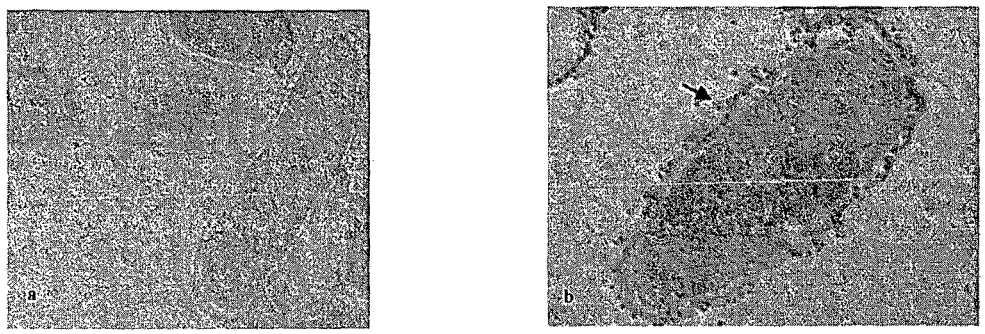
Figure 7: TEM of 'Designer whole-cell biocatalyst'.

DESIGNER CELLS FOR ENANTIOSELECTIVE REDUCTION OF KETONES AND USE THEREOF IN EFFICIENT PRODUCTION OF ENANTIOENRICHED ALCOHOLS

FIELD OF THE INVENTION

The present invention relates to whole cell biocatalysts and use thereof in efficient production of enantioenriched alcohols. More specifically, the present invention relates to the development of whole cell-biocatalysts referred herein as "designer cells" having significantly enhanced conversion rate for asymmetric reduction of variant ketones to their alcohols in high enantiomeric excess. In particular, the present invention relates to the development of a designer cell having significantly enhanced conversion rate for efficient conversion of ethyl 4-chloro-3-oxobutyrate represented by formula 1 to produce ethyl (S)-4-chloro-3-hydroxybutyrate represented by formula 2 in >99.9% enantiomeric excess, which is useful as chiral building block and an intermediate for the production of hydroxymethylglutaryl-CoA (HMG-CoA) reductase inhibitors.

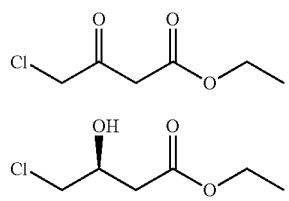

Formula 1

Formula 2

BACKGROUND OF THE INVENTION

In the prior art, examples of methods for preparation of industrially important optically active alcohols including ethyl (S)-4-chloro-3-hydroxybutyrate with the use of wild type whole cell biocatalysts isolated from variant, sources like *Geotrichum candidum* (Sundby, E. et al. *Journal of Molecular Catalysis B: Enzymatic* 2003, 21, 63-66), *Candida parapsilosis* (Kaliaperumal, T. et al. *Journal of Industrial Microbiology & Biotechnology* 2010, 37, 159-165), *Candida magnoliae* (Yasohara, Y. et al. *Applied Microbiology and Biotechnology* 1999, 51, 847-851), *Cylindrocarpon sclerotigenum* (Saratani, Y. et al. *Bioscience, Biotechnology, and Biochemistry* 2001, 65, 1676-1679), *Kluveromyces lactis* (Yamamoto, H., et al. *Bioscience, Biotechnology, and Biochemistry* 2002, 66, 1775-1778), *Kluyveromyces aestuarii* (Yamamoto, H. et al. *Bioscience, Biotechnology, and Biochemistry* 2004, 68, 638-649), *Aureobasidium pullulans* (He, J. Y. et al. *Process Biochemistry* 2006, 41, 244-249), *Pichia stipitis* (Ye, Q. et al. *Biotechnology Letters* 2009, 31, 537-542) and *Streptomyces coelicolor* (Wang, L. J. et al. *Bioresource Technology* 2011, 102, 7023-7028) have been described. Further, methods for producing ethyl (S)-4-chloro-3-hydroxybutyrate with the use of wild type whole cell biocatalysts have been disclosed in U.S. Patent Ser. No. 99/5891685; U.S. Patent Ser. No. 97/5700670; U.S. Patent Ser. No. 96/5559030; U.S. Patent Ser. No. 95/5413921; U.S. Patent Ser. No. 90/4933282 and U.S. Patent Ser. No. 87/4710468. Although, the methods that describe use of wild type microorganism for reduction of carbonyl group to corresponding alcohol exist, these suffer from drawbacks, such as lower efficiency, lower substrate concentration, lower optical purity, etc. Therefore, it is impractical to synthesize industrially important optically active alcohols including ethyl (S)-4-chloro-3-hydroxybutyrate using wild type natural whole cell biocatalysts.

Further known methods to improve optical purity of industrially important optically active alcohols including ethyl (S)-4-chloro-3-hydroxybutyrate, include the use of an enzyme purified from the native source, like *Candida magnoliae* (Wada, M. et al. *Bioscience, Biotechnology, and Biochemistry* 1998, 62, 280-285), *Sporobolomyces salmonicolor* (Kita, K. et al. *Journal of Molecular Catalysis B: Enzymatic* 1999, 6, 305-313), *Kluyveromyces lactis* (Yamamoto, H. et al. *Bioscience, Biotechnology, and Biochemistry* 2002, 66, 1775-1778), *Kluyveromyces aestuarii* (Yamamoto, H. et al. *Bioscience, Biotechnology, and Biochemistry* 2004, 68, 638-649), *Pichia stipitis* (Ye, Q., et al. *Bioresource Technology* 2009, 100, 6022-6027) and *Streptomyces coelicolor* (Wang, L. J. et al. *Bioresource Technology* 2011, 102, 7023-7028).

When a purified enzyme or transformant having carbonyl reductase activity reduces carbonyl group of ketones including ethyl 4-chloro-3-oxobutyrate, it requires a coenzyme, nicotinamide adenine dinucleotide, reduced (NADH) or nicotinamide adenine dinucleotide phosphate, reduced (NADPH) for preparation of industrially important optically active alcohols including ethyl (S)-4-chloro-3-hydroxybutyrate. As the reaction proceeds, coenzyme is converted into nicotinamide adenine dinucleotide phosphate, reduced (NADPH) or nicotinamide adenine dinucleotide phosphate (NADP). In the absence of cofactor regenerating system, stoichiometric amount of expansive cofactor is required. However, when the reaction is done in presence of a cofactor regenerating system, the amount of an expansive coenzyme is greatly reduced. A cofactor regenerating system typically consists of an enzyme which in presence of its substrate converts nicotinamide adenine dinucleotide phosphate, reduced (NADPH) or nicotinamide adenine dinucleotide phosphate (NADP) to nicotinamide adenine dinucleotide, reduced (NADH) or nicotinamide adenine dinucleotide phosphate, reduced (NADPH). Coenzyme regeneration ability can be fulfilled either by the use of purified enzyme (Yasohara, Y. et al. *Bioscience, Biotechnology, and Biochemistry* 2000, 64, 1430-1436; Kaluzna, I. A. et al. *Journal of the American Chemical Society* 2004, 126, 12827-12832; Zhu, D. et al. *The Journal of Organic Chemistry* 2006, 71, 4202-4205; Ye, Q. et al. *Biotechnology Letters* 2009, 31, 537-542), or a transformant having coenzyme regeneration ability in the cytoplasm (Xu, Z. et al. *Applied Microbiology and Biotechnology* 2006, 70, 40-46; Zhang, J. et al. *Chemical Communications* 2006, 398-400).

Methods such as in vitro enzyme evolution using gene shuffling technologies have been employed to improve the activity of a ketoreductase that asymmetrically reduces ethyl 4-chloro-3-oxobutyrate by about 13-fold and glucose dehydrogenase that recycles cofactor nicotinamide adenine dinucleotide phosphate (NADP) or nicotinamide adenine dinucleotide phosphate, reduced (NADPH) using glucose a substrate by about 7-fold compared to corresponding wild type enzyme (Steve K. Ma et al. *Green Chemistry* 2010, 12, 81-86; U.S. patent Ser. No. 10/002,8972; U.S. patent Ser. No. 10/781,6111).

However, the use of an isolated enzyme requires additional steps, such as isolation, purification and stabilization of enzyme, which adds to the cost and makes the overall process for production of optically active alcohols economically unattractive. In addition, inhibition of enzyme by substrate and/or product can sometimes occur. The use of two enzymes, one for reduction of carbonyl compound and other for cofactor recycling along with two substrates, one for each enzyme leads to complex overall kinetics of the reaction. Put together, these factors make the use of isolated enzymes less attractive compared to use of whole cells in the preparation of enantiomerically enriched alcohols including ethyl (S')-4-chloro-3-hydroxybutyrate.

To overcome the problem of low efficiency associated with wild type strains, the gene encoding the carbonyl reductase activity can be deduced and overexpressed in a host cell. Further improvement in efficiency of whole cell biocatalyst for production of enantiomerically enriched alcohols including ethyl (S)-4-chloro-3-hydroxybutyrate is achieved by coexpressing both carbonyl reductase and coenzyme regeneration ability in the cytoplasm of same host (Kizaki, N. et al. *Applied Microbiology and Biotechnology* 2001, 55, 590-595, Kataoka, M. et al. *Enzyme and Microbial Technology* 2006, 38, 944-951; Ye, Q. et al. *Bioresource Technology* 2010, 101, 6761-6767).

However, the method that use either a transformant wherein carbonyl reductase ability is present or a transformant wherein both carbonyl reductase and coenzyme regenerating ability is present in the cytoplasm of cells suffers from drawbacks such as low efficiency due to barrier imposed by plasma membrane on substrate uptake and product efflux, complex kinetics of the overall process, etc.

Consequently, the current methods for the production of optically pure ethyl (S)-4-chloro-3-hydroxybutyrate and other optically enriched alcohols suffer from drawback such as low efficiency, low productivity, etc., which therefore results in increased cost of production.

The art of expressing a protein including enzymes on surface of cells is well known (Lee, S. Y. et al. *Trends in Biotechnology* 2003, 21, 45-52) and has been used in a wide range of biotechnological and industrial applications like whole-cell biocatalyst for bioconversion (Shimazu, M. et al. *Protein. Biotechnology Progress* 2001, 17, 76-80; Shimazu, M. et al. *Biotechnology and Bioengineering* 2001, 76, 318-324), bioadsorbent for the removal of harmful chemicals and heavy metals (Bae, W. et al. *Biotechnology and Bioengineering* 2000, 70, 518-524; Bae, W. et al. *J Inorg Biochem* 2002, 88, 223-227; Sousa, C. et al. *J Bacteriol*. 1998, 180, 2280-2284; Xu, Z. et al. *Appl Environ Microbiol* 1999, 65, 5142-5147), screening of human antibodies libraries (Chao, G. et al. *Nat. Protocols* 2006, 1, 755-768), mutation detection (Aoki, T. et al. *Analytical Biochemistry* 2002, 300, 103-106), biosensor development by anchoring enzymes, receptors or other signal-sensitive components (Dhillon, J. K. et al. *Letters in Applied Microbiology* 1999, 28, 350-354; Shibasaki, S. et al. *Applied Microbiology and Biotechnology* 2001, 57, 702-707; Shibasaki, S. S. et al. *Applied Microbiology and Biotechnology* 2001, 57, 528-533).

More recently, a method for simultaneous display of a target protein including dehydrogenase but not carbonyl reductase and glucose dehydrogenase has been disclosed in U.S. patent Ser. No. 11/789,7366. Usually the cell surface proteins or their truncated form (carrier proteins) fused with the target peptide or protein (passenger protein) are used to display the protein on the surface. Gram (−) ve (*Escherichia coli*), gram (+) ve (*Bacillus subtilis, Staphylococcus* strains) bacteria and yeast (*Saccharomyces cerevisiae, Pichia pastoris*) have been explored for display of heterologous protein expression on the surface. Rigid structure of the cell wall of gram (+) ve bacteria makes it a suitable host, however, the gram (−) ve *Escherichia coli* has been the most popular and much explored for the cell surface display. Integral proteins of *Escherichia coli*, such as LamB, FhuA, and the porins OmpA, OmpC and OmpX, which give structural rigidity to outer membrane has been extensively used for insertion of short amino acid sequence (up to 60 amino acid) in extracellular loop and display it on the cell surface. Outer membrane lipoproteins are anchored in the membrane by a small lipid modified amino terminal. The first lipoprotein based cell surface display was Lpp-OmpA chimera consisting of the 20 amino acid signal sequence and first nine N-terminal residues of the mature *Escherichia coli* lipoprotein, and the residues 46-159 of the *Escherichia coli* outer membrane protein A (OmpA) were fused to the N-terminal of the passenger protein.

BRIEF DESCRIPTION OF THE DRAWINGS

FIG. 1: Examples of compounds serving as substrates.
FIG. 2: Examples of compounds serving as products.
FIG. 3: Schematic representation of "CRS polypeptide" construct corresponding to SEQ ID No: 1, 3, 5 or 7. The sequence consists of (i) N-terminal 20-amino acid signal sequence linked to first nine N-terminal residues of mature *Escherichia coli* lipoprotein (Lpp), (ii) residues 46-159 of *Escherichia coli* outer membrane proteinA (OmpA), which is expected to transport the passenger protein fused at its C-terminal across the membrane and (iii) full sequence of CRS, wherein CRS is wild type carbonyl reductase of *Candida magnoliae* SEQ ID NO: 13 or modified carbonyl reductase SEQ ID No: 15, 17 or 19, which differs from SEQ ID NO: 13 by having several amino acid substitutions. The $1^{st}$ 29 aa residue signal+Lpp peptide was linked to 114 aa OmpA residue through Gly-Ile linker, which in turn was attached to N-terminal of CRS through Gly-Ile-Pro-Gly.

FIG. 4: Schematic representation of "GDH polypeptide" construct corresponding to SEQ ID No: 9 or 11. The sequence consists of (i) N-terminal 20-amino acid signal sequence linked to first nine N-terminal residues of mature *Escherichia coli* lipoprotein (Lpp), (ii) residues 46-159 of *Escherichia coli* outer membrane protein A (OmpA), which is expected to transport the passenger protein fused at its C-terminal across the membrane and (iii) full sequence of GDH, wherein GDH is wild type glucose dehydrogenase of *Bacillus megaterium* SEQ ID NO: 21 or modified glucose dehydrogenase SEQ ID NO: 23, which differs from SEQ ID NO: 21 by having several amino acid substitutions. The $1^{st}$ 29 aa residue signal+Lpp peptide was linked to 114 aa OmpA residue through Gly-Ile linker, which in turn was attached to N-terminal of GDH through Gly-Ile-Pro-Gly.

FIG. 5: Method and structure of recombinant vector pET23(a)-omp-CRS.
FIG. 6: Method and structure of recombinant vector pETDuet1-omp-CRS, omp-GDH.
FIG. 7: Transmission electron micrographs (TEM) of 'Designer whole-cell biocatalyst' expressing CRS on the surface of *Escherichia coli* cells. The cells were probed with rabbit anti-CRS polyclonal antibody followed by nanogold labeled goat anti-rabbit IgG (whole molecule) secondary antibody. Arrowheads denote gold particles. FIG. 7a is TEM of *Escherichia coli* BL21(DE3)+pET 23(a) i.e. negative control, which does not show any gold labeling. FIG. 7b shows TEM of *Escherichia coli* BL21(DE3)+pET 23(a)-omp-CRS that expresses CRS on surface, which shows intense gold labeling.

SUMMARY OF THE INVENTION

The present invention provides an *Escherichia coli* strain that expresses a CRS polypeptide on the surface of cell that has 250-fold to 300-fold enhanced rate of conversion per unit mass of CRS polypeptide compared to corresponding prior art *Escherichia coli* strain that expresses CRS in cytoplasm of cell for reduction of ethyl 4-chloro-3-oxobutyrate to ethyl 4-chloro-3-hydroxybutyrate.

In an embodiment, the recombinant *Escherichia coli* strain that expresses CRS polypeptide on the surface of cell has 50-fold to 275-fold enhanced rate of conversion per unit mass of CRS polypeptide compared to corresponding prior art *Escherichia coli* strain that expresses CRS in cytoplasm of cell for asymmetric reduction of variant keto compounds.

In an embodiment, recombinant *Escherichia coli* strain that expresses a CRS polypeptide on the surface of cell that has about 3-fold to 26-fold enhanced rate of conversion per unit cell mass compared to corresponding prior art *Escherichia coli* strain that expresses CRS in cytoplasm of cell for reduction of variant keto compounds In another aspect the invention is directed to provide a recombinant *Escherichia coli* strain that simultaneously expresses a CRS polypeptide and a GDH polypeptide on the surface of cell that has 250-fold to 300-fold enhanced rate of conversion for reduction of ethyl 4-chloro-3-oxobutyrate to ethyl 4-chloro-3-hydroxybutyrate per unit mass of CRS polypeptide and 200-fold to 250-fold enhanced activity for oxidation of glucose to gluconate per unit mass GDH polypeptide compared to *Escherichia coli* strain that simultaneously expresses a CRS and a GDH in cytoplasm of *Escherichia coli* cell.

In an embodiment, the recombinant *Escherichia coli* strain that simultaneously expresses a CRS polypeptide and a GDH polypeptide on the surface of cell has about 50-fold to 270-fold enhanced rate of conversion per unit mass of CRS protein compared to corresponding prior art *Escherichia coli* strain that simultaneously expresses a CRS polypeptide and a GDH polypeptide in cytoplasm of cell for reduction of variant ketones.

In an embodiment, recombinant *Escherichia coli* strain that simultaneously expresses a CRS polypeptide and a GDH polypeptide on the surface of cell that has about 3-fold to 24-fold enhanced rate of conversion per unit cell mass compared to corresponding prior art *Escherichia coli* strain that simultaneously expresses a CRS polypeptide and a GDH polypeptide in cytoplasm of cell for reduction of variant keto compounds In one embodiment, the variant ketone is an aliphatic compound represented by formula 3; wherein $R_1$=$CH_3$, $CH_2X$, $(CH_3)_2CH$, $CF_3$ or $CH_3(CH_2)_n$ and $R_2$=H, X or $CH_3(CH_2)_n$ and $R_3$=alkyl group such as $CH_3$ or $CH_3(CH_2)_m$ and X=Cl or Br and n=1-4 and m=1-8.

In a more preferred embodiments, $R_1$ is $CH_2Cl$, $R_2$ is H and $R_3$ is $CH_2CH_3$ or $R_1$ is $CH_3$, $R_2$ is H and $R_3$ is $CH_2CH_3$ or $R_1$ is $CH_2Cl$, $R_2$ is H and $R_3$ is $(CH_2)_7CH_3$ or $R_1$ is $CH_3$, $R_2$ is Cl and $R_3$ is $CH_2CH_3$ or $R_1$ is $CF_3$, $R_2$ is H and $R_3$ is $CH_2CH_3$ or $R_1$ is $(CH_3)_2CH$, $R_2$ is H and $R_3$ is $CH_2CH_3$.

In another embodiment, the variant ketone is an aromatic compound represented by general formula 4 wherein $R_1$=$R_2$=$R_3$=$R_4$=$R_5$=H, $CH_3$, F, Cl, Br, I, $CF_3$, $NO_2$ or $OCH_3$ and $R_6$=alkyl group such as $CH_3$ or $CH_3(CH_2)$, and n=1 to 5.

In an embodiment, the *Escherichia coli* strain is selected from *Escherichia coli* BL21(DE3), *Escherichia coli* C41(DE3) or *Escherichia coli* C43(DE3).

In a preferred embodiment, the rate of conversion of ethyl 4-chloro-3-oxobutyrate to ethyl (S)-4-chloro-3-hydroxybutyrate with nicotinamide adenine dinucleotide phosphate, reduced (NADPH) as cofactor is 1.3-fold higher when *Escherichia coli* strain BL21(DE3) that simultaneously expresses a CRS polypeptide and a GDH polypeptide on surface of cell is replaced with *Escherichia coli* C41(DE3) that simultaneously expresses a CRS polypeptide and a GDH polypeptide on surface of cell.

In another preferred embodiment, the rate of conversion of ethyl 4-chloro-3-oxobutyrate to ethyl (S)-4-chloro-3-hydroxybutyrate with nicotinamide adenine dinucleotide phosphate, reduced (NADPH) as cofactor is about 1.6-fold higher with *Escherichia coli* strain C41(DE3) that simultaneously expresses a CRS polypeptide and a GDH polypeptide on surface of cell compared to *Escherichia coli* strain BL21(DE3) that expresses only CRS polypeptide on the surface of cell, requiring addition of external GDH for cofactor recycling.

In a specific embodiment, the present invention provide a production method for producing industrially important ethyl (S)-4-chloro-3-hydroxybutyrate in about 100% enantiomeric excess with high productivity and product accumulation of at least 150 $gl^{-1}$.

DETAILED DESCRIPTION OF THE INVENTION

While the invention is susceptible to various modifications and/or alternative processes and/or compositions, specific embodiment thereof has been shown by way of example in the drawings/figures and tables and will be described in detail below. It should be understood, however that it is not intended to limit the invention to the particular processes and/or compositions disclosed, but on the contrary, the invention is to cover all modifications, equivalents, and alternative falling within the spirit and the scope of the invention as defined by the appended claims.

The graphs, figures, tables, formulas and protocols have been represented where appropriate by conventional representations in the drawings, showing only those specific details that are pertinent to understanding the embodiments of the present invention so as not to obscure the disclosure with details that will be readily apparent to those of ordinary skill in the art having benefit of the description herein.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

Definitions

For the purposes of this invention, the following terms will have the meaning as specified therein:

"CRS polypeptide" refers to an amino acid sequence which is schematically shown in FIG. 3.

"GDH polypeptide" refers to a sequence which is schematically shown in FIG. 4.

"Carbonyl reductase" and "CRS" are used interchangeably and refer to polypeptide that converts a ketone and nicotinamide adenine dinucleotide phosphate, reduced (NADPH) to corresponding alcohol and nicotinamide adenine dinucleotide phosphate (NADP).

"Glucose dehydrogenase" and "GDH" are used interchangeably and refers to a polypeptide that converts glucose and nicotinamide adenine dinucleotide phosphate (NADP) to gluconate and nicotinamide adenine dinucleotide phosphate, reduced (NADPH).

In the description, the term 'designer cell' refers herein to a recombinant strain of Escherichia coli that catalyze the asymmetric reduction of variant ketones to produce enantioenriched alcohols using catalytic amount of reduced nicotinamide adenine dinucleotide phosphate (NADPH) as a reducing agent with or without addition of external co-factor recycling system for oxidation of nicotinamide adenine dinucleotide phosphate (NADP) to nicotinamide adenine dinucleotide phosphate, reduced (NADPH).

Further, the term "cofactor recycling system" refers herein to a set of reagents which are added to the reaction for conversion of spent cofactor back to its pre-reaction state. For example, in conversion of ketone to alcohol by CRS, cofactor nicotinamide adenine dinucleotide phosphate, reduced (NADPH) gets converted to nicotinamide adenine dinucleotide phosphate (NADP) (spent cofactor). Addition of reagents, GDH and glucose to the reaction will result in regeneration of nicotinamide adenine dinucleotide phosphate, reduced (NADPH) from nicotinamide adenine dinucleotide phosphate (NADP).

Further, the term "CRS polypeptide" refers to an amino acid sequence which is schematically shown in FIG. 3 in which CRS is wild type carbonyl reductase of Candida magnoliae SEQ ID NO: 13 or modified carbonyl reductase that differs from SEQ ID NO: 13 by having several amino acid substitutions, such as SEQ ID NO: 15 (P14A, S42N, A194V, I275V) or SEQ ID NO: 17 (P14A, S42N, V147A, A194V, E234G) or SEQ ID NO: 19 (E9G, P14A, N20S, S42N, T190A, A194V, E234G).

Further GDH polypeptide refers to a sequence which is schematically shown in FIG. 4 in which GDH is wild type glucose dehydrogenase of Bacillus megaterium SEQ ID NO: 21 or modified glucose dehydrogenase that differs from SEQ ID NO: 21 by having several amino acid substitution such as SEQ ID NO: 23 (S16T, E170K, P194T, A197K, E222D, S237C).

As used herein, the terms "carbonyl reductase" and "CRS" are used interchangeably and refer to polypeptide that converts a ketone and nicotinamide adenine dinucleotide phosphate, reduced (NADPH) to corresponding alcohol and nicotinamide adenine dinucleotide phosphate (NADP). Further, the terms "glucose dehydrogenase" and "GDH" are used interchangeably and refers to a polypeptide that converts glucose and nicotinamide adenine dinucleotide phosphate (NADP) to gluconate and nicotinamide adenine dinucleotide phosphate, reduced (NADPH).

The present invention provides whole cell-biocatalyst referred herein as "designer cell" having significantly enhanced conversion rate for enantioselective reduction of variant ketones to their alcohols in high enantiomeric excess In particular, the present invention relates to the development of a designer cell having significantly enhanced conversion rate for efficient conversion of ethyl 4-chloro-3-oxobutyrate represented by formula 1 to produce ethyl (S)-4-chloro-3-hydroxybutyrate represented by formula 2 in >99.9% enantiomeric excess, which is useful as chiral building block and an intermediate for the production of hydroxymethylglutaryl-CoA (HMG-CoA) reductase inhibitors.

The present invention provides for expression of carbonyl reductase polypeptide (CRS) on the cell surface. Further the present invention also provides for co-expression carbonyl reductase polypeptide (CRS) and gluconase dehryogenase (GDH) on the surface. Thus the present invention overcomes the existing drawback of whole-cell system expressing carbonyl reductase in cytoplasm, wherein the carbonyl reductase polypeptide (CRS) is anchored to the surface of cell and has shown unexpected and surprising enhanced conversion rate per unit mass of CRS polypeptide compared to carbonyl reductase expressed in cytoplasm of same host for the conversion of ethyl 4-chloro-3-oxobutyrate to industrially important ethyl (S)-4-chloro-3-hydroxybutyrate. Likewise the present invention also overcome the existing drawback of whole-cell system co-expression CRS and GDH enzymes in cytoplasm, wherein the CRS and GDH are anchored to the surface of cell and coexpressed, wherein the coexpresion has shown unexpected and surprising enhanced expression. Moreover, an enzymes expressed in such a manner is expected to behave like a pure, immobilized enzymes, thereby obviating the need for cost-intensive isolation, purification and stabilization of the enzyme. Moreover, kinetics is expected to be much simpler because of the fact that substrate uptake and product efflux across plasma membrane is not required in this case.

Surprisingly the present invention works with the hypothesis that the efficiency of designer cell can be further improved if both CRS and glucose dehydrogenase (GDH) activities are coexpressed in the same host, possibly because with such a biocatalyst, the cofactor nicotinamide adenine dinucleotide phosphate, reduced (NADPH)/nicotinamide adenine dinucleotide phosphate (NADP) will not become completely free in solution; instead, it will get channelized between CRS and GDH which are localized in close proximity on the surface of cell.

Accordingly, the present invention provides for a designed transformant, wherein enzyme carbonyl reductase and coenzyme regenerating enzyme (e.g., a glucose dehydrogenase) are coexpressed together on the surface of cell, which has several fold improved efficiency compared to the transformant that expresses only CRS on the surface of a cell and requires external addition of GDH for cofactor recycling in conversion of ethyl (S)-4-chloro-3-oxobutanoate to ethyl (S)-4-chloro-3-hydroxybutyrate.

The present invention provides a method for production of industrially important ethyl (S)-4-chloro-3-hydroxybutyrate in about 100% enantiomeric excess with high productivity and product accumulation of at least 150 g l$^{-1}$.

The present invention also provides a 'designer cell' which is a recombinant strain of Escherichia coli that catalyze the asymmetric reduction of variant ketones to produce enantioenriched alcohols using catalytic amount of reduced nicotinamide adenine dinucleotide phosphate (NADPH) as a reducing agent with or without addition of external co-factor recycling system for oxidation of nicotinamide adenine dinucleotide phosphate (NADP) to nicotinamide adenine dinucleotide phosphate, reduced (NADPH). The strain of Candia magnoliae is AKU4643 and Bacillus megaterium is DSM 2894.

The present invention provides for a designer cell which comprises of "CRS" polypeptide construct corresponding to SEQ ID No. 1, 3, 5 or 7. The designer cell as described in the present invention has (a) N-terminal 20-amino acid signal sequence linked to first nine N-terminal residues of mature *Escherichia coli* lipoprotein (Lpp); (b) residues 46-159 of *Escherichia coli* outer membrane proteinA (OmpA), which is expected to transport the passenger protein fused at its C-terminal across the membrane; and (c) full sequence of CRS, wherein CRS is wild type carbonyl reductase of *Candida magnoliae* SEQ ID NO: 13 or modified carbonyl reductase SEQ ID No: 15, 17 or 19, which differs from SEQ ID NO: 13 by having several amino acid substitutions. The $1^{st}$ 29 aa residue signal+Lpp peptide was linked to 114 aa OmpA residue through Gly-Ile linker, which in turn was attached to N-terminal of CRS through Gly-Ile-Pro-Gly (FIG. 3). The modified carbonyl reductase that differs from SEQ ID NO: 13 by having several amino acid substitutions, such as SEQ ID NO: 15 (P14A, S42N, A194V, I275V) or SEQ ID NO: 17 (P14A, S42N, V147A, A194V, E234G) or SEQ ID NO: 19 (E9G, P14A, N20S, S42N, T190A, A194V, E234G).

The present invention also provides for a designer cell which comprises of "GDH" polypeptide construct corresponding to SEQ ID No. 9 or 11. The designer cell as described in the present invention has (a) N-terminal 20-amino acid signal sequence linked to first nine N-terminal residues of mature *Escherichia coli* lipoprotein (Lpp); (b) residues 46-159 of *Escherichia coli* outer membrane proteinA (OmpA), which is expected to transport the passenger protein fused at its C-terminal across the membrane; and (c) full sequence of GDH, wherein GDH is wild type glucose dehydrogenase (GDH) of *Bacillus megaterium* SEQ ID NO: 21 or modified carbonyl reductase SEQ ID No: 23, which differs from SEQ ID NO: 21 by having several amino acid substitutions. The $1^{st}$ 29 aa residue signal+Lpp peptide was linked to 114 aa OmpA residue through Gly-Ile linker, which in turn was attached to N-terminal of CRS through Gly-Ile-Pro-Gly (FIG. 3). The modified glucose dehydrogenase that differs from SEQ ID NO: 21 by having several amino acid substitution such as, SEQ ID NO: 23 (S16T, E170K, P194T, A197K, E222D, S237C).

The present invention also provides for a cofactor recycling system which refers herein to a set of reagents which are added to the reaction for conversion of spent cofactor back to its pre-reaction state. For example, in conversion of ketone to alcohol by designer cell, cofactor nicotinamide adenine dinucleotide phosphate, reduced (NADPH) gets converted to nicotinamide adenine dinucleotide phosphate (NADP) (spent cofactor). Addition of reagents, GDH and glucose to the reaction will result in regeneration of nicotinamide adenine dinucleotide phosphate, reduced (NADPH) from nicotinamide adenine dinucleotide phosphate (NADP).

The invention presented herein has multiple aspects. In one aspect the invention is directed to construction of a recombinant *Escherichia coli* strain that expresses a CRS polypeptide on the surface of cell that has 250-fold to 300-fold enhanced rate of conversion per unit mass of CRS polypeptide compared to corresponding prior art *Escherichia coli* strain that expresses CRS in cytoplasm of cell for reduction of ethyl 4-chloro-3-oxobutyrate to ethyl 4-chloro-3-hydroxybutyrate as measured by decrease in absorbance of nicotinamide adenine dinucleotide phosphate, reduced (NADPH). The relative amount of CRS polypeptide was determined by immunoblotting (Example 7).

In an embodiment, the recombinant *Escherichia coli* strain that expresses CRS polypeptide on the surface of cell has about 50-fold to 275-fold enhanced rate of conversion per unit mass of CRS protein compared to corresponding prior art *Escherichia coli* strain that expresses CRS in cytoplasm of cell for reduction of variant keto compounds as measured by decrease in absorbance of nicotinamide adenine dinucleotide phosphate, reduced (NADPH). The relative CRS protein content was determined by immunoblotting (Example 7).

In one embodiment, the ketone is an aliphatic compound represented by formula 3.

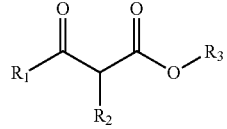

Formula 3 wherein $R_1$=CH$_3$, CH$_2$X, (CH$_3$)$_2$CH, CF$_3$ or CH$_3$(CH$_2$)$_n$
$R_2$=H, X or CH$_3$(CH$_2$)$_n$;
$R_3$=alkyl group such as CH$_3$ or CH$_3$(CH$_2$)$_m$;
X=Cl or Br;
n=1-4 and
m=1-8.

In a more preferred embodiments, $R_1$ is CH$_2$Cl, $R_2$ is H and $R_3$ is CH$_2$CH$_3$ or $R_1$ is CH$_3$, $R_2$ is H and $R_3$ is CH$_2$CH$_3$ or $R_1$ is CH$_2$Cl, $R_2$ is H and $R_3$ is (CH$_2$)$_7$CH$_3$ or $R_1$ is CH$_3$, $R_2$ is Cl and $R_3$ is CH$_2$CH$_3$ or $R_1$ is CF$_3$, $R_2$ is H and $R_3$ is CH$_2$CH$_3$ or $R_1$ is (CH$_3$)$_2$CH, $R_2$ is H and $R_3$ is CH$_2$CH$_3$ In another embodiment, the ketone is an aromatic compound represented by formula 4

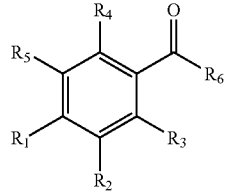

Formula 4

Wherein $R_1$=$R_2$=$R_3$=$R_4$=$R_5$=H, CH$_3$, F, Cl, Br, I, CF$_3$, NO$_2$ or OCH$_3$;
$R_6$=alkyl group such as CH$_3$ or CH$_3$(CH$_2$)$_n$ and
n=1 to 5.

As stated herein, the prior art *Escherichia coli* used for comparison of CRS activity refers to *Escherichia coli* strain that expresses wild type carbonyl reductase of *Candida magnoliae* SEQ ID NO: 13 or modified carbonyl reductase polypeptide SEQ ID NO: 15, SEQ ID NO: 17 or SEQ ID NO: 19 in the cytoplasm. These *Escherichia coli* strains were constructed by using the art disclosed in US Patent 2010/0028972.

In another aspect the invention is directed to construction of a recombinant *Escherichia coli* strain that expresses a CRS polypeptide on the surface of cell that has about 15-fold to 26-fold enhanced rate of conversion per unit cell mass compared to corresponding prior art *Escherichia coli* strain that expresses CRS in cytoplasm of cell for reduction of ethyl 4-chloro-3-oxobutyrate to ethyl 4-chloro-3-hydroxybutyrate as measured by decrease in absorbance of nicotinamide adenine dinucleotide phosphate, reduced (NADPH).

In an embodiment, recombinant *Escherichia coli* strain that expresses a CRS polypeptide on the surface of cell that has about 3-fold to 26-fold enhanced rate of conversion per unit cell mass compared to corresponding prior art *Escherichia coli* strain that expresses CRS in cytoplasm of cell for reduction of variant keto compounds as measured by decrease in absorbance of nicotinamide adenine dinucleotide phosphate, reduced (NADPH).

In one embodiment, the ketone is an aliphatic compound represented by formula 3 wherein $R_1$=$CH_3$, $CH_2X$, $(CH_3)_2CH$, $CF_3$ or $CH_3(CH_2)_n$ and $R_2$=H, X or $CH_3(CH_2)_n$ and $R_3$=alkyl group such as $CH_3$ or $CH_3(CH_2)_m$ and X=Cl or Br and n=1-4 and m=1-8.

In a more preferred embodiments, $R_1$ is $CH_2Cl$, $R_2$ is H and $R_3$ is $CH_2CH_3$ or $R_1$ is $CH_3$, $R_2$ is H and $R_3$ is $CH_2CH_3$ or $R_1$ is $CH_2Cl$, $R_2$ is H and $R_3$ is $(CH_2)_7CH_3$ or $R_1$ is $CH_3$, $R_2$ is Cl and $R_3$ is $CH_2CH_3$ or $R_1$ is $CF_3$, $R_2$ is H and $R_3$ is $CH_2CH_3$ or $R_1$ is $(CH_3)_2CH$, $R_2$ is H and $R_3$ is $CH_2CH_3$ In another embodiment, the ketone is an aromatic compound represented by general formula 4 wherein $R_1$=$R_2$=$R_3$=$R_4$=$R_5$=H, $CH_3$, F, Cl, Br, I, $CF_3$, $NO_2$ or $OCH_3$ and $R_6$=alkyl group such as $CH_3$ or $CH_3(CH_2)_n$ and n=1 to 5.

In yet another aspect, the invention is directed to construction of a recombinant *Escherichia coli* strain that simultaneously expresses a CRS polypeptide and a GDH polypeptide on the surface of cell that has 250-fold to 300-fold enhanced rate of conversion for reduction of ethyl 4-chloro-3-oxobutyrate to ethyl 4-chloro-3-hydroxybutyrate per unit mass of CRS polypeptide and 200-fold to 250-fold enhanced activity for oxidation of glucose to gluconate per unit mass GDH polypeptide compared to *Escherichia coli* strain that simultaneously expresses a CRS and a GDH in cytoplasm of *Escherichia coli* cell. CRS activity was measured by decrease in absorbance of nicotinamide adenine dinucleotide phosphate, reduced (NADPH). The relative amount of CRS polypeptide was determined by immunoblotting (Example 7). GDH activity and the relative amount GDH polypeptide was measured as described in Example 11.

In an embodiment, the recombinant *Escherichia coli* strain that simultaneously expresses a CRS polypeptide and a GDH polypeptide on the surface of cell has about 50-fold to 270-fold enhanced rate of conversion per unit mass of CRS protein compared to corresponding prior art *Escherichia coli* strain that simultaneously expresses a CRS polypeptide and a GDH polypeptide in cytoplasm of cell for reduction of variant keto compounds as measured by decrease in absorbance of nicotinamide adenine dinucleotide phosphate, reduced (NADPH). The relative CRS protein content was determined by immunoblotting (Example 7).

In one embodiment, the ketone is an aliphatic compound represented by formula 3 wherein $R_1$=$CH_3$, $CH_2X$, $(CH_3)_2CH$, $CF_3$ or $CH_3(CH_2)_n$ and $R_2$=H, X or $CH_3(CH_2)_n$ and $R_3$=alkyl group such as $CH_3$ or $CH_3(CH_2)_m$, wherein n=1 to 8 and X=Cl or Br and n=1-4 and m 1-8.

In a more preferred embodiments, $R_1$ is $CH_2Cl$, $R_2$ is H and $R_3$ is $CH_2CH_3$ or $R_1$ is $CH_3$, $R_2$ is H and $R_3$ is $CH_2CH_3$ or $R_1$ is $CH_2Cl$, $R_2$ is H and $R_3$ is $(CH_2)_7CH_3$ or $R_1$ is $CH_3$, $R_2$ is Cl and $R_3$ is $CH_2CH_3$ or $R_1$ is $CF_3$, $R_2$ is H and $R_3$ is $CH_2CH_3$ or $R_1$ is $(CH_3)_2CH$, $R_2$ is H and $R_3$ is $CH_2CH_3$ In another embodiment, the ketone is an aromatic compound represented by general formula 4 wherein $R_1$=$R_2$=$R_3$=$R_4$=$R_5$=H, $CH_3$, F, Cl, Br, I, $CF_3$, $NO_2$ or $OCH_3$ and $R_6$=alkyl group such as $CH_3$ or $CH_3(CH_2)_n$ and n=1 to 5.

As stated herein, the prior art *Escherichia coli* used for comparison of CRS and GDH activity refers to *Escherichia coli* strain that co-expresses wild type carbonyl reductase of *Candida magnoliae* SEQ ID NO: 13 and wild type glucose dehydrogenase of *Bacillus megaterium* SEQ ID NO: 21 in the cytoplasm. These *Escherichia coli* strains were constructed by using the art disclosed by Kizaki, N. et al. *Applied Microbiology and Biotechnology* 2001, 55, 590-595. Further, it refers to *Escherichia coli* strains that co-express variant carbonyl reductase selected from SEQ ID NO: 15, SEQ ID NO: 17 or SEQ ID NO: 19 and variant glucose dehydrogenase selected from SEQ ID NO: 21 SEQ ID NO: 23 in the cytoplasm. These *Escherichia coli* strains were constructed based on the knowledge disclosed in Applied and Microbial Technology, Volume 55, pages 5590-595, year 2001, US Patent 2010/0028972 and US Patent 2010/7816111 with respect to peptide sequence, corresponding nucleotide sequences that code for these peptides and expression vectors.

In another aspect the invention is directed to construction of *Escherichia coli* strain that simultaneously expresses a CRS polypeptide and a GDH polypeptide on the surface of cell that has 11-fold to 24-fold enhanced activity for reduction of ethyl 4-chloro-3-oxobutyrate to ethyl 4-chloro-3-hydroxybutyrate per unit cell mass and 9-fold to 31-fold enhanced activity for oxidation of glucose to gluconate per unit per unit cell mass compared to *Escherichia coli* strain that simultaneously expresses CRS and GDH in cytoplasm of *Escherichia coli* cell. CRS activity was measured by decrease in absorbance of nicotinamide adenine dinucleotide phosphate, reduced (NADPH). GDH activity was measured by increase in absorbance of nicotinamide adenine dinucleotide phosphate (NADP) (Example 11).

In an embodiment, recombinant *Escherichia coli* strain that simultaneously expresses a CRS polypeptide and a GDH polypeptide on the surface of cell that has about 3-fold to 24-fold enhanced rate of conversion per unit cell mass compared to corresponding prior art *Escherichia coli* strain that simultaneously expresses a CRS polypeptide and a GDH polypeptide in cytoplasm of cell for reduction of variant keto compounds as measured by decrease in absorbance of nicotinamide adenine dinucleotide phosphate, reduced (NADPH).

In one embodiment, the ketone is an aliphatic compound represented by formula 3 wherein $R_1$=$CH_3$, $CH_2X$, $(CH_3)_2CH$, $CF_3$ or $CH_3(CH_2)_n$ and $R_2$=H, X or $CH_3(CH_2)_n$ and $R_3$=alkyl group such as $CH_3$ or $CH_3(CH_2)_m$ wherein n=1 to 8 and X=Cl or Br and n=1-4 and m=1-8.

In a more preferred embodiments, $R_1$ is $CH_2Cl$, $R_2$ is H and $R_3$ is $CH_2CH_3$ or $R_1$ is $CH_3$, $R_2$ is H and $R_3$ is $CH_2CH_3$ or $R_1$ is $CH_2Cl$, $R_2$ is H and $R_3$ is $(CH_2)_7CH_3$ or $R_1$ is $CH_3$, $R_2$ is Cl and $R_3$ is $CH_2CH_3$ or $R_1$ is $CF_3$, $R_2$ is H and $R_3$ is $CH_2CH_3$ or $R_1$ is $(CH_3)_2CH$, $R_2$ is H and $R_3$ is $CH_2CH_3$ In another embodiment, the ketone is an aromatic compound represented by general formula 4 wherein $R_1$=$R_2$=$R_3$=$R_4$=$R_5$=H, $CH_3$, F, Cl, Br, I, $CF_3$, $NO_2$ or $OCH_3$ and $R_6$=alkyl group such as $CH_3$ or $CH_3(CH_2)_n$ and n=1 to 5.

Accordingly, an object of the present invention is to provide a designer cell that has an amino acid sequence selected from SEQ ID NO:1, 3, 5 or 7 of the Sequence Listing with the one or several amino acids being deleted, substituted or added in the amino acid sequence of SEQ ID NO: 1, 3, 5 or 7 of the Sequence Listing, expressed on the surface of the transformant/s, having carbonyl reductase activity.

The DNA according to present invention codes for the above polypeptide has nucleotide sequence selected from SEQ ID NO: 2, 4, 6 or 8 of the Sequence Listing.

The plasmid according to present invention that codes for the above polypeptide is pET 23(a)-omp-CRS.

In the description, the amino acid sequence has been assigned odd number. The nucleotide sequence coding for a particular amino acid has been assigned immediately next even number. For example, for amino acid sequence SEQ ID NO: 1, the corresponding coding nucleotide sequence has been assigned sequence SEQ ID NO: 2.

The cell used according to present invention for creating a transformant is selected from *Escherichia coli* BL21 (DE3), *Escherichia coli* C41(DE3) or *Escherichia coli* C43 (DE3).

The transformed cell used according to present invention is transformant/s which is a cell transformed with the above plasmid pET 23(a)-omp-CRS.

In a preferred embodiment, the transformed cells is *Escherichia coli* BL21(DE3)+pET 23(a)-omp-CRS.

In more preferred embodiment the transformed cell is *Escherichia coli* C41(DE3)+pET 23(a)-omp-CRS.

In a preferred embodiment designer cell has an amino acid sequence SEQ ID NO: 1 of the Sequence Listing with the one or several amino acids being deleted, substituted or added in the amino acid sequence of SEQ ID NO: 1 of the Sequence Listing, expressed on the surface of the transformant/s, having carbonyl reductase activity.

The DNA for the above polypeptide has nucleotide sequence SEQ ID NO: 2

The plasmid according to present invention that codes for the above polypeptide is pET 23(a)-omp-CRS.

The cell used according to present invention for creating a transformant is selected from *Escherichia coli* BL21 (DE3), *Escherichia coli* C41(DE3) or *Escherichia coli* C43 (DE3).

The transformed cell used according to present invention is transformant/s which is a cell transformed with the above plasmid pET 23(a)-omp-CRS.

In a preferred embodiment, the transformed cell is *Escherichia coli* BL21(DE3)+pET 23(a)-omp-CRS.

In more preferred embodiment the transformed cell is *Escherichia coli* C41(DE3)+pET 23(a)-omp-CRS.

The transformant according to the present invention that asymmetrically reduces carbonyl group of the substrate including ethyl 4-chloro-3-oxobutyrate for producing industrially important optically pure alcohols including ethyl (S)-4-chloro-3-hydroxybutyrate require coenzyme nicotinamide adenine dinucleotide phosphate, reduced (NADPH). As the reaction proceeds, coenzyme is converted to oxidation type nicotinamide adenine dinucleotide phosphate (NADP). Conversion of the oxidation-type into a reduction type needs another enzyme having coenzyme regeneration ability (e.g. glucose dehydrogenase).

In one embodiment, the glucose dehydrogenase is derived from *Bacillus megaterium*.

Another object of the present invention is to provide designer cell coexpressing on the surface of the transformant, of the two polypeptides, one having CRS activity has an amino acid sequence selected from SEQ ID NO: 1, 3, 5 or 7 of the Sequence Listing with the one or several amino acids being deleted, substituted or added in the amino acid sequence of SEQ ID NO: 1, 3, 5 or 7 of the Sequence Listing, which effectively reduces ethyl (S)-4-chloro-3-hydroxybutyrate and the other having GDH activity has an amino acid sequence selected from SEQ ID NO: 9 or of the Sequence Listing with the one or several amino acids being deleted, substituted or added in the amino acid sequence of SEQ ID NO: 9 or 11 of the Sequence Listing, having coenzyme regeneration activity for producing an optically pure ethyl (S)-4-chloro-3-hydroxybutyrate.

The DNA according to present invention codes for the above polypeptide having carbonyl reductase activity has nucleotide sequence selected from SEQ ID NO: 2, 4, 6 or 8 of the Sequence Listing and for coenzyme regenerating enzyme has nucleotide sequence selected from SEQ ID NO:10 or 12 of the Sequence Listing.

The plasmid according to present invention coding both polypeptides having carbonyl reductase activity and coenzyme regenerating ability is pETDuet1-omp-CRS, omp-GDH.

The transformed cell used according to present invention is transformant which is a cell transformed with the above plasmid pETDuet1-omp-CRS, omp-GDH.

The cell used according to present invention for creating transformant having both carbonyl reductase activity and coenzyme regenerating ability is selected from *Escherichia coli* BL21(DE3), *Escherichia coli* C41(DE3) or *Escherichia coli* C43(DE3).

In a preferred embodiment, the transformed cell is *Escherichia coli* BL21(DE3)+pET pETDuet1-omp-CRS, omp-GDH.

In more preferred embodiment, the transformed cell is *Escherichia coli* C41(DE3)+pETDuet1-omp-CRS, omp-GDH.

In a preferred embodiment, transformant coexpressing on the surface of the transformant, of the two polypeptides, one having CRS activity has an amino acid sequence SEQ ID NO: 1 of the Sequence Listing with the one or several amino acids being deleted, substituted or added in the amino acid sequence of SEQ ID NO: 1 of the Sequence Listing, which effectively reduces ethyl (S)-4-chloro-3-hydroxybutyrate and the other having GDH activity has an amino acid sequence SEQ ID NO: 9 of the Sequence Listing with the one or several amino acids being deleted, substituted or added in the amino acid sequence of SEQ ID NO: 9 of the Sequence Listing, having coenzyme regeneration activity for producing an optically pure ethyl (S)-4-chloro-3-hydroxybutyrate.

The DNA according to present invention codes for the above polypeptide having carbonyl reductase activity has nucleotide sequence SEQ ID NO: 2 of the Sequence Listing and for coenzyme regenerating enzyme has nucleotide sequence SEQ ID NO:10 of the Sequence Listing.

The plasmid according to present invention coding both polypeptides having carbonyl reductase activity and coenzyme regenerating ability is pETDuet1-omp-CRS; omp-GDH. The transformed cell used according to present invention is transformant which is a cell transformed with the above plasmid pETDuet1-omp-CRS; omp-GDH.

In a preferred embodiment, the transformed cell is *Escherichia coli* BL21(DE3)+pET pETDuet1-omp-CRS, omp-GDH.

The cell used according to present invention for creating transformant having both carbonyl reductase activity and coenzyme regenerating ability is selected from *Escherichia coli BL*21(DE3), *Escherichia coli* C41(DE3) or *Escherichia coli* C43(DE3).

In more preferred embodiment, the transformed cell is *Escherichia coli* C41(DE3)+pETDuet1-omp-CRS; omp-GDH.

Another object of the present invention is to provide for a production method for producing industrially important optically active alcohols includes culture condition for the transformant/s, harvesting the culture, reaction condition for substrates having carbonyl group and harvesting the produced optically active alcohols.

In one embodiment, the ketone is an aliphatic compound represented by formula 3 and the resultant optically active alcohol is represented by formula 5.

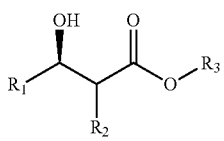

Formula 5 wherein $R_1$=$CH_3$, $CH_2X$, $(CH_3)_2CH$, $CF_3$ or $CH_3(CH_2)_n$
$R_2$=H, X or $CH_3(CH_2)_n$;
$R_3$=alkyl group such as $CH_3$ or $CH_3(CH_2)_m$;
X=Cl or Br;
n=1-4 and
m=1-8.

In a more preferred embodiment, $R_1$ is $CH_2Cl$, $R_2$ is H and $R_3$ is $CH_2CH_3$ or $R_1$ is $CH_3$, $R_2$ is H and $R_3$ is $CH_2CH_3$ or $R_1$ is $CH_2Cl$, $R_2$ is H and $R_3$ is $(CH_2)_7CH_3$ or $R_1$ is $CH_3$, $R_2$ is Cl and $R_3$ is $CH_2CH_3$ or $R_1$ is $CF_3$, $R_2$ is H and $R_3$ is $CH_2CH_3$ or $R_1$ is $(CH_3)_2CH$, $R_2$ is H and $R_3$ is $CH_2CH_3$ In another embodiment, the ketone is an aromatic compound represented by formula 4 and the resultant optically active alcohol is represented formulae 6

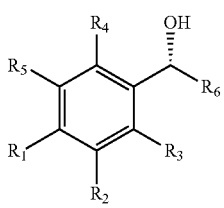

Formula 6

Wherein $R_1$=$R_2$=$R_3$=$R_4$=$R_5$=H, $CH_3$, F, Cl, Br, I, $CF_3$, $NO_2$ or $OCH_3$;
$R_6$=alkyl group such as $CH_3$ or $CH_3(CH_2)_n$ and
n=1 to 5.

The designer whole cell biocatalyst can be isolated from fermentation broth by centrifugation or filtration. The isolated biocatalyst may be used as such or as lyophilized powder. For biotransformation of carbonyl compounds to hydroxyl compounds, the biocatalyst may be suspended in a suitable buffer pH 5.0-9.0, but optimally 6.5 at temperature of 10-45° C., but optimally at 30° C. Optionally, a cosolvent such as diethyl ether, di-n-butyl ether, methyl n-butyl ether, ethyl acetate, butyl acetate etc. may be added to the reaction mixture. The contents may be energetically mixed or shaken on an orbital shaker.

In a preferred embodiment, the reaction is done by contacting the carbonyl compound with whole cell biocatalyst in phosphate buffer pH 6.5 containing di-n-butyl ether at 30° C.

In a specific embodiment, the present invention provides for a production method for producing industrially important ethyl (S)-4-chloro-3-hydroxybutyrate in about 100% enantiomeric excess, the method comprising
  (i) providing ethyl 4-chloro-3-oxobutyrate and
  (ii) contacting the ethyl 4-chloro-3-oxobutyrate with Escherichia coli strain BL21(DE3) that expresses CRS polypeptide on the surface of the cell, nicotinamide adenine dinucleotide phosphate, reduced (NADPH), glucose dehydrogenase and buffer solution to form the reaction mixture for converting ethyl 4-chloro-3-oxobutyrate to ethyl (S)-4-chloro-3-hydroxybutyrate. Optionally an organic solvent such as ethyl acetate, butyl acetate, diethylether, methyl n-butyl ether or di-n-butyl ether may be added to the reaction mixture.

In yet another specific embodiment the present invention provides for a production method for producing industrially important ethyl (S)-4-chloro-3-hydroxybutyrate in 100% enantiomeric excess and high yield via designer whole cell biocatalyzed reduction of ethyl 4-chloro-3-oxobutyrate, the method comprising
  (i) providing ethyl 4-chloro-3-oxobutyrate and
  (ii) contacting the ethyl 4-chloro-3-oxobutyrate with Escherichia coli strain BL21(DE3) that simultaneously expresses a CRS polypeptide and a GDH polypeptide on surface of cell, nicotinamide adenine dinucleotide phosphate, reduced (NADPH) and buffer solution to form the reaction mixture for converting ethyl 4-chloro-3-oxobutyrate to ethyl (S)-4-chloro-3-hydroxybutyrate. Optionally an organic solvent such as ethyl acetate, butyl acetate, diethylether, methyl n-butyl ether or di-n-butyl ether may be added to the reaction mixture.

In a preferred embodiment, the rate of conversion of ethyl 4-chloro-3-oxobutyrate to ethyl (S)-4-chloro-3-hydroxybutyrate with nicotinamide adenine dinucleotide phosphate, reduced (NADPH) as cofactor is 1.3-fold higher when Escherichia coli strain BL21(DE3) that simultaneously expresses a CRS polypeptide and a GDH polypeptide on surface of cell is replaced with Escherichia coli C41(DE3) that simultaneously expresses a CRS polypeptide and a GDH polypeptide on surface of cell.

In a preferred embodiment, the rate of conversion of ethyl 4-chloro-3-oxobutyrate to ethyl (S)-4-chloro-3-hydroxybutyrate with nicotinamide adenine dinucleotide phosphate, reduced (NADPH) as cofactor is about 1.6-fold higher with Escherichia coli strain C41(DE3) that simultaneously expresses a CRS polypeptide and a GDH polypeptide on surface of cell compared to Escherichia coli strain BL21 (DE3) that expresses only CRS polypeptide on the surface of cell, requiring addition of external GDH for cofactor recycling.

In a specific embodiment, the present invention provides for a production method for producing industrially important ethyl (S)-4-chloro-3-hydroxybutyrate in about 100% enantiomeric excess with high productivity and product accumulation of at least 150 g $l^{-1}$.

Accordingly, the main embodiment of the present invention provides a designer cell that expresses a non-naturally occurring carbonyl reductase polypeptide of sequence selected from SEQ ID NO: 1, 3, 5 or 7 of the Sequence Listing on the surface of cell having 250-fold to 300-fold higher activity per unit mass of CRS polypeptide compared to the designer cell that expresses corresponding carbonyl reductase of SEQ ID NO: 13 or 15 or 17 or 19 of the sequence listing in cytoplasm of cell for conversion of ethyl 4-chloro-3-oxobutyrate of formula 1 to ethyl (S)-4-chloro-3-hydroxybutyrate of formula 2.

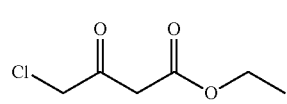

Formula 1

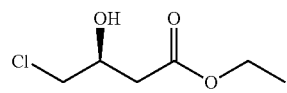

Formula 2

Another embodiment of the present invention provides a designer cell as described in the present invention that expresses a non-naturally occurring carbonyl reductase polypeptide SEQ ID NO: 1 of the Sequence Listing on the surface of cell having about 275-fold higher activity per unit mass of CRS polypeptide compared to the designer cell that expresses corresponding carbonyl reductase of SEQ ID NO: 13 of the sequence listing in cytoplasm of cell for conversion of ethyl 4-chloro-3-oxobutyrate of formula 1 to ethyl (S)-4-chloro-3-hydroxybutyrate of formula 2.

Another embodiment of the present invention provides a designer cell as described in the present invention that expresses a non-naturally occurring carbonyl reductase polypeptide of sequence selected from SEQ ID NO: 1, 3, 5 or 7 of the Sequence Listing on the surface of cell having 15-fold to 26-fold higher activity per unit cell mass compared to the designer cell that expresses corresponding carbonyl reductase of SEQ ID NO: 13 or 15 or 17 or 19 of the Sequence Listing in cytoplasm of cell for conversion of ethyl 4-chloro-3-oxobutyrate of formula 1 to ethyl (S)-4-chloro-3-hydroxybutyrate of formula 2.

Another embodiment of the present invention provides a designer cell as described in the present invention that expresses a non-naturally occurring carbonyl reductase polypeptide of SEQ ID NO: 1 of the Sequence Listing on the surface of cell having at least 15-fold higher activity per unit cell mass compared to the designer cell that expresses corresponding carbonyl reductase of SEQ ID NO: 13 of the sequence listing in cytoplasm of cell for conversion of ethyl 4-chloro-3-oxobutyrate of formula 1 to ethyl (S)-4-chloro-3-hydroxybutyrate of formula 2.

Another embodiment of the present invention provides a designer cell as described in the present invention that expresses a non-naturally occurring carbonyl reductase polypeptide of SEQ ID NO: 1 of the Sequence Listing on the surface of cell having 50-fold to 275-fold higher activity per unit mass of CRS polypeptide compared to the designer cell that expresses corresponding carbonyl reductase of SEQ ID NO: 13 of the Sequence Listing in cytoplasm of cell for reduction of compound of formula 3

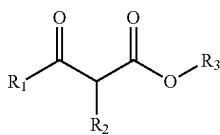

Formula 3 wherein $R_1=CH_3$, $CH_2X$, $(CH_3)_2CH$, $CF_3$ or $CH_3(CH_2)_n$
$R_2=H$, $X$ or $CH_3(CH_2)_n$;
$R_3$=alkyl group such as $CH_3$ or $CH_3(CH_2)_m$;
$X=Cl$ or $Br$;
$n=1-4$ and
$m=1-8$;

Another embodiment of the present invention provides a designer cell as described in the present invention that expresses a non-naturally occurring carbonyl reductase polypeptide of SEQ ID NO: 1 of the Sequence Listing on the surface of cell having 50-fold to 180-fold higher activity per unit mass of CRS polypeptide compared to the designer cell that expresses corresponding carbonyl reductase of SEQ ID NO: 13 of the Sequence Listing in cytoplasm of cell for reduction of compound of formula 4

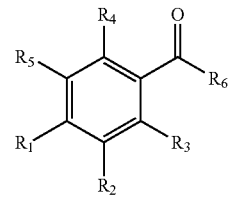

Formula 4 wherein $R_1=R_2=R_3=R_4=R_5=H$, $CH_3$, F, Cl, Br, I, $CF_3$, $NO_2$ or $OCH_3$;
$R_6$=alkyl group such as $CH_3$ or $CH_3(CH_2)_n$;
$n=1$ to 5.

Another embodiment of the present invention provides a designer cell as described in the present invention that expresses a non-naturally occurring carbonyl reductase polypeptide of SEQ ID NO: 1 of the Sequence Listing on the surface of cell having about 3-fold to 15-fold higher activity per unit cell mass compared to the designer cell that expresses corresponding carbonyl reductase of SEQ ID NO: 13 in cytoplasm of cell for reduction of compound of formula 3 or compound of formula 4

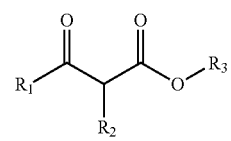

Formula 3 wherein $R_1=CH_3$, $CH_2X$, $(CH_3)_2CH$, $CF_3$ or $CH_3(CH_2)_n$
$R_2=H$, $X$ or $CH_3(CH_2)_n$;
$R_3$=alkyl group such as $CH_3$ or $CH_3(CH_2)_m$;
$X=Cl$ or $Br$;
$n=1-4$ and
$m=1-8$;

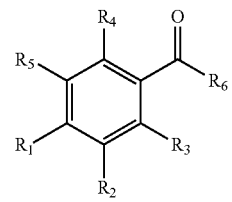

Formula 4 wherein $R_1=R_2=R_3=R_4=R_5=H$, $CH_3$, F, Cl, Br, I, $CF_3$, $NO_2$ or $OCH_3$;
$R_6$=alkyl group such as $CH_3$ or $CH_3(CH_2)_n$;
$n=1$ to 5.

Another embodiment of the present invention provides a designer cell as described in the present invention that simultaneously expresses a non-naturally occurring CRS polypeptide of sequence selected from SEQ ID NO: 1, 3, 5 or 7 and a non-naturally occurring GDH polypeptide of sequence selected from SEQ ID NO: 9 or 11 of the Sequence Listing on the surface of cell that has 250-fold to 300-fold higher activity for conversion of ethyl 4-chloro-3-oxobutyrate of formula 1 to ethyl (S)-4-chloro-3-hydroxybutyrate of formula 2 per unit mass of CRS polypeptide and 200-fold to 250-fold enhanced activity for oxidation of glucose to gluconate per unit mass of GDH polypeptide compared to the designer cell that simultaneously expresses corresponding CRS of SEQ ID NO: 13 or 15 or 17 or 19 of the Sequence Listing and corresponding GDH of SEQ ID NO: 21 or 23 of the Sequence Listing in cytoplasm of cell.

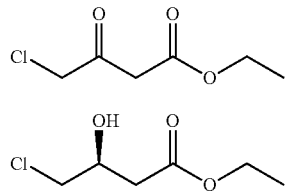

Formula 1

Formula 2

Another embodiment of the present invention provides a designer cell as described in the present invention that simultaneously expresses a non-naturally occurring CRS polypeptide SEQ ID NO: 1 and a non-naturally occurring GDH polypeptide SEQ ID NO: 9 of the Sequence Listing on the surface of cell that has about 270-fold higher activity for conversion of ethyl 4-chloro-3-oxobutyrate of formula 1 to ethyl (S)-4-chloro-3-hydroxybutyrate of formula 2 per unit mass of CRS polypeptide and about 225-fold enhanced activity for oxidation of glucose to gluconate per unit mass of GDH polypeptide compared to the designer cell that simultaneously expresses corresponding CRS of SEQ ID NO: 13 of the Sequence Listing and corresponding GDH of SEQ ID NO: 21 of the Sequence Listing in cytoplasm of cell.

Another embodiment of the present invention provides a designer cell as described in the present invention that simultaneously expresses a non-naturally occurring CRS polypeptide of sequence selected from SEQ ID NO: 1, 3, 5 or 7 and a non-naturally occurring GDH polypeptide of sequence selected from SEQ ID NO: 9, 11, 13 or 15 of the Sequence Listing on the surface of cell that has about 11-fold to 24-fold higher activity for conversion of ethyl 4-chloro-3-oxobutyrate of formula 1 to ethyl (S)-4-chloro-3-hydroxybutyrate of formula 2 per unit cell mass and 9-fold to 31-fold enhanced activity for oxidation of glucose to gluconate per unit cell mass compared to the designer cell that simultaneously expresses corresponding CRS of SEQ ID NO: 13 or 15 or 17 or 19 of the Sequence Listing and corresponding GDH of SEQ ID NO: 21 or 23 of the Sequence Listing in cytoplasm of cell.

Another embodiment of the present invention provides a designer cell as described in the present invention that simultaneously expresses a non-naturally occurring CRS polypeptide of SEQ ID NO: 1 and a non-naturally occurring GDH polypeptide of SEQ ID NO: 9 of the Sequence Listing on the surface of cell that has about 24-fold higher activity for conversion of ethyl 4-chloro-3-oxobutyrate of formula 1 to ethyl 4-chloro-3-hydroxybutyrate of formula 2 per unit cell mass and about 31-fold enhanced activity for oxidation of glucose to gluconate per unit cell mass compared to the designer cell that simultaneously expresses corresponding CRS of SEQ ID NO: 13 of the Sequence Listing and corresponding GDH of SEQ ID NO: 21 of the Sequence Listing in cytoplasm of cell.

Another embodiment of the present invention provides a designer cell as described in the present invention that simultaneously expresses a non-naturally occurring CRS polypeptide of SEQ ID NO: 1 and a non-naturally occurring GDH polypeptide of SEQ ID NO: 9 of the Sequence Listing on the surface of cell having about 55-fold to 270-fold higher activity per unit mass of CRS polypeptide compared to the designer cell that simultaneously expresses corresponding CRS of SEQ ID NO: 13 of the Sequence Listing and corresponding GDH of SEQ ID NO: 21 of the Sequence Listing in cytoplasm of cell for reduction of compound of formula 3

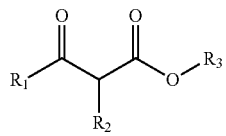

Formula 3 wherein $R_1$=$CH_3$, $CH_2X$, $(CH_3)_2CH$, $CF_3$ or $CH_3(CH_2)_n$ $R_2$=H, X or $CH_3(CH_2)_n$;

$R_3$=alkyl group such as $CH_3$ or $CH_3(CH_2)_m$;

X=Cl or Br;

n=1-4 and m=1-8

Another embodiment of the present invention provides a designer cell as described in the present invention that simultaneously expresses a non-naturally occurring CRS polypeptide of SEQ ID NO: 1 and a non-naturally occurring GDH polypeptide of SEQ ID NO: 9 of the Sequence Listing on the surface of cell having about 40-fold to 156-fold higher activity per unit mass of CRS polypeptide compared to the designer cell that simultaneously expresses corresponding CRS of SEQ ID NO: 13 of the Sequence Listing and corresponding GDH of SEQ ID NO: 21 of the Sequence Listing in cytoplasm of cell for reduction of compound of formula 4

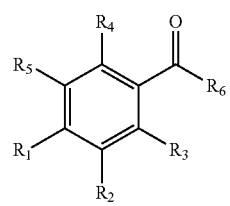

Formula 4 wherein $R_1$=$R_2$=$R_3$=$R_4$=$R_5$=H, $CH_3$, F, Cl, Br, I, $CF_3$, $NO_2$ or $OCH_3$;

$R_6$=alkyl group such as $CH_3$ or $CH_3(CH_2)_n$;

n=1 to 5.

Another embodiment of the present invention provides a designer cell as described in the present invention that simultaneously expresses a non-naturally occurring CRS polypeptide of SEQ ID NO: 1 and a non-naturally occurring GDH polypeptide of SEQ ID NO: 9 of the Sequence Listing on the surface of cell having about 3-fold to 24-fold higher activity per unit cell mass compared to the designer cell that simultaneously expresses corresponding CRS of SEQ ID NO: 13 of the Sequence Listing and corresponding GDH of SEQ ID NO: 21 of the Sequence Listing in cytoplasm of cell for reduction of compound of compound of formula 3 or compound of formula 4

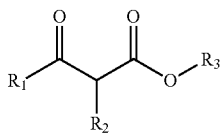

Formula 3 wherein $R_1$=CH$_3$, CH$_2$X, (CH$_3$)$_2$CH, CF$_3$ or CH$_3$(CH$_2$)$_n$;
$R_2$=H, X or CH$_3$(CH$_2$)$_n$;
$R_3$=alkyl group such as CH$_3$ or CH$_3$(CH$_2$)$_m$;
X=Cl or Br;
n=1-4 and
m=1-8

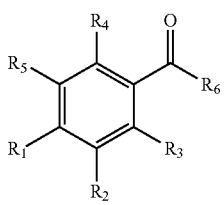

Formula 4 wherein $R_1$=$R_2$=$R_3$=$R_4$=$R_5$=H, CH$_3$, F, Cl, Br, I, CF$_3$, NO$_2$ or OCH$_3$;
$R_6$=alkyl group such as CH$_3$ or CH$_3$(CH$_2$)$_n$;
n=1 to 5.

Another embodiment of the present invention provides a designer cell as described in the present invention, wherein designer cell is recombinant *Escherichia coli* BL21(DE3) or recombinant *Escherichia coli* C41(DE3) or recombinant *Escherichia coli* C43(DE3).

Yet another embodiment of the present invention provides a recombinant expression vector comprising polynucleotide encoding the polypeptide having the amino acid sequence of SEQ ID NO 1 or 3 or 5 or 7 showing carbonyl reductase activity.

Yet another embodiment of the present invention provides a recombinant expression vector comprising polynucleotides encoding the polypeptide having the amino acid sequence of SEQ ID NO 1 or 3 or 5 or 7 showing carbonyl reductase activity and the polypeptide having the amino acid sequence of SEQ ID NO 9 or 11 showing GDH activity.

Yet another embodiment of the present invention provides a use of the designer cell as described in the present invention for the production of ethyl (S)-4-chloro-3-hydroxybutyrate of formula 2 in about 100% enantiomeric excess

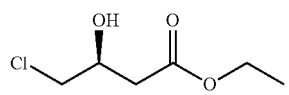

Formula 2

Yet another embodiment of the present invention provides a use of the designer cell as claimed in claim 8 for the production of ethyl (S)-4-chloro-3-hydroxybutyrate of formula 2 in about 100% enantiomeric excess Yet another embodiment of the present invention provides a use of the designer cell as described in the present invention for the production of compound of formula 5

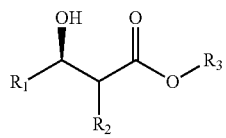

Formula 5 wherein $R_1$=CH$_3$, CH$_2$X, (CH$_3$)$_2$CH, CF$_3$ or CH$_3$(CH$_2$)$_n$;
$R_2$=H, X or CH$_3$(CH$_2$)$_n$;
$R_3$=alkyl group such as CH$_3$ or CH$_3$(CH$_2$)$_m$;
X=Cl or Br;
n=1-4 and
m=1-8

Yet another embodiment of the present invention provides use of the designer cell as described in the present invention for the production of compound of formula 5

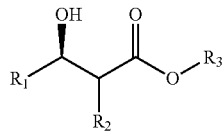

Formula 5 wherein $R_1$=CH$_3$, CH$_2$X, (CH$_3$)$_2$CH, CF$_3$ or CH$_3$(CH$_2$)$_n$;
$R_2$=H, X or CH$_3$(CH$_2$)$_n$;
$R_3$=alkyl group such as CH$_3$ or CH$_3$(CH$_2$)$_m$;
X=Cl or Br;
n=1-4 and
m=1-8

Yet another embodiment of the present invention provides use of the designer cell as described in the present invention for the production of compound of formula 6

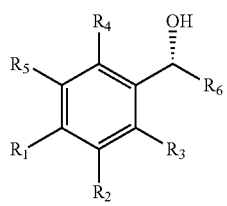

Formula 6 wherein $R_1$=$R_2$=$R_3$=$R_4$=$R_5$=H, CH$_3$, F, Cl, Br, I, CF$_3$, NO$_2$ or OCH$_3$;
$R_6$=alkyl group such as CH$_3$ or CH$_3$(CH$_2$)$_n$;
n=1 to 5.

Yet another embodiment of the present invention provides use of designer cell as described in the present invention for the production of compound of formula 6

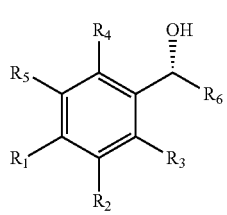

Formula 6 wherein $R_1=R_2=R_3=R_4=R_5=$H, $CH_3$, F, Cl, Br, I, $CF_3$, $NO_2$ or $OCH_3$;

$R_6=$alkyl group such as $CH_3$ or $CH_3(CH_2)_n$;

n=1 to 5.

Another embodiment of the present invention provides for designer cells having Accession No. MTCC No. 5806, MTCC No. 5807, MTCC No. 5808 and MTCC No. 5809, wherein the designer cells comprise of nucleotide sequences having SEQ ID Nos. 2, 4, 6 and 8 and wherein the nucleotide sequences having SEQ ID Nos. 2, 4, 6 and 8 are capable of expressing amino acid sequences having SEQ ID Nos. 1, 3, 5 and 7.

Another embodiment of the present invention provides for designer cells having Accession No. MTCC No. 5810, MTCC No. 5811, MTCC No. 5812, MTCC No. 5813; MTCC No. 5814. MTCC No. 5815, MTCC No. 5816 and MTCC No. 5817, wherein MTCC No. 5810 comprise of nucleotide sequences having SEQ ID NO. 2 and SEQ ID NO.10; wherein designer cells having accession no. having MTCC No. 5811 comprise of nucleotide sequences having SEQ ID NO. 2 and SEQ ID NO.12; wherein designer cells having accession no. having MTCC No. 5812 comprise of nucleotide sequences having SEQ ID NO. 4 and SEQ ID NO.10; wherein designer cells having accession no. having MTCC No. 5813 comprise of nucleotide sequences having SEQ ID NO. 4 and SEQ ID NO.12; wherein designer cells having accession no. having MTCC No. 5814 comprise of nucleotide having SEQ ID NO. 6 and SEQ ID NO.10; wherein designer cells having accession no. having MTCC No. 5815 comprise of nucleotide sequences having SEQ ID NO. 6 and SEQ ID NO.12; wherein designer cells having accession no. having MTCC No. 5816 comprise of nucleotide sequences having SEQ ID NO. 8 and SEQ ID NO.10; wherein designer cells having accession no. having MTCC No. 5817 comprise of nucleotide sequences having SEQ ID NO. 8 and SEQ ID NO.12 and that wherein designer cells having accession no. having MTCC No. 5810 is capable of expressing amino acid sequences having SEQ ID NO. 1 and SEQ ID NO. 9; wherein designer cells having accession no. having MTCC No. 5811 is capable of expressing amino acid sequences having SEQ ID NO. 1 and SEQ ID NO.11; wherein designer cells having accession no. having MTCC No. 5812 is capable of expressing amino acid sequences having SEQ ID NO. 3 and SEQ ID NO. 9; wherein designer cells having accession no. having MTCC No. 5813 is capable of expressing amino acid sequences having SEQ ID NO. 3 and SEQ ID NO.11; wherein designer cells having accession no. having MTCC No. 5814 is capable of expressing amino acid sequences having SEQ ID NO. 5 and SEQ ID NO.9; wherein designer cells having accession no. having MTCC No. 5815 is capable of expressing amino acid sequences having SEQ ID NO. 5 and SEQ ID NO.11; wherein designer cells having accession no. having MTCC No. 5816 is capable of expressing amino acid sequences having SEQ ID NO. 7 and SEQ ID NO.9; wherein designer cells having accession no. having MTCC No. 5817 is capable of expressing amino acid sequences having SEQ ID NO. 7 and SEQ ID NO.11.

Another embodiment of the present invention provides a process for production of ethyl (S)-4-chloro-3-hydroxybutyrate of formula 2 in about 100% enantiomeric excess, Formula 2

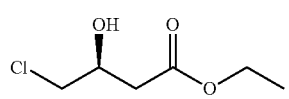

and the said process comprising the steps of a. providing ethyl 4-chloro-3-oxobutyrate of formula 1;

Formula 1

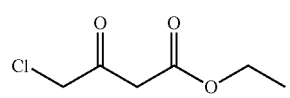

b. contacting the ethyl 4-chloro-3-oxobutyrate with designer cell as described in the present invention and 0.005 to 0.02 mol % nicotinamide adenine dinucleotide phosphate, reduced (NADPH) and 100 to 500 units glucose dehydrogenase and a buffer solution of pH 5.0 to 9.0;

c. adding to the reaction mixture obtained in step (b) an organic solvent such as ethyl acetate, butyl acetate, diethylether, methyl n-butyl ether or di-n-butyl ether in the ratio ranging between 10:1 to 1:1;

d. energetically mixing the reaction mixture on magnetic stirrer at constant temperature of 20 to 40° C.;

e. extracting the product obtained in step (d) in ethyl acetate followed by isolating the product ethyl (S)-4-chloro-3-hydroxybutyrate.

Another embodiment of the present invention provides for a process as described in the present invention wherein pH is preferably 6.5.

Another embodiment of the present invention provides for a process as described in the present invention wherein temperature is preferably 30° C.

Another embodiment of the present invention provides for a process as described in the present invention wherein organic solvent is preferably di-n-butyl ether.

Another embodiment of the present invention provides for a process as described in the present invention wherein designer cell is a strain of recombinant *Escherichia coli* selected from recombinant *Escherichia coli* BL21(DE3), recombinant *Escherichia coli* C41(DE3) and recombinant *Escherichia coli* C43(DE3).

Another embodiment of the present invention provides for a process as described in the present invention wherein designer cell is preferably recombinant *Escherichia coli* C41(DE3).

Another embodiment of the present invention provides for a process for the production of optically enriched aliphatic alcohols of formula 5 as described in the present invention:

Formula 5

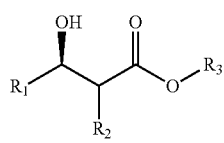

wherein $R_1=CH_3$, $CH_2X$, $(CH_3)_2CH$, $CF_3$ or $CH_3(CH_2)_n$;

$R_2=$H, X or $CH_3(CH_2)_n$;

$R_3=$alkyl group such as $CH_3$ or $CH_3(CH_2)_m$;

X=Cl or Br;

n=1-4 and m=1-8 and the said process comprising the steps of;

a. providing a ketone of formula 3

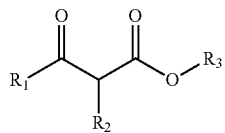

Formula 3 wherein $R_1$=$CH_3$, $CH_2X$, $(CH_3)_2CH$, $CF_3$ or $CH_3(CH_2)_n$;
$R_2$=H, X or $CH_3(CH_2)_n$;
$R_3$=alkyl group such as $CH_3$ or $CH_3(CH_2)_m$;
X=Cl or Br;
n=1-4 and
m=1-8 b. contacting the ketone of formula 3 as provided in step (a) with designer cell as described in the present invention and 0.005 to 0.02 mol % nicotinamide adenine dinucleotide phosphate, reduced (NADPH) and 100 to 500 units glucose dehydrogenase and buffer solution of pH 5.0 to 9.0 to form the reaction mixture;
c. adding to the reaction mixture obtained in step (b) an organic solvent such as ethyl acetate, butyl acetate, diethylether, methyl n-butyl ether or di-n-butyl ether in the ratio ranging between 10:1 to 1:1;
d. energetically mixing the reaction mixture on magnetic stirrer at constant temperature of 20 to 40° C.;
e. extracting the product obtained in step (d) in ethyl acetate followed by isolating the compound of formula 5.

Another embodiment of the present invention provides for a process as described in the present invention wherein pH is preferably 6.5.

Another embodiment of the present invention provides for a process as described in the present invention wherein temperature is preferably 30° C.

Another embodiment of the present invention provides for a process as described in the present invention wherein organic solvent is preferably di-n-butyl ether.

Another embodiment of the present invention provides for a process as described in the present invention wherein designer cell is a strain of recombinant *Escherichia coli* selected from recombinant *Escherichia coli* BL21(DE3), recombinant *Escherichia coli* C41(DE3) and recombinant *Escherichia coli* C43(DE3).

Another embodiment of the present invention provides for a process as described in the present invention wherein designer cell is preferably recombinant *Escherichia coli* C41(DE3).

Another embodiment of the present invention provides for a process for production of optically enriched aryl alcohols of formula 6 as described in the present invention:

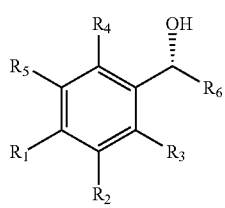

Formula 6 wherein $R_1$=$R_2$=$R_3$=$R_4$=$R_5$=H, $CH_3$, F, Cl, Br, I, $CF_3$, $NO_2$ or $OCH_3$;
$R_6$=alkyl group such as $CH_3$ or $CH_3(CH_2)_n$;
n=1 to 5.
and the said process comprising the steps of;
a. providing a ketone of formula 4

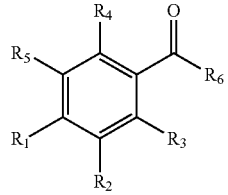

Formula 4

Wherein $R_1$=$R_2$=$R_3$=$R_4$=$R_5$=H, $CH_3$, F, Cl, Br, I, $CF_3$, $NO_2$ or $OCH_3$;
$R_6$=alkyl group such as $CH_3$ or $CH_3(CH_2)_n$;
n=1 to 5.

b. contacting the ketone of formula 3 as provided in step (a) with designer cell as described in the present invention and 0.005 to 0.02 mol % nicotinamide adenine dinucleotide phosphate, reduced (NADPH) and 100 to 500 units glucose dehydrogenase and buffer solution of pH 5.0 to 9.0 to form the reaction mixture;
c. adding to the reaction mixture obtained in step (b) an organic solvent such as ethyl acetate, butyl acetate, diethylether, methyl n-butyl ether or di-n-butyl ether in the ratio ranging between 10:1 to 1:1;
d. energetically mixing the reaction mixture on magnetic stirrer at constant temperature of 20 to 40° C.;
e. extracting the product obtained in step (d) in ethyl acetate followed by isolating the compound of formula 6.

Another embodiment of the present invention provides for a process as described in the present invention wherein pH is preferably 6.5.

Another embodiment of the present invention provides, for a process as described in the present invention wherein temperature is preferably 30° C.

Another embodiment of the present invention provides for a process as described in the present invention wherein organic solvent is preferably di-n-butyl ether.

Another embodiment of the present invention provides for a process as described in the present invention wherein designer cell is a strain of recombinant *Escherichia coli* selected from recombinant *Escherichia coli* BL21(DE3), recombinant *Escherichia coli* C41(DE3) and recombinant *Escherichia coli* C43(DE3).

Another embodiment of the present invention provides for a process as described in the present invention wherein designer cell is preferably recombinant *Escherichia coli* C41(DE3).

Another embodiment of the present invention provides for designer cells having Accession No. MTCC No. 5806, MTCC No. 5807, MTCC No. 5808 and MTCC No. 5809.

Yet another embodiment of the present invention provides for designer cells wherein the designer cell having Accession Nos. MTCC 5806-5809 expressing amino acid sequences having SEQ ID No. 1, 3, 5 and 7.

Yet another embodiment of the present invention provides for designer cells as described in the present invention wherein the amino acid sequences having SEQ ID Nos. 1, 3, 5, 7 correspond to nucleotide sequences having SEQ ID No. 2, 4, 6 and 8.

Yet another embodiment of the present invention provides for designer cells, wherein the SEQ ID Nos. 1-8, are non-naturally occurring sequences of carbony reductase enzyme.

Yet another embodiment of the present invention provides for designer cells capable of expressing high activity of carbonyl reductase on the cell surface.

Yet another embodiment of the present invention provides for a recombinant vector construct comprising and capable of expressing SEQ ID Nos. 1-8.

Yet another embodiment of the present invention provides for a recombinant vector construct comprising non-naturally occurring sequences of carbony reductase enzyme.

Yet another embodiment of the present invention provides for a recombinant vector construct as described in the present invention capable of expressing high activity of carbonyl reductase on the cell surface.

Yet another embodiment of the present invention provides for designer cells having Accession No. MTCC No. 5810, MTCC No. 5811, MTCC No. 5812, MTCC No. 5813; MTCC No. 5814. MTCC No. 5815, MTCC No. 5816 and MTCC No. 5817.

Yet another embodiment of the present invention provides for designer cells as, wherein designer cells having accession no. having MTCC No. 5810 expressing amino acid sequences having SEQ ID NO. 1 and SEQ ID NO.9; wherein designer cells having accession no. having MTCC No. 5811 expressing amino acid sequences having SEQ ID NO. 1 and SEQ ID NO.11; wherein designer cells having accession no. having MTCC No. 5812 expressing amino acid sequences having SEQ ID NO. 3 and SEQ ID NO. 9; wherein designer cells having accession no. having MTCC No. 5813 expressing amino acid sequences having SEQ ID NO. 3 and SEQ ID NO.11; wherein designer cells having accession no. having MTCC No. 5814 expressing amino acid sequences having SEQ ID NO. 5 and SEQ ID NO.9; wherein designer cells having accession no. having MTCC No. 5815 expressing amino acid sequences having SEQ ID NO. 5 and SEQ ID NO.11; wherein designer cells having accession no. having MTCC No. 5816 expressing amino acid sequences having SEQ ID NO. 7 and SEQ ID NO.9; wherein designer cells having accession no. having MTCC No. 5817 expressing amino acid sequences having SEQ ID NO. 7 and SEQ ID NO.11.

Yet another embodiment of the present invention provides for designer cells wherein the amino acid sequences having SEQ ID Nos. 1, 3, 5, 7, 9 and 11 correspond to nucleotide sequences having SEQ ID Nos. 2, 4, 6, 8, 10 and 12.

Yet another embodiment of the present invention provides for designer cells, capable of co-expressing enzyme carbonyl reductase and gluconase dehydrogenase together on cell surface.

Yet another embodiment of the present invention provides for a recombinant vector comprising and capable of expressing amino acid sequences having SEQ ID Nos. 1, 3, 5, 7, 9 and 11 and nucleotide sequences having SEQ ID Nos. 2, 4, 6, 8, 10 and 12.

Another embodiment of the present invention provides for a recombinant vector as described in the present invention capable of co-expressing enzyme carbonyl reductase and gluconase dehydrogenase together on cell surface.

Another embodiment of the present invention provides for a method of producing compound of Formula 5 or Formula 6 or Formula 2 such as herein described in the present invention said method comprising (a) providing as ketone having a formula 3 such as herein described in the present invention; (b) contacting the ketone of formula 3 of step (a) with a designer cell such as herein described in the present invention comprising SEQ ID Nos. 1-12 alone or in combination such as herein described in the present invention and 0.005 to 0.02 mol % nicotinamide adenine dinucleotide phosphate, reduced (NADPH) optionally, if required, adding 100 to 500 units glucose dehydrogenase and buffer solution of pH 5.0 to 9.0 to form the reaction mixture; (c) adding to the reaction mixture obtained in step (b) an organic solvent such as ethyl acetate, butyl acetate, diethylether, methyl n-butyl ether or di-n-butyl ether in the ratio ranging between 10:1 to 1:1; (d) energetically mixing the reaction mixture on magnetic stirrer at constant temperature of 20 to 40° C. and extracting the product obtained in step (d) in ethyl acetate followed by isolating the compound of Formula 5 or Formula 6 or Formula 2

Advantages of the Invention

1. The invention provides a whole cell biocatalyst that has at least 250-fold improved conversion rate per unit mass of CRS compared to prior art biocatalyst for conversion of ethyl 4-chloro-3-oxobutyrate to industrially important ethyl (S)-4-chloro-3-hydroxybutyrate.
2. The invention provides a whole cell biocatalyst that has higher efficiency with respect to cofactor loading due to presence of both reductase and coenzyme regenerating activities on the surface of same cell. In such a system the cofactor nicotinamide adenine dinucleotide phosphate, reduced (NADPH)/nicotinamide adenine dinucleotide phosphate (NADP) gets channelized between CRS and GDH enzymes which are localized in close proximity on the surface of cells.
3. Enantiomerically enriched alcohols are produced at significantly higher conversion rate. More specifically, ethyl (S)-4-chloro-3-hydroxybutyrate is produced at significantly higher conversion rate in about 100% enantiomeric excess with product accumulation of at least 150 g l$^{-1}$, which is useful as chiral building block and an intermediate for the production of hydroxymethylglutaryl-CoA (HMG-CoA) reductase inhibitors.

Plasmid/s and Transformant/s

Expression plasmid of the present invention includes pET23(a)-omp-CRS having the DNA sequence represented by SEQ ID NO: 2 or 4 or 6 or 8 of Sequence listing encoding the polypeptide having the amino acid sequence represented by SEQ ID NO 1 or 3 or 5 or 7 showing carbonyl reductase activity.

Expression plasmid of the present invention includes pETDuet1-omp-CRS; omp-GDH having the DNA sequences represented by SEQ ID NO 2 or 4 or 6 or 8 encoding the CRS polypeptide having the amino acid sequence represented by SEQ ID NO 1 or 3 or 5 or 7 showing carbonyl reductase activity and SEQ ID NO 10 or 12 encoding the GDH polypeptide having the amino acid sequence represented by SEQ ID NO 9 or 11 showing GDH activity.

The plasmid containing the DNA of the present invention can be introduced into a chemically competent host cell by a known method. *Escherichia coli* DH5α were used as a cloning host and *Escherichia coli* BL21(DE3); *Escherichia coli* C41(DE3) and *Escherichia coli* C43(DE3) as expression host.

As an example of a transformant according to the present invention, mention may be made of *Escherichia coli* BL21 (DE3)+pET23(a)-omp-CRS.

More significantly, as an example of a transformant according to the present invention, mention may be made of *Escherichia coli* C41(DE3)+pET23(a)-omp-CRS.

Transformant/s Having Carbonyl Reductase Activity

When a transformant having carbonyl reductase activity reacted with the carbonyl group of the substrate including ethyl 4-chloro-3-oxobutyrate and a coenzyme nicotinamide adenine dinucleotide phosphate, reduced (NADPH), it asymmetrically reduces the compound having the carbonyl group including ethyl 4-chloro-3-oxobutyrate to produce an optically pure corresponding alcohols including ethyl (S)-4-chloro-3-hydroxybutyrate. Transformant/s of the present invention mentioned above having expression plasmid pET23(a)-omp-CRS and pETDuet1-omp-CRS; omp-GDH exhibit carbonyl reductase activity. More precisely, transformant/s of the present invention mentioned above having expression plasmid pET23(a)-omp-CRS and pETDuet1-omp-CRS; omp-GDH expressed polypeptide having carbonyl reductase activity on the surface of the cell.

Transformant Having Both Carbonyl Reductase and Coenzyme Regeneration Activity

Transformant of the present invention mentioned above having both CRS and GDH expression plasmid together i.e. pETDuet1-omp-CRS; omp-GDH exhibits both carbonyl reductase and coenzyme regeneration activity. More precisely, transformant/s of the present invention mentioned above having expression plasmid pETDuet1-omp-CRS; omp-GDH expressed polypeptides having both carbonyl reductase and coenzyme regeneration activity on the surface of the cell.

Strain Designation and Deposit Details

The synthesized recombinant *Escherichia coli* strains expressing "CRS polypeptide" and "GDH polypeptide" have been deposited with The International Depository Authority, Microbial Type Culture Collection and Gene Bank (MTCC), Institute of Microbial Technology, Sector 39A, Chandigarh 160036, India. The strain designation and assigned accession number are given below. The strains MTCC 5806, 5807, 5808 and 5809 express "CRS polypeptide" SEQ ID No. 1, 3, 5 and 7, respectively. The strains MTCC 5810 to 5817 co-express "CRS polypeptide" SEQ ID No. 1, 3, 5 and 7 and "GDH polypeptide" SEQ ID No. 9 and 11. In the description, the amino acid sequence has been assigned odd number. The nucleotide sequence coding for a particular amino acid has been assigned immediately next even number. For example, for amino acid sequence SEQ ID NO: 1, the corresponding coding nucleotide sequence has been assigned sequence SEQ ID NO: 2.

| S. No. | Strain | MTCC No. |
|---|---|---|
| 1 | *E. coli* BL21(DE3) + pET 23(a)-omp-CRS (SEQ ID 2) | MTCC 5806 |
| 2 | *E. coli* BL21(DE3) + pET 23(a)-omp-CRS (SEQ ID 4) | MTCC 5807 |
| 3 | *E. coli* BL21(DE3) + pET 23(a)-omp-CRS (SEQ ID 6) | MTCC 5808 |
| 4 | *E. coli* BL21(DE3) + pET 23(a)-omp-CRS (SEQ ID 8) | MTCC 5809 |
| 5 | *E. coli* BL21(DE3) + pET Duet1-omp-CRS, omp-GDH (SEQ ID 2 + 10) | MTCC 5810 |
| 6 | *E. coli* BL21(DE3) + pET Duet1-omp-CRS, omp-GDH (SEQ ID 2 + 12) | MTCC 5811 |
| 7 | *E. coli* BL21(DE3) + pET Duet1-omp-CRS, omp-GDH (SEQ ID 4 + 10) | MTCC 5812 |
| 8 | *E. coli* BL21(DE3) + pET Duet1-omp-CRS, omp-GDH (SEQ ID 4 + 12) | MTCC 5813 |
| 9 | *E. coli* BL21(DE3) + pET Duet1-omp-CRS, omp-GDH (SEQ ID 6 + 10) | MTCC 5814 |
| 10 | *E. coli* BL21(DE3) + pET Duet1-omp-CRS, omp-GDH (SEQ ID 6 + 12) | MTCC 5815 |
| 11 | *E. coli* BL21(DE3) + pET Duet1-omp-CRS, omp-GDH (SEQ ID 8 + 10) | MTCC 5816 |
| 12 | *E. coli* BL21(DE3) + pET Duet1-omp-CRS, omp-GDH (SEQ ID 8 + 12) | MTCC 5817 |

Demonstration of the Expression of CRS on the Surface of *Escherichia coli*

The recombinant cells expressing CRS were lysed, cell debris was removed by centrifugation and the supernatant was then subjected to ultra-centrifugation at 1,00,000 g for 2 hr at 4° C. for separation of membrane fraction and soluble fraction. The sediment containing the membrane fraction was washed with buffer and re-suspended in membrane solubilization buffer (25 mM Tris HCl, 20% Glycerol and 2% Triton X100, pH 7.5). All the three fractions, cell-free extract, membrane fraction and soluble protein fraction were assayed for activity using ethyl 4-chloro-3-hydroxybutyrate as substrate. Most of the activity was recovered from membrane fraction.

The presence of CRS on the surface of *Escherichia coli* cells was further confirmed by EM immunogold labeling studies carried out with ultrathin sections of *Escherichia coli*. Anti-CRS polyclonal antibody was raised against the purified CRS in rabbit and was assayed for their specificity by Western blotting. The purified CRS was run on SDS-PAGE under the reducing conditions and after electroblotting on to nitrocellulose membrane was probed with rabbit anti-CRS polyclonal antibody which was further probed with alkaline phosphatase conjugated goat anti-rabbit IgG (whole molecule) secondary antibody. The blot was then developed by dipping it in the substrate solution containing 5-bromo-4-chloro-3-indolyl phosphate (BCIP, 0.15 mg/ml), nitro blue tetrazolium (NBT, 0.30 mg/ml), Tris HCl (100 mM) and $MgCl_2$ (5 mM), pH 9.5 for 10 minute. The polyclonal antibody that specifically labeled pure CRS was also able to specifically label omp-CRS.

After several dehydration steps, *Escherichia coli* cells were embedded in LR white resin, which was then dehydrated in several steps using 0.2% glutaraldehyde as fixative. Thin sections cut using an ultramicrotome were incubated with rabbit anti-CRS polyclonal antibody followed by nano-gold-labeled goat anti-rabbit IgG (whole molecule) secondary antibody and visualized under the transmission electron microscope. Different fields were observed and the gold particles were found to be exclusively present on the surface of the cells (FIG. 7). No labeling occurred with cells as the negative control.

Use of Transformant/s

When a transformant, of the present invention, containing DNA encoding the polypeptide having the carbonyl reductase activity is used, an optically pure alcohol can be produced. Furthermore, if the transformant, having the expression plasmid pET23(a)-omp-CRS expressing the polypeptide having carbonyl reductase activity is used, an optically pure alcohol can be produced. When a transformant having the expression vector pETDuet1-omp-CRS; omp-GDH expressing the polypeptides having carbonyl reductase activity and coenzyme regeneration activity are used, an optically pure alcohol can be produced. In particular, when a transformant having the expression vector pETDuet1-omp-CRS; omp-GDH expressing polypeptides having carbonyl reductase activity and coenzyme regeneration activity is used, an optically active alcohol can be produced more effectively.

The transformant containing both DNA encoding the polypeptide having carbonyl reductase activity of the present invention and DNA encoding the polypeptide having coenzyme regeneration ability can be obtained by introducing both DNA encoding the polypeptide having carbonyl reductase activity, of the present invention and DNA encoding the polypeptide having the coenzyme regeneration ability into the single vector.

As an example of a vector into which both DNA encoding the polypeptide having the carbonyl reductase activity and DNA encoding a polypeptide having the coenzyme regeneration ability are introduced, mention may be made of pETDuet1-omp-CRS; omp-GDH.

Further, as an example of a transformant containing both DNA encoding the polypeptide having carbonyl reductase activity and the DNA encoding a polypeptide having a coenzyme regeneration ability, mention may be made *Escherichia coli* BL21(DE3)+pETDuet1-omp-CRS; omp-GDH obtained by transforming *Escherichia coli* BL21(DE3) with the vector.

Furthermore, as an example of a transformant containing both DNA encoding the polypeptide having carbonyl reductase activity and the DNA encoding a polypeptide having a coenzyme regeneration ability, mention may be made *Escherichia coli* C41(DE3)+pETDuet1-omp-CRS; omp-GDH obtained by transforming *Escherichia coli* C43(DE3) with the vector.

Culturing a transformant containing DNA encoding the polypeptide having carbonyl reductase activity and a transformant containing both DNA encoding the polypeptide having carbonyl reductase activity and the DNA encoding a polypeptide having a coenzyme regeneration ability can be performed in a liquid nutrition medium generally used and containing a carbon source, nitrogen source, inorganic salts and organic nutrients, etc., as long as they are proliferated.

Assay Methods for Enzyme Activity

The activity of the transformant expressing polypeptide having a carbonyl reductase activity can be measured by a conventional method. For example, the activity of the carbonyl reductase can be obtained in which 1 ml of reaction mixture in 50 mM phosphate buffer, pH 6.5 contains 2 mM ECAA, 0.2 mM nicotinamide adenine dinucleotide phosphate, reduced (NADPH) and 5-20 µl of the whole cell biocatalyst or 5-10 µg of purified protein or $10^6$-$10^7$ whole cell biocatalyst and the reaction were monitored spectrophotometrically for 15 to 60 min at 340 nm (molar absorption coefficient of 6.22 $mM^{-1}cm^{-1}$) for the oxidation of nicotinamide adenine dinucleotide phosphate, reduced (NADPH).

The activity of the transformant expressing polypeptide having a coenzyme regeneration activity can be measured by a conventional method. For example, the activity of the glucose dehydrogenase can be obtained in which 1 ml of reaction mixture in 100 mM tris-HCl buffer, pH 8.0 contains 10 mM glucose, 0.5 mM nicotinamide adenine dinucleotide phosphate (NADP) and 5-20 µl of the whole cell biocatalyst or 5-10 µg of purified protein or $10^6$-$10^7$ whole cell biocatalyst and the reaction were monitored spectrophotometrically for 15 to 60 min at 340 nm (molar absorption coefficient of 6.22 $mM^{-1}cm^{-1}$) for the reduction of nicotinamide adenine dinucleotide phosphate (NADP).

Production of Optically Active Alcohols

Production of an optically active alcohols using either transformant having the carbonyl reductase activity and commercially available glucose dehydrogenase or transformant having both the carbonyl reductase activity and coenzyme regeneration activity can be performed by adding a compound containing carbonyl group serving as a substrate including ethyl 4-chloro-3-oxobutyrate, a coenzyme nicotinamide adenine dinucleotide phosphate (NADP) and glucose to an appropriate solvent, and stirring the mixture while adjusting the pH.

The reaction may be performed in an aqueous solvent or in a mixture of aqueous solvent and organic solvent. Examples of the organic solvent include n-butyl acetate, ethyl acetate, diethyl ether, methyl n-butyl ether, di-n-butyl ether etc. Preferably, the reaction may be performed at 30° C. and the pH of the reaction solution is maintained at 6.5 with 5N NaOH.

Substrates and Products

Examples of the aliphatic compound having a carbonyl group serving as a substrate, includes ethyl 4-chloro-3-oxobutyrate represented by formula 1, ethyl-3-oxobutanoate represented by formula 7, ethyl 4-methyl-3-oxopentanoate represented by formula 8, octyl 4-chloro-3-oxobutanoate represented by formula 9, ethyl 4,4,4-trifluoro-3-oxobutanoate represented by formula 10 and ethyl 2-chloro-3-oxobutyrate represented by formula 11.

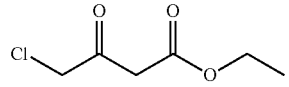

Formula 1

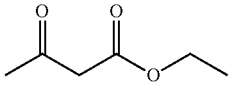

Formula 7

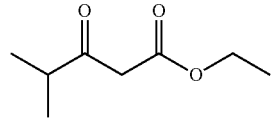

Formula 8

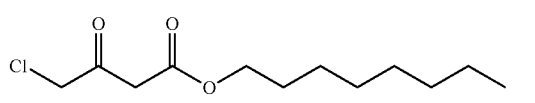

Formula 9

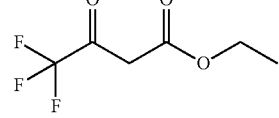

Formula 10

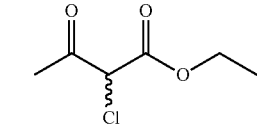

Formula 11

Examples of the aromatic compound having a carbonyl group serving as a substrate, includes acetophenone represented by formula 12, 1-(4-fluorophenyl)ethanone represented by formula 13, 1-(4-chlorophenyl)ethanone represented by formula 14, 1-(4-bromophenyl)ethanone represented by formula 15, 1-(4-(trifluoromethyl)phenyl)ethanone represented by formula 16, 1-p-tolylethanone represented by formula 17, 1-(4-methoxyphenyl)ethanone represented by formula 18 and indoline-2,3-dione represented by formula 19 below:

Formula 12
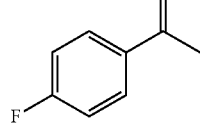

Formula 13
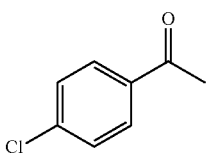

Formula 14
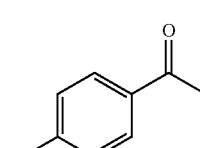

Formula 15
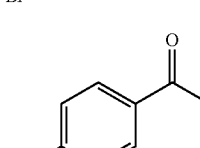

Formula 16
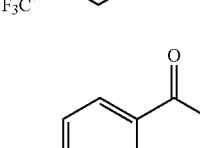

Formula 17
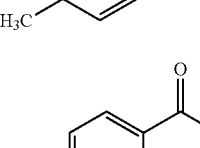

Formula 18
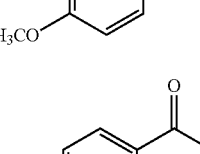

Formula 19
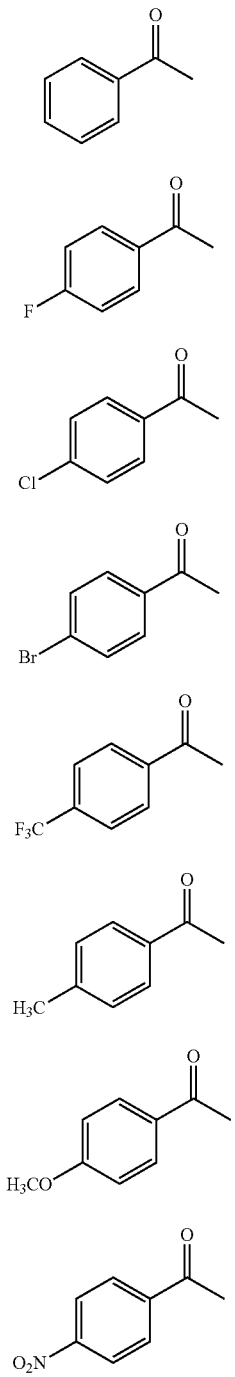

In the aforementioned reaction conditions, when ethyl 4-chloro-3-oxobutyrate represented by formula 1 above is used as a substrate, ethyl (S)-4-chloro-3-hydroxybutyrate represented by formula 2 below can be obtained.

When ethyl-3-oxobutanoate represented by formula 7 above is used as a substrate, ethyl (R)-3-hydroxybutanoate represented by formula 20 below can be obtained When ethyl 4-methyl-3-oxopentanoate represented by formula 8 above is used as a substrate, ethyl (S)-3-hydroxy-4-methylpentanoate represented by formula 21 below can be obtained.

When octyl 4-chloro-3-oxobutanoate represented by formula 9 above is used as a substrate, octyl (S)-4-chloro-3-hydroxybutanoate represented by formula 22 below can be obtained.

When ethyl 4,4,4-trifluoro-3-oxobutanoate represented by formula 10 above is used as a substrate, octyl (S)-4-chloro-3-hydroxybutanoate represented by formula 23 below can be obtained.

When ethyl 2-chloro-3-oxobutanoate represented by formula 11 above is used as a substrate, (2R,3R)-ethyl 2-chloro-3-hydroxybutanoate represented by formula 24 below can be obtained.

Formula 2
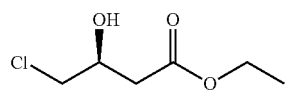

Formula 20
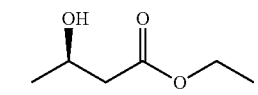

Formula 21
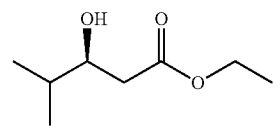

Formula 22
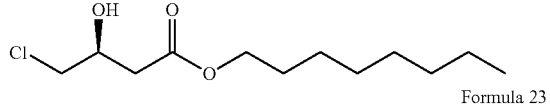

Formula 23
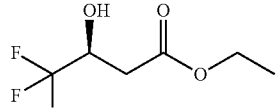

Formula 24

When acetophenone represented by formula 12 above is used as a substrate, (R)-1-phenylethanol represented by formula 25 below can be obtained.

When 1-(4-fluorophenyl)ethanone represented by formula 13 above is used as a substrate, (R)-1-(4-fluorophenyl)ethanol represented by formula 26 below can be obtained.

When 1-(4-chlorophenyl)ethanone represented by formula 14 above is used as a substrate, (R)-1-(4-chlorophenyl)ethanol represented by formula 27 below can be obtained.

When 1-(4-bromophenyl)ethanone represented by formula 15 above is used as a substrate, (R)-1-(4-bromophenyl)ethanol represented by formula 28 below can be obtained.

When 1-(4-(trifluoromethyl)phenyl)ethanone represented by formula 16 above is used as a substrate, (R)-1-(4-(trifluoromethyl)phenyl)ethanol represented by formula 29 below can be obtained.

When 1-p-tolylethanone represented by formula 17 above is used as a substrate, (R)-1-p-tolylethanol represented by formula 30 below can be obtained.

When 1-(4-methoxyphenyl)ethanone represented by formula 18 above is used as a substrate, (R)-1-(4-methoxyphenyl)ethanol represented by formula 31 below can be obtained.

When 1-(4-nitrophenyl)ethanone represented by formula 19 above is used as a substrate, (R)-1-(4-nitrophenyl)ethanol represented by formula 32 below can be obtained.

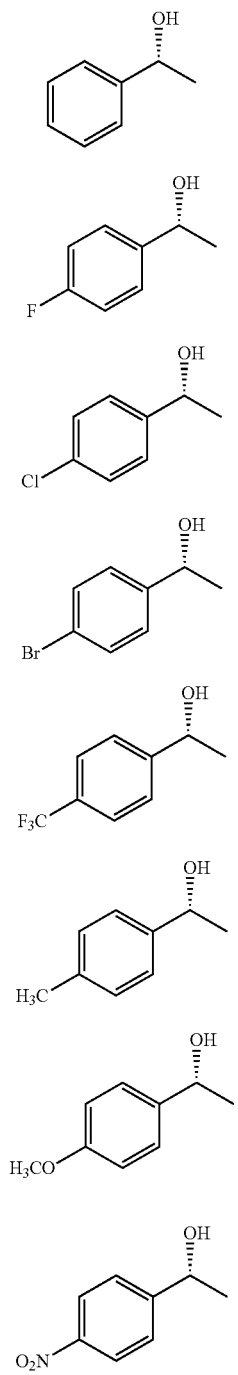

Formula 25

Formula 26

Formula 27

Formula 28

Formula 29

Formula 30

Formula 31

Formula 32

Purification and Analysis

An optically pure alcohol produced by the reaction can be purified by a conventional method, for example, by extracting a reaction mixture containing an optically pure alcohol produced by the reaction with an organic solvent ethyl acetate, removing the organic solvent by distillation under reduced pressure, and subjecting the resultant mixture to distillation, recrystallization or chromatographic process.

The optical purity of the product was measured by high performance liquid chromatography by using Chiracel OB-H, Chiracel OD-H, Chiracel OJ product of Daicel Chemical Industries or by determining the optical rotation by polarimeter.

The structure of all compounds was confirmed by NMR. NMR was run using $CDCl_3$, $CD_3OD$ or $CD_3SOCD_3$ as solvent. Chemical shifts are reported as downfield from TMS used as internal standard. Values of coupling constants J are reported in Hz.

Analytical Data

The alcohols obtained from bioctalyzed reduction of ketones were purified by flash chromatography over silica gel.

Compound of Formula 2: $^1$H NMR (300 MHz, $CDCl_3$): 1.28 (3H, t, J=7.2 Hz); 2.63 (3H, m); 3.61 (2H, dd, J=7.2, 5.4 Hz); 4.18 (2H, q, J=7.2 Hz); 4.23 (1H, m). HPLC: Chiracel OB-H, $\lambda_{217}$, hexane:isopropanol 96:4, 1 ml/min. Retention times 13.2 min (R) and 14.3 min(S). $[\alpha]_D^{25}$=−22.1 (c=8.72, $CHCl_3$).

Compound of Formula 20: $^1$H NMR (300 MHz, $CDCl_3$): 1.21 (3H, d, J=6.5 Hz); 1.26 (3H, t, J=6.8 Hz); 2.46 (2H, m); 3.00 (1H, bs); 4.16 (3H, m). HPLC: Chiracel OB-H, km, $\lambda_{217}$, hexane:isopropanol 96:4, 1 ml/min. Retention times 9.4 min (S) and 10.5 min (R). $[\alpha]_D^{25}$=−44.2 (c=2.03, $CHCl_3$).

Compound of Formula 21: $^1$H NMR (300 MHz, $CDCl_3$): 0.90 and 0.93 (each 3H, each t, J=6.8 Hz); 1.26 (3H, t, J=7.2 Hz); 1.69 (1H, m); 2.38 (1H, dd, J=9.6, 16.5 Hz); 2.52 (1H, dd, J 2.8, 16.5 Hz); 2.94 (1H, bs); 3.75 (1H, m,); 4.14 (2H, q, J=7.2 Hz). HPLC: Chiracel OD-H, $\lambda_{217}$, hexane:isopropanol 95:5, 1 ml/min. Retention times 5.3 min (S) and 7.7 min (R). $[\alpha]_D^{25}$=−40.8 (c=2.56, $CHCl_3$).

Compound of Formula 22: $^1$H NMR (300 MHz, $CDCl_3$): 0.86 (3H, t, J=6.9 Hz, $H_2CH_3$); 1.27 (10H, m, 5×$CH_2$); 1.61 (2H, m); 2.62 (2H, m); 3.60 (2H, m); 4.11 (2H, t, J=6.8 Hz); 4.14 (1H, m, H3). HPLC: Chiracel OB-H, $\lambda_{217}$, hexane:isopropanol 96:4, 1 ml/min. Retention times 5.7 min (R) and 7.6 min (S). $[\alpha]_D^{25}$=−15.9 (c=4.60, $CHCl_3$).

Compound of Formula 23: $^1$H NMR (300 MHz, $CDCl_3$): 1.29 (3H, t, J=7.2 Hz); 2.70 (2H, m); 4.21 (2H, q, J=7.2 Hz); 4.43 (1H, m). $[\alpha]_D^{25}$=−20.3 (c=1.87, $CHCl_3$).

Compound of Formula 24: $^1$H NMR (300 MHz, $CDCl_3$): 1.34 (m, 6H); 4.25 (m, 4H). de=>96% by GC: Factorfour™ (Varian, 30 m×0.25 mm, 140° C., $N_2$ 1 kg min$^{-1}$), retention time 9.98 (syn), 8.85 (anti); >99% anti. Ee.>98% GC betaDex™ (Supelco, 30 m×0.25 mm, 140° C., $N_2$ 1 kg min$^{-1}$), tentatively assigned (2R,3R) configuration based on comparison of optical rotation with literature. $[\alpha]_D^{25}$=−3.8 (c=1.13, $CHCl_3$).

Compound of Formula 25: $^1$H NMR (300 MHz, $CDCl_3$): 1.49 (3H, d, J=6.5 Hz); 2.10 (1H, bs); 4.87 (1H, q, J=6.5 Hz); 7.35 (5H, m). HPLC: Chiracel OB-H, $\lambda_{217}$, hexane:isopropanol 96:4, 1 ml/min. Retention times 6.2 min (R) and 9.2 min (S). $[\alpha]_D^{25}$=+54.8 (c=2.74, $CHCl_3$).

Compound of Formula 26: $^1$H NMR (300 MHz, $CDCl_3$): 1.49 (3H, d, J=6.5 Hz); 2.03 (1H, bs); 4.89 (1H, q, J=6.5 Hz); 7.01 and 7.03 (each 2H, each d, J=8.6 Hz). HPLC: Chiracel OB-H, $\lambda_{217}$, hexane:isopropanol 96:4, 1 ml/min. Retention times 7.8 min(S) and 8.8 min(R). $[\alpha]_D^{25}$=+48.8 (c=1.4, $CHCl_3$).

Compound of Formula 27: $^1$H NMR (300 MHz, $CDCl_3$): 1.47 (3H, d, J=6.5 Hz); 2.1 (1H, bs, OH); 4.87 (1H, q, J=6.5

Hz); 7.31 (4H, s). HPLC: Chiracel OB-H, $\lambda_{217}$, hexane: isopropanol 96:4, 1 ml/min. Retention times 8.9 min (S) and 10.5 min (R). $[\alpha]_D^{25}$=+49.2 (c=1.83, ether).

Compound of Formula 28: $^1$H NMR (300 MHz, CDCl$_3$): 1.47 (3H, d, J=6.5 Hz); 2.08 (1H, bs); 4.87 (1H, q, J=6.5 Hz); 7.25 and 7.47 (each 2H, each d, J=8.7 Hz). HPLC: Chiracel OB-H, $\lambda_{217}$, hexane:isopropanol 96:4, 1 ml/min. Retention times 9.4 min (S) and 11.4 min (R). $[\alpha]_D^{25}$=+38.3 (c=1.55, CHCl$_3$).

Compound of Formula 29: $^1$H NMR (300 MHz, CDCl$_3$): 1.5 (3H, d, J=6.51 Hz); 2.33 (1H, bs); 4.98 (1H, q, J=6.5 Hz); 7.48 and 7.60 (each 2H, each d, J=8.2 Hz). $[\alpha]_D^{25}$=+ 27.2 (c 2.08, MeOH).

Compound of Formula 30: $^1$H NMR (300 MHz, CDCl$_3$): 1.48 (3H, d, J=6.5 Hz); 2.01 (1H, bs); 2.38 (1H, s); 4.87 (1H, q, J=6.5 Hz); 7.15 and 7.26 (each 2H, each d, J=7.9 Hz). HPLC:Chiracel OB-H, $\lambda_{217}$, hexane:isopropanol 95:5, 1 ml/min. Retention times 10.1 min (S) and 12.9 min (R). $[\alpha]_D^{25}$=+52.1 (c=1.98, CHCl$_3$).

Compound of Formula 31: $^1$H NMR (300 MHz, CDCl$_3$): 1.46 (3H, d, J=6.5 Hz); 2.08 (1H, bs); 3.80 (3H, s); 4.84 (1H, q, J=6.5 Hz); 6.86 and 7.28 (each 2H, each d, J=8.2). $[\alpha]_D^{22}$=+51.4 (c 1.72, CHCl$_3$).

Compound of Formula 32: $^1$H NMR (300 MHz, CDCl$_3$): 1.52 (3H, t, J=6.5 Hz, CH$_3$); 2.50 (1H, bs, OH); 5.02 (1H, q, J=6.5 Hz, CH); 7.54 and 8.12 (each 2H, each d, J=8.9 Hz, aryl). $[\alpha]_D^{25}$=+31.4 (c=3.99, CHCl$_3$).

The following description is of exemplary embodiments only and is not intended to limit the scope, applicability or configuration to the invention in any way, Rather, the following description provides a convenient illustration for implementing exemplary embodiments of the invention various changes to the described embodiments may be made in the functions and arrangement of the elements described without departing from the scope of the invention.

EXAMPLES

The specific manipulation methods regarding recombinant DNA techniques used in the following examples are described in the following publication (Sambrook, J. et al. Molecular Cloning: A Laboratory Manual. Cold Spring Harbor Laboratory Press. 1989; Vol. 2.).

Example 1

Construction of Expression Plasmid pET23(a)-Omp-CRS Expressing Carbonyl Reductase on the Surface of *Escherichia coli*

The artificial custom synthesized plasmid pUC 19-omp-CRS having DNA according to present invention has nucleotide sequence of SEQ ID NO:2 of the Sequence Listing codes for the polypeptide has an amino acid sequence of SEQ ID NO:1 of the Sequence Listing were double digested by Nde1 and EcoR1 and product was separated by agarose gel electrophoresis, 1.3 Kb DNA fragment has nucleotide sequence of SEQ ID NO:2 of the Sequence Listing, was excised from the gel and purified using Qiaquick kit (Qiagen). Plasmid. pET 23(a) was separately digested with Nde1 & EcoR1, followed by the dephosphorylation with calf intestinal alkaline phosphatase to avoid self-ligation. Nde1 & EcoR1 (NEB Ltd, UK) digested 1.3 Kb DNA fragment has nucleotide sequence of SEQ ID NO:2 of the Sequence Listing and pET 23(a) were ligated with T4 DNA Ligase (NEB Ltd, UK) and transformed in *Escherichia coli* DH5α. The resultant clones were grown in LB broth containing ampicillin (100 mg/ml) and plasmid was isolated, which was then double digested by Nde1 and EcoR1. Plasmid giving the 3.6 Kb pET 23(a) backbone and 1.3 Kb DNA insert after double digestion, suggesting nucleotide sequence of SEQ ID NO:2 of the Sequence Listing was cloned downstream of the lac promoter of pET 23(a) giving 4.9 Kb plasmid pET 23(a)-omp-CRS.

A restriction map of plasmid pET 23(a)-omp-CRS is illustrated in FIG. 5.

*Escherichia coli* BL21(DE3), *Escherichia coli* C41(DE3) or *Escherichia coli* C43(DE3) was transformed with plasmid pET 23(a)-omp-CRS which expresses carbonyl reductase on the surface of the transformants.

Example 2

Construction of Expression Vector pET23(a)-CRS Expressing Carbonyl Reductase in the Cytoplasm of Transformants It was constructed by using the knowledge disclosed in US Patent 2010/0028972. CRSF (SEQ ID NO:26) and CRSR (SEQ ID NO:28) primers for cloning were synthesized based on the nucleotide sequence of carbonyl reductase gene represented by SEQ ID NO:14 of the Sequence Listing, which code a polypeptide has an amino acid sequence of SEQ ID NO:13 of the Sequence Listing. The custom synthesized pUC 19-omp-CRS plasmid was subjected to polymerase chain reaction (PCR) for 30 cycles of a reaction. The PCR conditions were, initial denaturing at 95° C. for 5 min followed by 30 cycles of 95° C. for 60 s, 58° C. for 60 s and 72° C. for 60 s as well as a final extension step of 72° C. for 5 min. The purified PCR product was digested with Nde1 & Xho1, and was run on the 1% agarose gel. The 0.87 Kb Nde1 and Xho1 digested fragment was excised from the gel and purified using Qiaquick kit (Qiagen). Plasmid pET 23(a) was separately digested with Nde1 & Xho1, followed by the dephosphorylation with calf intestinal alkaline phosphatase to avoid self-ligation. Nde1 and Xho1 digested 0.87 Kb has nucleotide sequence of SEQ ID NO:14 of the Sequence Listing and pET 23(a) were ligated with T4 DNA Ligase and transformed in *Escherichia coli* DH5α. The resultant clones were grown in LB broth containing ampicillin and plasmid were isolated, which were then double digested with Nde1 and Xho1. Plasmid gave 3.6 Kb pET 23(a) backbone and 0.87 Kb insert after double digestion, suggesting 0.87 Kb gene was cloned downstream of the lac promoter of pET 23(a) giving 4.4 Kb plasmid pET 23(a)-CRS.

*Escherichia coli* BL21(DE3) was transformed with plasmid pET 23(a)-CRS which express carbonyl reductase in the cytoplasm.

Example 3

Construction of Expression Vector pETDuet1-Omp-CRS; Omp-GDH Co Expressing Carbonyl Reductase and Glucose Dehydrogenase on the Surface of Transformants Construction of expression vector pETDuet1-omp-CRS; omp-GDH, which co expressing the two polypeptides, one having the carbonyl reductase activity has an amino acid sequence of SEQ ID NO: 1 of the Sequence Listing and the other polypeptide has an amino acid sequence of SEQ ID NO: 3 of the Sequence Listing having coenzyme regeneration activity on the surface of the transformant/s. To achieve this goal, inventors have chosen plasmid pETDuet1 that contains two multiple cloning sites, each of which is preceded by a T7 promoter/lac operator and a ribosome binding site (rbs). omp-CRS and omp-GDH gene were cloned in pETDuet1 plasmid, which is a two-step procedure.

In first step, DNA according to present invention has nucleotide sequence of SEQ ID NO:2 of the Sequence Listing codes for the polypeptide has an amino acid sequence of SEQ ID NO:1 of the Sequence Listing was amplified from the plasmid pUC19-omp-CRS that was used as a template for polymerase chain reaction (PCR) with the primers oc1F (SEQ ID NO:30) and oc1R (SEQ ID NO:32). The PCR conditions were, initial denaturing at 95° C. for 5 min followed by 30 cycles of 95° C. for 60 s, 55° C. for 60 s and 72° C. for 90 s as well as a final extension step of 72° C. for 5 min. The purified PCR product was digested by Nco1 and Hind3 and was run on the 1% agarose gel. The 1.3 Kb Nco1 and Hind3 fragment was excised from the gel and purified using Qiaquick kit (Qiagen). Plasmid pETDuet was separately digested with Nco1 and Hind3, followed by the dephosphorylation with calf intestinal alkaline phosphatase to avoid self-ligation. Nco1 and Hind3 digested omp-CRS and pETDuet1 were ligated with T4 DNA Ligase and transformed in *Escherichia coli* DH5α. The resultant clones were grown in LB broth containing ampicillin (100 μg/ml) from which plasmid was isolated and then double digested with Nco1 and Hind3. Plasmid gave ~5.4 Kb pETDuet1 backbone and 1.3 Kb SEQ ID NO:2 insert after double digestion, suggesting SEQ ID NO:2 was cloned downstream of the lac promoter of pETDuet1 in the $1^{st}$ multiple cloning site giving 6.7 Kb plasmid pETDuet1-omp-CRS.

In second step, DNA according to present invention has nucleotide sequence of SEQ ID NO:4 of the Sequence Listing codes for the polypeptide has an amino acid sequence of SEQ ID NO:3 of the Sequence Listing was amplified from the artificial custom made plasmid pUC19-omp-GDH that was used as a template in polymerase chain reaction (PCR) with the primers ogF (SEQ ID NO:34) and ogR (SEQ ID NO:36). The PCR conditions were, initial denaturing at 95° C. for 5 min followed by 30 cycles of 95° C. for 60 s, 52° C. for 60 s and 72° C. for 90 s as well as a final extension step of 72° C. for 5 min. The purified PCR product was digested by Nde1 and Xho1 and was run on the agarose gel. The 1.2 Kb Nde1 and Xho1 digested fragment was excised from the gel and purified using Qiaquick kit (Qiagen). 6.7 Kb plasmid pETDuet1-omp-CRS constructed as described above was separately digested with Nde1 and Xho1, followed by the dephosphorylation with calf intestinal alkaline phosphatase to avoid self-ligation. Nde1 and Xho1 digested SEQ ID NO:4 and pETDuet1-omp-CRS were ligated with T4 DNA Ligase and transformed in *Escherichia coli* DH5α. The resultant clones were grown in LB broth containing ampicillin and from which plasmid was isolated, which was then double digested by Nde1 and Xho1. Plasmid gave the ~6.7 Kb pETDuet1-omp-CRS backbone and 1.2 Kb omp-GDH insert after double digestion, suggesting omp-GDH gene was cloned downstream of the lac promoter of pETDuet1-omp-CRS in the $2^{nd}$ multiple cloning site in 7.8 Kb plasmid pETDuet1-omp-CRS, omp-GDH.

A restriction map of plasmid pETDuet1-omp-CRS, omp-GDH is illustrated in FIG. 6.

*Escherichia coli* BL21(DE3), *Escherichia coli* C41(DE3) and *Escherichia coli* C43(DE3) were transformed with plasmid pETDuet1-omp-CRS, omp-GDH which co express carbonyl reductase and glucose dehydrogenase on the surface of transformant/s.

Example 4

Preparation of Transformant

Using the recombinant plasmid pET23(a)-omp-CRS constructed in Example 1, the *Escherichia coli* BL21(DE3), *Escherichia coli* C41(DE3) and *Escherichia coli* C43(DE3) competent cells were transformed to obtain *Escherichia coli* BL21 (DE3)+pET23(a)-omp-CRS, *Escherichia coli* C41 (DE3)+pET23(a)-omp-CRS and *Escherichia coli* C43 (DE3)+pET23(a)-omp-CRS expressing carbonyl reductase on the surface.

Similarly, using the recombinant plasmid pETDuet1-omp-CRS; omp-GDH constructed in example 3, the *Escherichia coli* BL21(DE3), *Escherichia coli* C41(DE3), *Escherichia coli* C43(DE3) and *Escherichia coli* competent cells were transformed to obtain *Escherichia coli* BL21 (DE3)+pETDuet1-omp-CRS; omp-GDH, *Escherichia coli* C41 (DE3)+pETDuet1-omp-CRS; omp-GDH and *Escherichia coli* C43(DE3)+pETDuet1-omp-CRS; omp-GDH expressing both carbonyl reductase and glucose dehydrogenase on the surface.

Using the recombinant plasmid pET23(a)-CRS constructed in example 2, the *Escherichia coli* BL21(DE3) competent cells was transformed to obtain *Escherichia coli* BL21 (DE3)+pET23(a)-CRS expressing carbonyl reductase in cytoplasm of the cell.

Using the recombinant plasmid pET23(a)-crs constructed in example 2 and pET 29(a)-GDH constructed as given below, the *Escherichia coli* BL21(DE3) competent cells were co-transformed to obtain *Escherichia coli* BL21 (DE3)+pET23(a)-CRS, pET 29(a)-GDH expressing carbonyl reductase and glucose dehydrogenase in cytoplasm of the cell. *Escherichia coli* BL21 (DE3)+pET23(a)-CRS, pET 29(a)-gdh was constructed by using the art disclosed in Kizaki, N. et al. *Applied Microbiology and Biotechnology* 2001, 55, 590-595.

Construction of Recombinant Plasmid pET29(a)-GDH:

gdhF (SEQ ID NO 38) and gdhR (SEQ ID NO 40) primers for cloning were synthesized based on the nucleotide sequence of glucose dehydrogenase gene represented by SEQ ID NO 26 of the Sequence Listing, which code a polypeptide has an amino acid sequence of SEQ ID NO 25 of the Sequence Listing. The custom synthesized pUC 19-omp-gdh plasmid was subjected to polymerase chain reaction (PCR) for 30 cycles of a reaction. The PCR conditions were, initial denaturing at 95° C. for 5 min followed by 30 cycles of 95° C. for 60 s, 52° C. for 60 s and 72° C. for 60 s as well as a final extension step of 72° C. for 5 min. The purified PCR product was digested with Nde1 & Xho1, and was run on the 1% agarose gel. The 0.81 Kb Nde1 and Xho1 digested fragment was excised from the gel and purified using Qiaquick kit (Qiagen). Plasmid pET 29(a) was separately digested with Nde1 & Xho1, followed by the dephosphorylation with calf intestinal alkaline phosphatase to avoid self-ligation. Nde1 and Xho1 digested 0.81 Kb has nucleotide sequence of SEQ ID NO 26 of the Sequence Listing and pET 29(a) were ligated with T4 DNA Ligase and transformed in *Escherichia coli* DH5α. The resultant clones were grown in LB broth containing kanamycin and plasmid were isolated, which were then double digested with Nde1 and Xho1. Plasmid gave 5.4 Kb pET 29(a) backbone and 0.81 Kb insert after double digestion, suggesting 0.81 Kb gene was cloned downstream of the lac promoter of pET 29(a) giving 6.0 Kb plasmid pET 29(a)-GDH.

Example 5

Expression of Gene in Transformant

Fresh culture of recombinant *Escherichia coli* harboring plasmid was grown in 10 ml Luria Bertani HiVeg Broth media (1% HiVeg hydrolase, 0.5% Yeast Extract, 1% Sodium Chloride, pH-7.5) containing antibiotic (ampicillin, kanamycin, chloramphenicol etc. alone or in combination) at 37° C., after 6 hr of growth 1 ml of the culture was inoculated in 100 ml fresh LB media containing antibiotic (ampicillin, kanamycin, chloramphenicol etc. alone or in combination) and grown at 37° C. under 200 rpm shaking condition. When the OD at 600 nm was reached to 0.5-0.6, the culture was induced with final concentration of 0.2 mM IPTG and it was further grown for 16 hr at 20° C. under 200 rpm shaking condition.

Example 6

Demonstration of the Expression of Carbonyl Reductase on the Surface of Transformant Escherichia coli BL21(DE3)+ pET 23(a)-Omp-CRS (CRS, Sequence ID No 1)

The transformant Escherichia coli BL21(DE3)+pET23 (a)-omp-CRS was grown as described in example 5 above, in 100 ml culture media. The cells were isolated by centrifugation and washed with 50 mM phosphate buffer (pH 7.0). The cells were then suspended in 5 ml lysis buffer (50 mM $NaH_2PO_4$, 150 mM NaCl, 1 mg $ml^{-1}$ Lysozyme, pH 8.0) for 30 min at 4° C. The cell suspension was then sonicated 30 sec pulse on and 30 sec pulse off at 4° C. for 20 min. The cell debris was removed by centrifugation at 14,000 rpm for 30 min. The supernatant (cell-free extract) was then subjected to ultra-centrifugation at 1,00,000 g for 2 hr at 4° C. for separation of membrane fraction and soluble fraction. The sediment containing the membrane fraction was washed with the same buffer and re-suspended in membrane solubilization buffer (25 mM Tris HCl, 20% Glycerol and 2% Triton X100, pH 7.5). All the three fractions, cell-free extract, membrane fraction and soluble protein fraction were assayed for their activity to reduce ethyl 4-chloro-3-oxobutyrate to ethyl 4-chloro-3-hydroxybutyrate, like, the standard reaction mixture (1 ml) in 50 mM phosphate buffer pH 7.0, containing 0.2 mM nicotinamide adenine dinucleotide phosphate, reduced (NADPH), 2.0 mM ECOB and 1-50 μl of the sample was incubated at 30° C. and the total activity determined. The results have been summarized in Table 1. As expected, most of the activity was recovered from membrane fraction. Significantly, membrane fractions of the Escherichia coli BL21 (DE3)+pET23(a) (negative control) was devoid of any activity.

TABLE 1

Carbonyl reductase (CRS) activity of various fractions obtained from Escherichia coli BL21(DE3) + pET23(a) and Escherichia coli BL21 + pET 23(a)-omp-CRS (CRS, Sequence ID No 1).

| Entry | Fractions of Escherichia coli | Escherichia coli BL21(DE3) + pET 23(a), Total activity (nmol/min) | Escherichia coli BL21(DE3) + pET 23(a)-omp-CRS, Total activity (nmol/min) |
|---|---|---|---|
| 1 | Cell-free extract | 376 | 1673 |
| 2 | Soluble fraction | 76 | 350 |
| 3 | Membrane fraction | 0.0 | 1192 |

The presence of CRS on the surface of Escherichia coli BL21(DE3)+pET 23(a)-omp-CRS was further confirmed by EM immunogold labeling studies carried out with ultrathin sections of Escherichia coli BL21(DE3)+pET 23(a)-omp-cr1 cells. Anti-CRS polyclonal antibody was raised against the purified CRS in rabbit and was assayed for their specificity by Western blotting. The purified CRS was run on SDS-PAGE under the reducing condition and after electroblotting on to nitrocellulose membrane was probed with rabbit anti-CRS polyclonal antibody which was further probed with alkaline phosphatase conjugated goat anti-rabbit IgG (whole molecule) secondary antibody. The blot was then developed by dipping it in the substrate solution containing 5-bromo-4-chloro-3-indolyl phosphate (BCIP, 0.15 mg/ml), nitro blue tetrazolium (NBT, 0.30 mg/ml), Tris HCl (100 mM) and $MgCl_2$ (5 mM), pH 9.5 for 10 minute. The polyclonal antibody that specifically labeled pure CRS was also able to specifically label omp-CRS.

After several dehydration steps, recombinant Escherichia coli BL21(DE3)+pET 23(a) (negative control) and Escherichia coli BL21(DE3)+pET 23(a)-omp-CRS were embedded in LR white resin, which was then dehydrated in several steps using 0.2% glutaraldehyde as fixative. Thin sections cut using an ultramicrotome were incubated with rabbit anti-CRS polyclonal antibody followed by nanogold-labeled goat anti-rabbit IgG (whole molecule) secondary antibody and visualized under the transmission electron microscope. Different fields were observed and the gold particles were found to be exclusively present on the surface of the cells (FIG. 7). No labeling occurred with cells as the negative control.

Example 7

Relative Expression Levels of Cytoplasmic and Surface Expressed CRS in Transformant Escherichia coli BL21 (DE3)+pET 23(a)-Omp-CRS (CRS, Sequence ID No 1)

Fresh culture of recombinant Escherichia coli BL21 (DE3)+pET 23(a)-CRS (CRS, Sequence ID No 1) and Escherichia coli BL21(DE3)+pET 23(a)-omp-CRS (CRS, Sequence ID No 1) were grown and whole cell proteome of each clone was prepared. The proteome obtained from various concentrations of cells was run on 12.5% SDS-PAGE under reducing conditions. After electro blotting on to nitrocellulose membrane, it was probed with rabbit anti-CRS polyclonal antibody, which was further probed with alkaline phosphatase conjugated goat-anti rabbit IgG antibody. Probing with antibody was followed by developing the blot by dipping it in the substrate solution containing 5-bromo-4-chloro-3-indolyl phosphate (BCIP, 0.15 mg ml$^{-1}$), nitro blue tetrazolium (NBT, 0.30 mg ml$^{-1}$), Tris HCl (100 mM) and MgCl$_2$ (5 mM), pH 9.5 for 10 min. The expression of the CRS was determined by analyzing the band intensity by software Scion Image of the corresponding clone. The intensity was plotted against amount of the cells taken and the slope (dy/dx) for the intracellular expression and surface expression compared. The expression of CRS on the surface of the cells as omp-CRS fusion protein was found to be 17.9-fold less as compared to CRS expressed in the cytoplasm.

Example 8

Surface Expressed CRS Showed 275-Fold Increased Activity Compared to Cytoplasmic CRS for Reduction of Ethyl 4-Chloro-3-Oxobutyrate Fresh culture of recombinant *Escherichia coli* BL21 (DE3)+pET 23(a)-CRS (CRS Sequence ID No 1) and *Escherichia coli* BL21(DE3)+pET 23(a)-omp-CRS (CRS Sequence ID No 1) were grown and used to determine the carbonyl reductase activity. The assay was done using ethyl 4-chloro-3-oxobutyrate as substrate and nicotinamide adenine dinucleotide phosphate, reduced (NADPH) as cofactor. The initial rate of carbonyl reductase activity was determined by monitoring the decrease in absorbance of nicotinamide adenine dinucleotide phosphate, reduced (NADPH) at $\lambda_{340}$. The standard reaction mixture (1 ml) in 50 mM phosphate buffer pH 7.0 contained 0.2 mM nicotinamide adenine dinucleotide phosphate, reduced (NADPH), $10^6$-$10^8$ recombinant *Escherichia coli* cells and 2.0 mM ethyl (S)-4-chloro-3-oxobutanoate. One unit of activity was defined as the amount of dry cell weight that catalyzed the oxidation of 1 μmol nicotinamide adenine dinucleotide phosphate, reduced (NADPH) per minute under specified conditions. The activity of recombinant *Escherichia coli* BL21(DE3)+pET 23(a)-omp-CRS (CRS Sequence ID No 1) expressing omp-CRS on the surface was determined to be 156.20×10$^3$ nmol/min/gm dry cell weight. In comparison recombinant *Escherichia coli* BL21(DE3)+pET 23(a)-CRS (CRS Sequence ID No 1) expressing CRS in cytoplasm showed activity of 10.16×10$^3$ nmol/min/gm dry cell weight. Thus, for equal amount of cells, the surface displayed CRS showed 15.4-fold higher activity. However, we have shown that for equal amount of cells, the recombinant *Escherichia coli* BL21(DE3)+pET 23(a)-CRS expressed 17.9-fold more protein as compared to recombinant *Escherichia coli* BL21+pET23(a)-omp-CRS. Thus, activity per unit protein for recombinant *Escherichia coli* BL21(DE3)+pET23(a)-omp-CRS was 275-fold higher than recombinant *Escherichia coli* BL21(DE3)+pET23(a)-omp-CRS. The result has been summarized in Table 2.

TABLE 2

Relative activity of recombinant *Escherichia coli* expressing CRS (CRS Sequence ID No 1) on surface as omp-CRS fusion protein and recombinant *Escherichia coli* expressing CRS (CRS Sequence ID No 1) in cytoplasm.

| Clone used for the experiment | Activity (nmole/min/gm DCW*) | Relative concentration of CRS | Activity per unit of CRS | Fold increase in activity |
| --- | --- | --- | --- | --- |
| *Escherichia coli* Bl21(DE3) + CRS-pET23(a) | 10.16 × 10$^3$ | 17.9 | 0.57 × 10$^3$ | 1 |
| *Escherichia coli* Bl21(DE3) + omp-CRS-pET23(a) | 156.20 × 10$^3$ | 1 | 156.20 × 10$^3$ | 275.19 |

*DCW = Dry cell weight.
Negative control *Escherichia coli* BL21(DE3) + pET23(a) did not given any activity.

Example 9

Surface Expressed CRS Showed 50-Fold to 275-Fold Increased Activity Compared to Cytoplasmic CRS for Reduction of Variant Ketones The assays were done in 96-well ELISA plate. The reaction mixture consisting of 0.2 mM nicotinamide adenine dinucleotide phosphate, reduced (NADPH), 2.0 mM substrate, 50 μg/ml *Escherichia coli* cells (for calculation of cell mass, OD$_{600}$=1 of cell suspension was taken as equivalent to 0.25 mg/ml dry cell weight) in 50 mM phosphate buffer, pH 7.0 was incubated at 30° C. for about 30 min to 12 hr depending upon the consumption of the substrate. The consumption of nicotinamide adenine dinucleotide phosphate, reduced (NADPH) was monitored by decrease in the absorbance at $\lambda_{340}$. The results have been summarized in Table 3 and 4. As expected surface expressed CRS (CRS Sequence ID no 1) was much more efficient than intracellularly expressed CRS Sequence ID no 1) in reduction of a variety of aliphatic and aromatic ketones. In general, the increase in activity was in the range of 50-fold and 275-fold per unit CRS protein under these conditions. The relative concentration of CRS was determined as described in Example 7.

TABLE 3

Relative activity of recombinant *Escherichia coli* expressing CRS (Sequence ID No 1) on surface as omp-CRS fusion protein and recombinant *Escherichia coli* expressing CRS (Sequence ID No 1) in cytoplasm for variant ketones[a].

| Entry | Substrate | *Escherichia coli* BL21 + pET23(a)-CRS (nmol/min/gm DCW*) | *Escherichia coli* BL21 + pET23(a)-omp-CRS (nmol/min/gm DCW*) | Fold increase in activity per unit DCW* | Fold increase in activity per unit protein# |
|---|---|---|---|---|---|
| 1 | Ethyl 4-chloro-3-oxobutyrate | $10.16 \times 10^3$ | $156.20 \times 10^3$ | 15.37 | 275.19 |
| 2 | Ethyl 2-chloro-3-oxobutyrate | $30.06 \times 10^3$ | $161.48 \times 10^3$ | 5.37 | 96.12 |
| 3 | Ethyl-3-oxobutyrate | $3.60 \times 10^3$ | $12.01 \times 10^3$ | 3.34 | 59.80 |
| 4 | Ethyl 4-methyl-3-oxopentanoate | $3.52 \times 10^3$ | $43.12 \times 10^3$ | 12.25 | 219.27 |
| 5 | Octyl 4-chloro-3-oxobutanoate | $1.72 \times 10^3$ | $10.12 \times 10^3$ | 5.88 | 105.25 |
| 6 | ethyl 4,4,4-trifluoro-3-oxobutyate | $1.94 \times 10^3$ | $5.54 \times 10^3$ | 2.86 | 51.19 |
| 8 | Acetophenone | $1.54 \times 10^3$ | $5.19 \times 10^3$ | 3.37 | 60.3 |
| 9 | 4-Chloroacetophenone | $3.43 \times 10^3$ | $12.28 \times 10^3$ | 3.58 | 64.09 |
| 10 | 4-Bromoacetophenone | $3.79 \times 10^3$ | $18.48 \times 10^3$ | 4.88 | 87.28 |
| 11 | 4-Fluoroacetophenone | $2.56 \times 10^3$ | $22.88 \times 10^3$ | 8.94 | 159.98 |
| 12 | 4-Methylacetophenone | $1.94 \times 10^3$ | $5.45 \times 10^3$ | 2.82 | 50.29 |
| 13 | 4-Methoxyacetophenone | $1.06 \times 10^3$ | $3.60 \times 10^3$ | 3.40 | 60.79 |
| 14 | 4-trifluoromethylacetophenone | $3.0 \times 10^3$ | $30.10 \times 10^3$ | 10.03 | 179.60 |
| 15 | 4-Nitroacetophenone | $6.16 \times 10^3$ | $49.63 \times 10^3$ | 8.06 | 142.22 |

[a]External GDH was added to assay mixture for cofactor recycle
*DCW = Dry cell weight
The CRS expression per g DCW was 17.9-fold lower for surface expressed CRS compared to cytoplasmically expressed CRS (Example 7).

TABLE 4

Relative activity of recombinant *Escherichia coli* co-expressing CRS (Sequence ID No 1) and GDH (Sequence ID No 9) on surface as omp-CRS fusion protein and omp-GDH protein and recombinant *Escherichia coli* co-expressing CRS (Sequence ID No 1) and GDH (Sequence ID No 1) in cytoplasm for variant ketones.

| Entry | Substrate | *Escherichia coli* C41(DE3) + pETDuet1-CRS, GDH (nmol/min/gm DCW*) | *Escherichia coli* C41(DE3) + pETDuet1-omp-CRS, omp-GDH (nmol/min/gm DCW*) | Fold increase in activity per unit DCW* | Fold increase in activity per unit protein# |
|---|---|---|---|---|---|
| 1 | Ethyl 4-chloro-3-oxobutyrate | $14.42 \times 10^3$ | $217.36 \times 10^3$ | 15.08 | 269.87 |
| 2 | Ethyl 2-chloro-3-oxobutyrate | $37.26 \times 10^3$ | $165.88 \times 10^3$ | 4.45 | 79.69 |
| 3 | Ethyl-3-oxobutyrate | $4.03 \times 10^3$ | $12.76 \times 10^3$ | 3.17 | 56.74 |
| 4 | Ethyl 4-methyl-3-oxopentanoate | $4.06 \times 10^3$ | $53.02 \times 10^3$ | 13.06 | 233.90 |
| 5 | Octyl 4-chloro-3-oxobutanoate | $1.65 \times 10^3$ | $9.50 \times 10^3$ | 5.74 | 102.78 |
| 6 | ethyl 4,4,4-trifluoro-3-oxobutyate | $1.65 \times 10^3$ | $5.48 \times 10^3$ | 3.31 | 59.33 |
| 7 | Acetophenone | $2.53 \times 10^3$ | $5.79 \times 10^3$ | 2.29 | 41.03 |
| 8 | 4-Chloroacetophenone | $3.26 \times 10^3$ | $11.07 \times 10^3$ | 3.40 | 60.78 |
| 9 | 4-Bromoacetophenone | $2.44 \times 10^3$ | $19.54 \times 10^3$ | 8.0 | 143.26 |
| 10 | 4-Fluoroacetophenone | $2.96 \times 10^3$ | $22.66 \times 10^3$ | 7.64 | 136.82 |
| 11 | 4-Methylacetophenone | $1.97 \times 10^3$ | $6.53 \times 10^3$ | 3.31 | 59.19 |
| 12 | 4-Methoxyacetophenone | $1.22 \times 10^3$ | $3.32 \times 10^3$ | 2.73 | 48.81 |
| 13 | 4-trifluoromethylacetophenone | $3.37 \times 10^3$ | $29.37 \times 10^3$ | 8.71 | 155.99 |
| 14 | 4-Nitroacetophenone | $7.07 \times 10^3$ | $46.31 \times 10^3$ | 6.55 | 117.28 |

*DCW = Dry cell weight
The CRS expression per g DCW was 17.9-fold lower for surface expressed CRS compared to cytoplasmically expressed CRS.

Example 10

Demonstration of the Expression of Glucose Dehydrogenase on the Surface of Transformant *Escherichia coli* C41(DE3)+pETDuet1-Omp-CRS, Omp-GDH (CRS, Sequence ID No 1; GDH, Sequence ID No 9)

The transformant *Escherichia coli* C41(DE3)+pETDuet1-omp-CRS; omp-GDH (CRS, Sequence ID No 1; GDH, Sequence ID No 9) was grown as described in example 5 above, in 100 ml culture media. The cells were isolated by centrifugation and washed with 50 mM phosphate buffer (pH 7.0). The cells were then suspended in 5 ml lysis buffer (50 mM NaH$_2$PO$_4$, 150 mM NaCl, 1 mg ml$^{-1}$ Lysozyme, pH 8.0) for 30 min at 4° C. The cell suspension was then sonicated with 30 sec pulse on and 30 sec pulse off at 4° C. for 20 min. The cell debris was removed by centrifugation at 14000 rpm for 30 min and supernatant (cell free extract) was taken for further analysis. Membrane fraction and soluble protein fraction from the supernatant (cell-free extract) were separated as described earlier. All the three fractions, cell-free extract, membrane fraction and soluble protein fraction were assayed for their ability to oxidize glucose to gluconate, like the standard reaction mixture (1 ml) in 100 mM tris-HCl buffer, pH 8.0, containing 0.5 mM nicotinamide adenine dinucleotide phosphate (NADP) (50 µl of 7.78 mg ml$^{-1}$), 5 mM glucose (25 µl of 180 mg ml$^{-1}$) and 1-50 µl of the sample was incubated at 30° C. and the activity was determined by monitoring the formation of nicotinamide adenine dinucleotide phosphate, reduced (NADPH) at $\lambda_{340}$. The results have been summarized in Table 5. As expected most of the activity was recovered from membrane fraction. The membrane fraction of Escherichia coli C41(DE3)+pETDuet1 (negative control) was devoid of any activity.

TABLE 5

Glucose dehydrogenase (GDH) activity of various fractions from Escherichia coli C41(DE3) + pETDuet1-omp-CRS, omp-GDH (CRS, Sequence ID No 1; GDH, Sequence ID No 9) and Escherichia coli C41(DE3) + pETDuet1

| Entry | Fraction of Escherichia coli | Escherichia coli C41(DE3) + pETDuet1 Total activity (nmol/min) | Escherichia coli C41(DE3) + pETDuet1-omp-CRS, omp-GDH Total activity (nmol/min) |
|---|---|---|---|
| 1 | Cell-free extract | 632.26 | 6275.02 |
| 2 | Soluble fraction | 438.71 | 1055.72 |
| 3 | Membrane fraction | 0.0 | 4290.32 |

Example 11

Relative Expression Levels for Cytoplasmic and Surface Expressed GDH (Sequence ID No 9) in Escherichia coli C41(DE3)

Glucose dehydrogenase activity of recombinant Escherichia coli C41(DE3)+pET 29(a)-CRS+pET 29(a)-GDH (CRS, Sequence ID No 1; GDH, Sequence ID No 9) and Escherichia coli C41(DE3)+pETDuet1-omp-CRS, omp-GDH (CRS, Sequence ID No 1; GDH, Sequence ID No 9) was determined by monitoring the increase in the absorbance of nicotinamide adenine dinucleotide phosphate, reduced (NADPH) at 340 nm spectrophotometrically using glucose as a substrate. The reaction mixture (1 ml) in 50 mM Tris-HCl buffer pH 8.0, contained 0.5 mM nicotinamide adenine dinucleotide phosphate (NADP)$^+$, $10^6$ to $10^8$ cells and 5.0 mM glucose. One unit of activity was defined as the amount of cells (dry cell weight) that catalyzed the reduction of 1 µmol NADP per minute under these conditions. Recombinant Escherichia coli expressing GDH on the surface of the cells as omp-GDH fusion protein showed activity of 683.52×10$^3$ nmol/min/gm dry cell weight, whereas recombinant Escherichia coli expressing GDH in the cytoplasm showed activity of 41.87×10$^3$ nmol/min/gm dry cell weight. The relative expression level of GDH expressed on the surface and in cytoplasm was estimated from SDS PAGE. The cytoplasmic expression was estimated to be about 13.8-fold higher compared to surface expressed protein of recombinant Escherichia coli Escherichia coli C41(DE3)+ pETDuet1-omp-CRS, omp-GDH was 225-fold higher compared to recombinant Escherichia coli C41(DE3)+pET 29(a)-CRS+pET 29(a)-GDH. The results are summarized in Table 6.

TABLE 6

Relative activity of recombinant Escherichia coli expressing GDH on surface as omp-GDH (Sequence ID No 9) fusion protein and recombinant Escherichia coli expressing GD (Sequence ID No 9). in cytoplasm

| Clone used for the experiment | Activity (nmole/min/gm DCW*) | Relative concentration of GDH | Activity per unit of GDH | Fold increase in activity |
|---|---|---|---|---|
| Escherichia coli C41(DE3) + pET 29(a)-CRS + pET 29(a)-GDH | 41.87 × 10$^3$ | 13.8 | 3.03 × 10$^3$ | 1 |
| Escherichia coli C41(DE3) + pETDuet1-omp-CRS, omp-GDH | 683.52 × 10$^3$ | 1 | 683.52 × 10$^3$ | 225.58 |

*DCW = Dry cell weight
Negative control Escherichia coli BL21(DE3) + pET29(a) did not given any activity Example 12

Production of Ethyl (S)-4-Chloro-3-Hydroxybutyrate Using Transformant Escherichia coli BL21(DE3)+pET 23(a)-Omp-CRS (CRS, Sequence ID No 1) or C41(DE3)+pET 23(a)-Omp-CRS (CRS, Sequence ID No 1) as Biocatalyst The reaction was done in 2-phase system using dibutyl ether as co-solvent in an autotitrator (718 STAT Titrino, Metrohm, Switzerland). Escherichia coli BL21(DE3)+pET 23(a)-omp-CRS cells or C41(DE3)+pET 23(a)-omp-CRS (1.38 g; dry cell weight basis) were suspended in 20 ml phosphate buffer, 100 mM, pH 6.5. Glucose (9 g, 50 mmol), glucose dehydrogenase (3600 U), nicotinamide adenine dinucleotide phosphate (NADP) (18 mg, 0.02 mmol) and ECOB (6 g, 36.5 mmol) in 15 ml dibutyl ether were added to the suspension and contents gently stirred on magnetic stirrer at 30° C. The pH of the reaction was maintained at 6.5 with 5 M NaOH. The progress of the reaction was monitored at one hr interval as follows. An aliquots of 0.2 ml each was withdrawn and extracted with 2 ml of ethyl acetate. The organic phase was separated by centrifugation, dried over sodium sulphate and solvents removed to leave a residue, which was analyzed by $^1$H NMR. In $^1$H NMR methylene group corresponding to CH$_2$Cl in ECOB appeared as a singlet at δ 3.65, whereas it appeared as dd at 3.60 in reduced product ECHB. Since, these peaks appear in well resolved segment of $^1$H NMR, their relative concentrations in the mixture of two compounds can be easily calculated by comparing the relative integral values of the resonance at δ 3.60 and 3.65.

When the reaction mixture showed absence of the starting material, contents were extracted in ethyl acetate. The organic phase was separated by centrifugation, dried over sodium sulphate and solvents removed to give ethyl (S)-4-chloro-3-hydroxybutyrate. The optical purity of ethyl (S)-4-chloro-3-hydroxybutyrate is measured by high performance liquid chromatography by using Chiracel OB-H, product of Daicel Chemical Industries; eluent: hexane/isopropanol=96/4; flow rate: 1 ml/min; detection: 217 nm; column temperature: room temperature.

Example 13

Production of Ethyl (S)-4-Chloro-3-Hydroxybutyrate Using Transformant Escherichia coli BL21(DE3)+pET Duet1-omp-CRS, omp-GDH (CRS, Sequence ID No 1; GDH, Sequence ID No 9) or *Escherichia coli* C41(DE3)+pET Duet1-omp-CRS, omp-GDH (CRS, Sequence ID No 1; GDH, Sequence ID No 9) as Biocatalyst The production method was same as described in Example 12 except that no glucose dehydrogenase was added to the reaction.

We claim:

1. A designer cell that expresses a non-naturally occurring carbonyl reductase polypeptide of sequence SEQ ID NO: 1 of the Sequence Listing on the surface of cell having 250-fold to 300-fold higher activity per unit mass of CRS polypeptide compared to the designer cell that expresses corresponding carbonyl reductase of SEQ ID NO: 13 or 15 or 17 or 19 of the sequence listing in cytoplasm of cell for conversion of ethyl 4-chloro-3-oxobutyrate of formula 1 to ethyl s-4-chloro-3-hydroxybutyrate of formula 2.

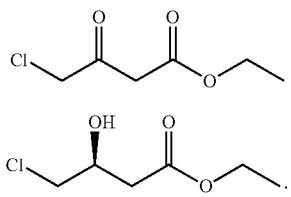

Formula 1

Formula 2

2. A designer cell as claimed in claim 1 that expresses a non-naturally occurring carbonyl reductase polypeptide of sequence SEQ ID NO: 1 of the Sequence Listing on the surface of cell having 15-fold to 26-fold higher activity per unit cell mass compared to the designer cell that expresses corresponding carbonyl reductase of SEQ ID NO: 13 or 15 or 17 or 19 of the Sequence Listing in cytoplasm of cell for conversion of ethyl 4-chloro-3-oxobutyrate of formula 1 to ethyl s-4-chloro-3-hydroxybutyrate of formula 2.

3. A designer cell as claimed in claim 1 that expresses a non-naturally occurring carbonyl reductase polypeptide of SEQ ID NO: 1 of the Sequence Listing on the surface of cell having 50-fold to 275-fold higher activity per unit mass of CRS polypeptide compared to the designer cell that expresses corresponding carbonyl reductase of SEQ ID NO: 13 of the Sequence Listing in cytoplasm of cell for reduction of compound of formula 3

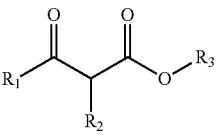

Formula 3 wherein R1=CH3, CH2X, (CH3)2CH, CF3 or CH3(CH2)n
R2=H, X or CH3(CH2)n;
R3=alkyl group such as CH3 or CH3(CH2)m;
X=Cl or Br;
n=1-4 and
m=1-8.

4. A designer cell as claimed in claim 1 that expresses a non-naturally occurring carbonyl reductase polypeptide of SEQ ID NO: 1 of the Sequence Listing on the surface of cell having 50-fold to 180-fold higher activity per unit mass of CRS polypeptide compared to the designer cell that expresses corresponding carbonyl reductase of SEQ ID NO: 13 of the Sequence Listing in cytoplasm of cell for reduction of compound of formula 4

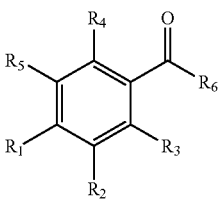

Formula 4 wherein R1=R2=R3=R4=R5=H, CH3, F, Cl, Br, I, CF3, NO2 or OCH3;
R6=alkyl group such as CH3 or CH3(CH2)n;
n=1 to 5.

5. A designer cell as claimed in claim 1 that expresses a non-naturally occurring carbonyl reductase polypeptide of SEQ ID NO: 1 of the Sequence Listing on the surface of cell having about 3-fold to 15-fold higher activity per unit cell mass compared to the designer cell that expresses corresponding carbonyl reductase of SEQ ID NO: 13 in cytoplasm of cell for reduction of compound of formula 3 or compound of formula 4

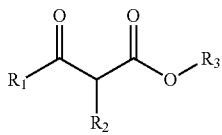

Formula 3 wherein R1=CH3, CH2X, (CH3)2CH, CF3 or CH3(CH2)n
R2=H, X or CH3(CH2)n;
R3=alkyl group such as CH3 or CH3(CH2)m;
X=Cl or Br;
n=1-4 and
m=1-8;

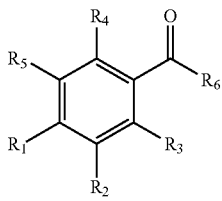

Formula 4 wherein R1=R2=R3=R4=R5=H, CH3, F, Cl, Br, I, CF3, NO2 or OCH3;
R6=alkyl group such as CH3 or CH3(CH2)n;
n=1 to 5.

6. A designer cell that simultaneously expresses a non-naturally occurring CRS polypeptide of sequence SEQ ID NO: 1 and a non-naturally occurring GDH polypeptide of sequence SEQ ID NO: 9 of the Sequence Listing on the surface of cell that has 250-fold to 300-fold higher activity for conversion of ethyl 4-chloro-3-oxobutyrate of formula 1 to ethyl s-4-chloro-3-hydroxybutyrate of formula 2 per unit mass of CRS polypeptide and 200-fold to 250-fold enhanced activity for oxidation of glucose to gluconate per unit mass of GDH polypeptide compared to the designer cell that simultaneously expresses corresponding CRS of SEQ ID NO: 13 or 15 or 17 or 19 of the Sequence Listing and corresponding GDH of SEQ ID NO: 21 or 23 of the Sequence Listing in cytoplasm of cell.

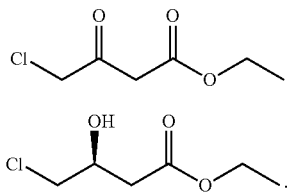

Formula 1

Formula 2

7. A designer cell as claimed in claim 6 that simultaneously expresses a non-naturally occurring CRS polypeptide of sequence SEQ ID NO: 1 and a non-naturally occurring GDH polypeptide of sequence SEQ ID NO: 9 of the Sequence Listing on the surface of cell that has about 11-fold to 24-fold higher activity for conversion of ethyl 4-chloro-3-oxobutyrate of formula 1 to ethyl s-4-chloro-3-hydroxybutyrate of formula 2 per unit cell mass and 9-fold to 31-fold enhanced activity for oxidation of glucose to gluconate per unit cell mass compared to the designer cell that simultaneously expresses corresponding CRS of SEQ ID NO: 13 or 15 or 17 or 19 of the Sequence Listing and corresponding GDH of SEQ ID NO: 21 or 23 of the Sequence Listing in cytoplasm of cell.

8. A designer cell as claimed in claim 6 that simultaneously expresses a non-naturally occurring CRS polypeptide of SEQ ID NO: 1 and a non-naturally occurring GDH polypeptide of SEQ ID NO: 9 of the Sequence Listing on the surface of cell having about 55-fold to 270-fold higher activity per unit mass of CRS polypeptide compared to the designer cell that simultaneously expresses corresponding CRS of SEQ ID NO: 13 of the Sequence Listing and corresponding GDH of SEQ ID NO: 21 of the Sequence Listing in cytoplasm of cell for reduction of compound of formula 3

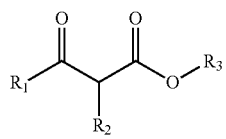

Formula 3 wherein R1=CH3, CH2X, (CH3)2CH, CF3 or CH3(CH2)n
R2=H, X or CH3(CH2)n;
R3=alkyl group such as CH3 or CH3(CH2)m;
X=Cl or Br;
n=1-4 and
m=1-8.

9. A designer cell as claimed in claim 6 that simultaneously expresses a non-naturally occurring CRS polypeptide of SEQ ID NO: 1 and a non-naturally occurring GDH polypeptide of SEQ ID NO: 9 of the Sequence Listing on the surface of cell having about 40-fold to 156-fold higher activity per unit mass of CRS polypeptide compared to the designer cell that simultaneously expresses corresponding CRS of SEQ ID NO: 13 of the Sequence Listing and corresponding GDH of SEQ ID NO: 21 of the Sequence Listing in cytoplasm of cell for reduction of compound of formula 4

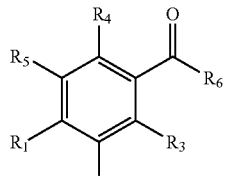

Formula 4 wherein R1=R2=R3=R4=R5=H, CH3, F, Cl, Br, I, CF3, NO2 or OCH3;
R6=alkyl group such as CH3 or CH3(CH2)n;
n=1 to 5.

10. A designer cell as claimed in claim 6 that simultaneously expresses a non-naturally occurring CRS polypeptide of SEQ ID NO: 1 and a non-naturally occurring GDH polypeptide of SEQ ID NO: 9 of the Sequence Listing on the surface of cell having about 3-fold to 24-fold higher activity per unit cell mass compared to the designer cell that simultaneously expresses corresponding CRS of SEQ ID NO: 13 of the Sequence Listing and corresponding GDH of SEQ ID NO: 21 of the Sequence Listing in cytoplasm of cell for reduction of compound of compound of formula 3 or compound of formula 4

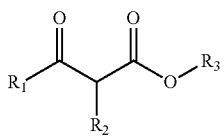

Formula 3 wherein R1=CH3, CH2X, (CH3)2CH, CF3 or CH3(CH2)n;
R2=H, X or CH3(CH2)n;
R3=alkyl group such as CH3 or CH3(CH2)m;
X=Cl or Br;
n=1-4 and
m=1-8

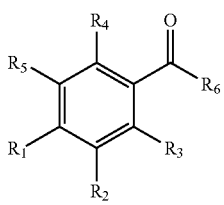

Formula 4 wherein R1=R2=R3=R4=R5=H, CH3, F, Cl, Br, I, CF3, NO2 or OCH3;
R6=alkyl group such as CH3 or CH3(CH2)n;
n=1 to 5.

11. A designer cell as claimed in claim 1, wherein designer cell is recombinant *Escherichia coli* BL21(DE3) or recombinant *Escherichia coli* C41(DE3) or recombinant *Escherichia coli* C43(DE3).

12. A recombinant expression vector of designer cell as claimed in claim 1, comprising polynucleotide encoding the polypeptide having the amino acid sequence of SEQ ID NO 1 showing carbonyl reductase activity.

13. A recombinant expression vector of designer cell as claimed in claim 6, comprising polynucleotides encoding the polypeptide having the amino acid sequence of SEQ ID NO 1 showing carbonyl reductase activity and the polypeptide having the amino acid sequence of SEQ ID NO 9 or 11 showing GDH activity.

14. A process for production of optically enriched aryl alcohols comprising steps of: a. providing a ketone having formula 1, formula 3 or formula 4 b. contacting said ketone with the designer cell of claim 1 and 0.005 to 0.02 mol % nicotinamide adenine dinucleotide phosphate, reduced (NADPH) and 100 to 500 units glucose dehydrogenase and a buffer solution of pH 5.0 to 9.0 to form a reaction mixture;

c. adding to the reaction mixture obtained in step (b) an organic solvent such as ethyl acetate, butyl acetate, diethylether, methyl n-butyl ether or di-n-butyl ether in the ratio ranging between 10:1 to 1:1;
d. energetically mixing the reaction mixture on magnetic stirrer at constant temperature of 20 to 40° C.;
e. extracting the product obtained in step (d) in ethyl acetate followed by isolating the product having formula 2, formula 5 or formula 6 respectively wherein Formula 2 is in about 100% enantiomeric excess,

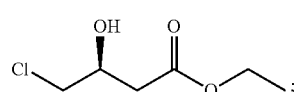

Formula 2

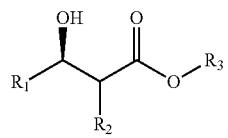

Formula 5 wherein R1=CH3, CH2X, (CH3)2CH, CF3 or CH3(CH2)n;
R2=H, X or CH3(CH2)n;
R3=alkyl group such as CH3 or CH3(CH2)m;
X=Cl or Br;
n=1-4 and
m=1-8;
or

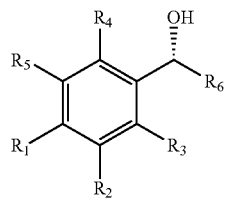

Formula 6 wherein R1=R2=R3=R4=R5=H, CH3, F, Cl, Br, I, CF3, NO2 or OCH3;
R6=alkyl group such as CH3 or CH3(CH2)n;
n=1 to 5.

15. Designer cells as claimed in claim 1 having Accession No. MTCC No. 5806, MTCC No. 5807, MTCC No. 5808 and MTCC No. 5809.

16. A designer cell as claimed in claim 6, wherein designer cell is recombinant *Escherichia coli* BL21(DE3) or recombinant *Escherichia coli* C41(DE3) or recombinant *Escherichia coli* C43(DE3).

17. Designer cells as claimed in claim 6 having Accession No. MTCC No. 5810, MTCC No. 5811, MTCC No. 5812, MTCC No. 5813; MTCC No. 5814. MTCC No. 5815, MTCC No. 5816 and MTCC No. 5817.

* * * * *

```
                       SEQUENCE LISTING

<160> NUMBER OF SEQ ID NOS: 32

<210> SEQ ID NO 1
<211> LENGTH: 432
<212> TYPE: PRT
<213> ORGANISM: Artificial Sequence
<220> FEATURE:
<223> OTHER INFORMATION: omp-crs (wild type) fusion
<220> FEATURE:
<221> NAME/KEY: VARIANT
<222> LOCATION: (21)..(432)

<400> SEQUENCE: 1

Met Lys Ala Thr Lys Leu Val Leu Gly Ala Val Ile Leu Gly Ser Thr
 1               5                  10                  15

Leu Leu Ala Gly Cys Ser Ser Asn Ala Lys Ile Asp Gln Gly Ile Asn
            20                  25                  30

Pro Tyr Val Gly Phe Glu Met Gly Tyr Asp Trp Leu Gly Arg Met Pro
        35                  40                  45

Tyr Lys Gly Ser Val Glu Asn Gly Ala Tyr Lys Ala Gln Gly Val Gln
    50                  55                  60

Leu Thr Ala Lys Leu Gly Tyr Pro Ile Thr Asp Asp Leu Asp Ile Tyr
65                  70                  75                  80

Thr Arg Leu Gly Gly Met Val Trp Arg Ala Asp Thr Lys Ser Asn Val
                85                  90                  95

Tyr Gly Lys Asn His Asp Thr Gly Val Ser Pro Val Phe Ala Gly Gly
            100                 105                 110

Val Glu Tyr Ala Ile Thr Pro Glu Ile Ala Thr Arg Leu Glu Tyr Gln
        115                 120                 125

Trp Thr Asn Asn Ile Gly Asp Ala His Thr Ile Gly Thr Arg Pro Asp
    130                 135                 140

Asn Gly Ile Pro Gly Met Ala Lys Asn Phe Ser Asn Val Glu Tyr Pro
145                 150                 155                 160

Ala Pro Pro Pro Ala His Thr Lys Asn Glu Ser Leu Gln Val Leu Asp
                165                 170                 175

Leu Phe Lys Leu Asn Gly Lys Val Ala Ser Ile Thr Gly Ser Ser Ser
            180                 185                 190

Gly Ile Gly Tyr Ala Leu Ala Glu Ala Phe Ala Gln Val Gly Ala Asp
        195                 200                 205

Val Ala Ile Trp Tyr Asn Ser His Asp Ala Thr Gly Lys Ala Glu Ala
    210                 215                 220

Leu Ala Lys Lys Tyr Gly Val Lys Val Lys Ala Tyr Lys Ala Asn Val
225                 230                 235                 240

Ser Ser Ser Asp Ala Val Lys Gln Thr Ile Glu Gln Gln Ile Lys Asp
                245                 250                 255

Phe Gly His Leu Asp Ile Val Val Ala Asn Ala Gly Ile Pro Trp Thr
            260                 265                 270

Lys Gly Ala Tyr Ile Asp Gln Asp Asp Lys His Phe Asp Gln Val
        275                 280                 285

Val Asp Val Asp Leu Lys Gly Val Gly Tyr Val Ala Lys His Ala Gly
    290                 295                 300

Arg His Phe Arg Glu Arg Phe Glu Lys Glu Gly Lys Lys Gly Ala Leu
305                 310                 315                 320
```

```
Val Phe Thr Ala Ser Met Ser Gly His Ile Val Asn Val Pro Gln Phe
            325                 330                 335

Gln Ala Thr Tyr Asn Ala Ala Lys Ala Gly Val Arg His Phe Ala Lys
            340                 345                 350

Ser Leu Ala Val Glu Phe Ala Pro Phe Ala Arg Val Asn Ser Val Ser
            355                 360                 365

Pro Gly Tyr Ile Asn Thr Glu Ile Ser Asp Phe Val Pro Gln Glu Thr
            370                 375                 380

Gln Asn Lys Trp Trp Ser Leu Val Pro Leu Gly Arg Gly Gly Glu Thr
385                 390                 395                 400

Ala Glu Leu Val Gly Ala Tyr Leu Phe Leu Ala Ser Asp Ala Gly Ser
            405                 410                 415

Tyr Ala Thr Gly Thr Asp Ile Ile Val Asp Gly Gly Tyr Thr Leu Pro
            420                 425                 430

<210> SEQ ID NO 2
<211> LENGTH: 1299
<212> TYPE: DNA
<213> ORGANISM: Artificial Sequence
<220> FEATURE:
<223> OTHER INFORMATION: omp-crs (wild type) fusion
<220> FEATURE:
<221> NAME/KEY: variation
<222> LOCATION: (1)..(1296)

<400> SEQUENCE: 2
atgaaagcta ctaaactggt actgggtgcc gtcatcctgg gctcaacgct gctggcgggc        60
tgctcgtcaa atgcgaaaat cgatcaaggt atcaatccgt atgtcggctt gaaatgggca       120
tatgattggc tgggtcgtat gccgtacaaa ggcagcgttg aaaacggtgc ctataaagca       180
cagggcgtcc aactgaccgc gaaactgggt tatccgatta ccgatgacct ggatatctac       240
acgcgtctgg gcggtatggt gtggcgtgca gacaccaaaa gtaacgttta cggcaaaaat       300
catgatacgg tgtttccccc ggtctttgcc ggcggtgtgg aatatgcaat taccccggaa       360
atcgctacgc gtctggaata ccagtggacc aacaatattg cgacgcaca taccatcggt        420 acgcgcccgg ataatggcat tccgggtatg gcgaaaaact tctctaatgt ggaatatccg       480
gcaccgccgc cggcacacac caaaaacgaa agcctgcaag tgctggatct gtttaaactg       540
aatggcaaag ttgcgtctat tacgggtagc tctagtggca tcggttatgc gctggccgaa       600
gcattcgctc aagttggcgc tgacgtcgcg atttggtaca acagccacga tgcgaccggc       660 aaaagcggaag cgctggcgaa aaatatggt gttaaagtca aagcctacaa agcaaatgtc        720
tcctcatcgg atgccgtgaa acagaccatt gaacagcaaa tcaaagactt ggccatctg        780 gatattgtgg ttgctaacgc gggcatcccg tggacgaagg tgcgtatat tgaccaggat        840 gacgataaac acttcgatca agtcgtggac gtggatctga aaggcgtggg ttacgttgct       900
aaacatgcgg tcgtcacttt cgtgaacgc ttcgaaaaag aaggcaaaaa aggtgccctg        960 gttttttaccg catcaatgtc gggccatatc gtgaacgttc cgcagttcca agccacgtat       1020
aatgcggcca agcaggtgt ccgtcacttt gctaaaagtc tggcggtgga atttgccccg        1080
ttcgcacgcg tcaacagcgt gtctccgggc tacatcaaca ccgaaatctc agatttcgtt       1140
ccgcaggaaa cgcaaaataa atggtggtcg ctggtcccgc tgggtcgcgg cggtgaaacc       1200
gctgaactgg ttggtgcgta tctgttcctg gcttcagacg caggctcgta cgcgaccggt       1260
acggacatta tcgtggatgg cggttatacg ctgccgtaa                             1299
```

<210> SEQ ID NO 3
<211> LENGTH: 432
<212> TYPE: PRT
<213> ORGANISM: Artificial Sequence
<220> FEATURE:
<223> OTHER INFORMATION: omp-crs (mutant; P14A, S42N, A194V, I275V) fusion
<220> FEATURE:
<221> NAME/KEY: VARIANT
<222> LOCATION: (21)..(432)

<400> SEQUENCE: 3

```
Met Lys Ala Thr Lys Leu Val Leu Gly Ala Val Ile Leu Gly Ser Thr
1               5                   10                  15

Leu Leu Ala Gly Cys Ser Ser Asn Ala Lys Ile Asp Gln Gly Ile Asn
            20                  25                  30

Pro Tyr Val Gly Phe Glu Met Gly Tyr Asp Trp Leu Gly Arg Met Pro
        35                  40                  45

Tyr Lys Gly Ser Val Glu Asn Gly Ala Tyr Lys Ala Gln Gly Val Gln
    50                  55                  60

Leu Thr Ala Lys Leu Gly Tyr Pro Ile Thr Asp Asp Leu Asp Ile Tyr
65                  70                  75                  80

Thr Arg Leu Gly Gly Met Val Trp Arg Ala Asp Thr Lys Ser Asn Val
                85                  90                  95

Tyr Gly Lys Asn His Asp Thr Gly Val Ser Pro Val Phe Ala Gly Gly
            100                 105                 110

Val Glu Tyr Ala Ile Thr Pro Glu Ile Ala Thr Arg Leu Glu Tyr Gln
        115                 120                 125

Trp Thr Asn Asn Ile Gly Asp Ala His Thr Ile Gly Thr Arg Pro Asp
    130                 135                 140

Asn Gly Ile Pro Gly Met Ala Lys Asn Phe Ser Asn Val Glu Tyr Pro
145                 150                 155                 160

Ala Pro Ala Pro Ala His Thr Lys Asn Glu Ser Leu Gln Val Leu Asp
                165                 170                 175

Leu Phe Lys Leu Asn Gly Lys Val Ala Ser Ile Thr Gly Ser Asn Ser
            180                 185                 190

Gly Ile Gly Tyr Ala Leu Ala Glu Ala Phe Ala Gln Val Gly Ala Asp
        195                 200                 205

Val Ala Ile Trp Tyr Asn Ser His Asp Ala Thr Gly Lys Ala Glu Ala
    210                 215                 220

Leu Ala Lys Lys Tyr Gly Val Lys Val Lys Ala Tyr Lys Ala Asn Val
225                 230                 235                 240

Ser Ser Ser Asp Ala Val Lys Gln Thr Ile Glu Gln Ile Lys Asp
                245                 250                 255

Phe Gly His Leu Asp Ile Val Val Asn Ala Gly Ile Pro Trp Thr
            260                 265                 270

Lys Gly Ala Tyr Ile Asp Gln Asp Asp Lys His Phe Asp Gln Val
        275                 280                 285

Val Asp Val Asp Leu Lys Gly Val Gly Tyr Val Ala Lys His Ala Gly
    290                 295                 300

Arg His Phe Arg Glu Arg Phe Glu Lys Glu Gly Lys Lys Gly Ala Leu
305                 310                 315                 320

Val Phe Thr Ala Ser Met Ser Gly His Ile Val Asn Val Pro Gln Phe
                325                 330                 335

Gln Ala Thr Tyr Asn Ala Val Lys Ala Gly Val Arg His Phe Ala Lys
            340                 345                 350
```

Ser Leu Ala Val Glu Phe Ala Pro Phe Ala Arg Val Asn Ser Val Ser
            355                 360                 365

Pro Gly Tyr Ile Asn Thr Glu Ile Ser Asp Phe Val Pro Gln Glu Thr
        370                 375                 380

Gln Asn Lys Trp Trp Ser Leu Val Pro Leu Gly Arg Gly Gly Glu Thr
385                 390                 395                 400

Ala Glu Leu Val Gly Ala Tyr Leu Phe Leu Ala Ser Asp Ala Gly Ser
            405                 410                 415

Tyr Ala Thr Gly Thr Asp Ile Val Val Asp Gly Gly Tyr Thr Leu Pro
            420                 425                 430

<210> SEQ ID NO 4
<211> LENGTH: 1299
<212> TYPE: DNA
<213> ORGANISM: Artificial Sequence
<220> FEATURE:
<223> OTHER INFORMATION: omp-crs (mutant; P14A, S42N, A194V, I275V)
      fusion
<220> FEATURE:
<221> NAME/KEY: variation
<222> LOCATION: (1)..(1296)

<400> SEQUENCE: 4
atgaaagcta ctaaactggt actgggtgcc gtcatcctgg gctcaacgct gctggcgggc      60
tgctcgtcaa atgcgaaaat cgatcaaggt atcaatccgt atgtcggctt gaaatgggc     120
tatgattggc tgggtcgtat gccgtacaaa ggcagcgttg aaaacggtgc ctataaagca     180
cagggcgtcc aactgaccgc gaaactgggt tatccgatta ccgatgacct ggatatctac     240
acgcgtctgg cggtatggt gtggcgtgca gacaccaaaa gtaacgttta cggcaaaaat     300
catgatacgg tgtttcccc ggtctttgcc ggcggtgtgg aatatgcaat taccccggaa     360
atcgctacgc gtctggaata ccagtggacc aacaatattg gcgacgcaca ccatcggt     420
acgcgcccgg ataatggcat tccgggtatg gcgaaaaact ctctaatgt ggaatatcca     480
gcaccggcgc cggcacacac caaaaacgaa agcctgcaag tgctggatct gtttaaactg     540
aatggcaaag ttgcgtctat cacgggtagc aatagtggta tcggttatgc gctggccgaa     600
gcattcgctc aagttggcgc tgacgtcgcg atttggtaca acagccacga tgcgaccggc     660
aaagcggaag cgctggcgaa aaatatggt gttaaagtca aagcctacaa agcaaatgtc     720
tcctcatcgg atgccgtgaa acagaccatt gaacagcaaa tcaaagactt ggccatctg     780
gatattgtgg ttgctaacgc gggcatcccg tggacgaagg gtgcgtatat tgaccaggat     840
gacgataaac acttcgatca agtcgtggac gtggatctga aaggcgtggg ttacgttgct     900
aaacatgcgg tcgtcacttt cgtgaacgc ttcgaaaaag aaggcaaaaa aggtgccctg     960
gtttttaccg catcaatgtc gggccatatc gtgaacgttc cgcagttcca agccacgtat    1020
aacgcagtca agcaggtgt ccgtcacttt gctaaaagtc tggcggtgga atttgccccg    1080
ttcgcacgcg tcaacagcgt gtctccgggc tacatcaaca ccgaaatctc agatttcgtt    1140
ccgcaggaaa cgcaaaataa atggtggtcg ctggtcccgc tgggtcgcgg cggtgaaacc    1200
gctgaactgg ttggtgcgta tctgttcctg gcttcagacg caggctcgta cgcgaccggt    1260
acggacattg tcgtggatgg cggttatacg ctgccgtaa                          1299

<210> SEQ ID NO 5
<211> LENGTH: 432
<212> TYPE: PRT
<213> ORGANISM: Artificial Sequence -continued

```
<220> FEATURE:
<223> OTHER INFORMATION: omp-crs (mutant; P14A, S42N, V147A, A194V,
      E234G) fusion
<220> FEATURE:
<221> NAME/KEY: VARIANT
<222> LOCATION: (21)..(432)

<400> SEQUENCE: 5
```

| | | | | | | | | | | | | | | |
|---|---|---|---|---|---|---|---|---|---|---|---|---|---|---|
| Met | Lys | Ala | Thr | Lys | Leu | Val | Leu | Gly | Ala | Val | Ile | Leu | Gly | Ser | Thr |
| 1 | | | | 5 | | | | | 10 | | | | | 15 | |

| Leu | Leu | Ala | Gly | Cys | Ser | Ser | Asn | Ala | Lys | Ile | Asp | Gln | Gly | Ile | Asn |
|---|---|---|---|---|---|---|---|---|---|---|---|---|---|---|---|
| | | | 20 | | | | | 25 | | | | | 30 | | |

| Pro | Tyr | Val | Gly | Phe | Glu | Met | Gly | Tyr | Asp | Trp | Leu | Gly | Arg | Met | Pro |
|---|---|---|---|---|---|---|---|---|---|---|---|---|---|---|---|
| | | | 35 | | | | | 40 | | | | | 45 | | |

| Tyr | Lys | Gly | Ser | Val | Glu | Asn | Gly | Ala | Tyr | Lys | Ala | Gln | Gly | Val | Gln |
|---|---|---|---|---|---|---|---|---|---|---|---|---|---|---|---|
| | 50 | | | | | 55 | | | | | 60 | | | | |

| Leu | Thr | Ala | Lys | Leu | Gly | Tyr | Pro | Ile | Thr | Asp | Asp | Leu | Asp | Ile | Tyr |
|---|---|---|---|---|---|---|---|---|---|---|---|---|---|---|---|
| 65 | | | | | 70 | | | | | 75 | | | | | 80 |

| Thr | Arg | Leu | Gly | Gly | Met | Val | Trp | Arg | Ala | Asp | Thr | Lys | Ser | Asn | Val |
|---|---|---|---|---|---|---|---|---|---|---|---|---|---|---|---|
| | | | | 85 | | | | | 90 | | | | | 95 | |

| Tyr | Gly | Lys | Asn | His | Asp | Thr | Gly | Val | Ser | Pro | Val | Phe | Ala | Gly | Gly |
|---|---|---|---|---|---|---|---|---|---|---|---|---|---|---|---|
| | | | 100 | | | | | 105 | | | | | 110 | | |

| Val | Glu | Tyr | Ala | Ile | Thr | Pro | Glu | Ile | Ala | Thr | Arg | Leu | Glu | Tyr | Gln |
|---|---|---|---|---|---|---|---|---|---|---|---|---|---|---|---|
| | | 115 | | | | | 120 | | | | | 125 | | | |

| Trp | Thr | Asn | Asn | Ile | Gly | Asp | Ala | His | Thr | Ile | Gly | Thr | Arg | Pro | Asp |
|---|---|---|---|---|---|---|---|---|---|---|---|---|---|---|---|
| | 130 | | | | | 135 | | | | | 140 | | | | |

| Asn | Gly | Ile | Pro | Gly | Met | Ala | Lys | Asn | Phe | Ser | Asn | Val | Glu | Tyr | Pro |
|---|---|---|---|---|---|---|---|---|---|---|---|---|---|---|---|
| 145 | | | | | 150 | | | | | 155 | | | | | 160 |

| Ala | Pro | Ala | Pro | Ala | His | Thr | Lys | Asn | Glu | Ser | Leu | Gln | Val | Leu | Asp |
|---|---|---|---|---|---|---|---|---|---|---|---|---|---|---|---|
| | | | | 165 | | | | | 170 | | | | | 175 | |

| Leu | Phe | Lys | Leu | Asn | Gly | Lys | Val | Ala | Ser | Ile | Thr | Gly | Ser | Asn | Ser |
|---|---|---|---|---|---|---|---|---|---|---|---|---|---|---|---|
| | | | 180 | | | | | 185 | | | | | 190 | | |

| Gly | Ile | Gly | Tyr | Ala | Leu | Ala | Glu | Ala | Phe | Ala | Gln | Val | Gly | Ala | Asp |
|---|---|---|---|---|---|---|---|---|---|---|---|---|---|---|---|
| | | | 195 | | | | | 200 | | | | | 205 | | |

| Val | Ala | Ile | Trp | Tyr | Asn | Ser | His | Asp | Ala | Thr | Gly | Lys | Ala | Glu | Ala |
|---|---|---|---|---|---|---|---|---|---|---|---|---|---|---|---|
| | 210 | | | | | 215 | | | | | 220 | | | | |

| Leu | Ala | Lys | Lys | Tyr | Gly | Val | Lys | Val | Lys | Ala | Tyr | Lys | Ala | Asn | Val |
|---|---|---|---|---|---|---|---|---|---|---|---|---|---|---|---|
| 225 | | | | | 230 | | | | | 235 | | | | | 240 |

| Ser | Ser | Ser | Asp | Ala | Val | Lys | Gln | Thr | Ile | Glu | Gln | Gln | Ile | Lys | Asp |
|---|---|---|---|---|---|---|---|---|---|---|---|---|---|---|---|
| | | | | 245 | | | | | 250 | | | | | 255 | |

| Phe | Gly | His | Leu | Asp | Ile | Val | Val | Ala | Asn | Ala | Gly | Ile | Pro | Trp | Thr |
|---|---|---|---|---|---|---|---|---|---|---|---|---|---|---|---|
| | | | 260 | | | | | 265 | | | | | 270 | | |

| Lys | Gly | Ala | Tyr | Ile | Asp | Gln | Asp | Asp | Asp | Lys | His | Phe | Asp | Gln | Val |
|---|---|---|---|---|---|---|---|---|---|---|---|---|---|---|---|
| | | | 275 | | | | | 280 | | | | | 285 | | |

| Val | Asp | Val | Asp | Leu | Lys | Gly | Ala | Gly | Tyr | Val | Ala | Lys | His | Ala | Gly |
|---|---|---|---|---|---|---|---|---|---|---|---|---|---|---|---|
| | 290 | | | | | 295 | | | | | 300 | | | | |

| Arg | His | Phe | Arg | Glu | Arg | Phe | Glu | Lys | Glu | Gly | Lys | Lys | Gly | Ala | Leu |
|---|---|---|---|---|---|---|---|---|---|---|---|---|---|---|---|
| 305 | | | | | 310 | | | | | 315 | | | | | 320 |

| Val | Phe | Thr | Ala | Ser | Met | Ser | Gly | His | Ile | Val | Asn | Val | Pro | Gln | Phe |
|---|---|---|---|---|---|---|---|---|---|---|---|---|---|---|---|
| | | | | 325 | | | | | 330 | | | | | 335 | |

| Gln | Ala | Thr | Tyr | Asn | Ala | Val | Lys | Ala | Gly | Val | Arg | His | Phe | Ala | Lys |
|---|---|---|---|---|---|---|---|---|---|---|---|---|---|---|---|
| | | | 340 | | | | | 345 | | | | | 350 | | |

| Ser | Leu | Ala | Val | Glu | Phe | Ala | Pro | Phe | Ala | Arg | Val | Asn | Ser | Val | Ser |
|---|---|---|---|---|---|---|---|---|---|---|---|---|---|---|---|
| | | | 355 | | | | | 360 | | | | | 365 | | |

| Pro | Gly | Tyr | Ile | Asn | Thr | Glu | Ile | Ser | Asp | Phe | Val | Pro | Gln | Glu | Thr |

Gln Asn Arg Trp Trp Ser Leu Val Pro Leu Gly Arg Gly Gly Glu Thr
    370             375                 380
Ala Glu Leu Val Gly Ala Tyr Leu Phe Leu Ala Ser Asp Ala Gly Ser
385                 390                 395                 400
Tyr Ala Thr Gly Thr Asp Ile Ile Val Asp Gly Gly Tyr Thr Leu Pro
            405                 410                 415
                420                 425                 430

<210> SEQ ID NO 6
<211> LENGTH: 1299
<212> TYPE: DNA
<213> ORGANISM: Artificial Sequence
<220> FEATURE:
<223> OTHER INFORMATION: omp-crs (mutant; P14A, S42N, V147A, A194V, E234G) fusion
<220> FEATURE:
<221> NAME/KEY: variation
<222> LOCATION: (1)..(1296)

<400> SEQUENCE: 6

```
atgaaagcta ctaaactggt actgggtgcc gtcatcctgg gctcaacgct gctggcgggc      60
tgctcgtcaa atgcgaaaat cgatcaaggt atcaatccgt atgtcggctt gaaatgggc     120
tatgattggc tgggtcgtat gccgtacaaa ggcagcgttg aaaacggtgc ctataaagca     180
cagggcgtcc aactgaccgc gaaactgggt tatccgatta ccgatgacct ggatatctac     240
acgcgtctgg gcggtatggt gtggcgtgca gacaccaaaa gtaacgttta cggcaaaaat     300
catgatacgg tgtttccccc ggtctttgcc ggcggtgtgg aatatgcaat taccccggaa     360
atcgctacgc gtctggaata ccagtggacc aacaatattg gcgacgcaca taccatcggt     420
acgcgcccgg ataatggcat tccgggtatg gcgaaaaact tctctaatgt ggaatatcca     480
gcaccggcgc cggcacacac caaaaacgaa agcctgcaag tgctggatct gttttaaactg     540
aatggcaaag ttgcgtctat cacgggtagc aatagtggta tcggttatgc gctggccgaa     600
gcattcgctc aagttggcgc tgacgtcgcg atttggtaca cagccacga tgcgaccggc     660
aaagcggaag cgctggcgaa aaatatggt gttaaagtca agcctacaa agcaaatgtc     720
tcctcatcgg atgccgtgaa acagaccatt gaacagcaaa tcaaagactt ggccatctg     780
gatattgtgg ttgctaacgc gggcatcccg tggacgaagg gtgcgtatat tgaccaggat     840
gacgataaac acttcgatca agtcgtggac gtggatctga aggcgcgggg ttacgttgct     900
aaacatgcgg tcgtcacttt cgtgaacgc ttcgaaaaag aaggcaaaaa aggtgccctg     960
gtttttaccg catcaatgtc gggccatatc gtgaacgttc cgcagttcca agccacgtat    1020
aacgcagtca agcaggtgt ccgtcacttt gctaaaagtc tggcggtgga atttgccccg    1080
ttcgcacgcg tcaacagcgt gtctccgggc tacatcaaca ccgaaatctc agatttcgtt    1140
ccgcaggaaa cgcaaaatag atggtggtcg ctggtcccgc tgggtcgcgg cggtgaaacc    1200
gctgaactgg ttggtgcgta tctgttcctg gcttcagacg caggctcgta cgcgaccggt    1260
acggacatta tcgtggatgg cggttatacg ctgccgtaa                           1299
```

<210> SEQ ID NO 7
<211> LENGTH: 432
<212> TYPE: PRT
<213> ORGANISM: Artificial Sequence
<220> FEATURE:
<223> OTHER INFORMATION: omp-crs (mutant; P14A, N20S, S42N, T190A, A194V, E234G) fusion
<220> FEATURE:
<221> NAME/KEY: VARIANT -continued

<222> LOCATION: (21)..(432)

<400> SEQUENCE: 7

```
Met Lys Ala Thr Lys Leu Val Leu Gly Ala Val Ile Leu Gly Ser Thr
 1               5                  10                  15

Leu Leu Ala Gly Cys Ser Ser Asn Ala Lys Ile Asp Gln Gly Ile Asn
             20                  25                  30

Pro Tyr Val Gly Phe Glu Met Gly Tyr Asp Trp Leu Gly Arg Met Pro
         35                  40                  45

Tyr Lys Gly Ser Val Glu Asn Gly Ala Tyr Lys Ala Gln Gly Val Gln
     50                  55                  60

Leu Thr Ala Lys Leu Gly Tyr Pro Ile Thr Asp Leu Asp Ile Tyr
 65                  70                  75                  80

Thr Arg Leu Gly Gly Met Val Trp Arg Ala Asp Thr Lys Ser Asn Val
                 85                  90                  95

Tyr Gly Lys Asn His Asp Thr Gly Val Ser Pro Val Phe Ala Gly Gly
            100                 105                 110

Val Glu Tyr Ala Ile Thr Pro Glu Ile Ala Thr Arg Leu Glu Tyr Gln
        115                 120                 125

Trp Thr Asn Asn Ile Gly Asp Ala His Thr Ile Gly Thr Arg Pro Asp
130                 135                 140

Asn Gly Ile Pro Gly Met Ala Lys Asn Phe Ser Asn Val Gly Tyr Pro
145                 150                 155                 160

Ala Pro Ala Pro Ala His Thr Lys Ser Glu Ser Leu Gln Val Leu Asp
                165                 170                 175

Leu Phe Lys Leu Asn Gly Lys Val Ala Ser Ile Thr Gly Ser Asn Ser
            180                 185                 190

Gly Ile Gly Tyr Ala Leu Ala Glu Ala Phe Ala Gln Val Gly Ala Asp
        195                 200                 205

Val Ala Ile Trp Tyr Asn Ser His Asp Ala Thr Gly Lys Ala Glu Ala
    210                 215                 220

Leu Ala Lys Lys Tyr Gly Val Lys Val Lys Ala Tyr Lys Ala Asn Val
225                 230                 235                 240

Ser Ser Ser Asp Ala Val Lys Gln Thr Ile Glu Gln Gln Ile Lys Asp
                245                 250                 255

Phe Gly His Leu Asp Ile Val Val Ala Asn Ala Gly Ile Pro Trp Thr
            260                 265                 270

Lys Gly Ala Tyr Ile Asp Gln Asp Asp Lys His Phe Asp Gln Val
        275                 280                 285

Val Asp Val Asp Leu Lys Gly Val Gly Tyr Val Ala Lys His Ala Gly
    290                 295                 300

Arg His Phe Arg Glu Arg Phe Glu Lys Glu Gly Lys Lys Gly Ala Leu
305                 310                 315                 320

Val Phe Thr Ala Ser Met Ser Gly His Ile Val Asn Val Pro Gln Phe
                325                 330                 335

Gln Ala Ala Tyr Asn Ala Val Lys Ala Gly Val Arg His Phe Ala Lys
            340                 345                 350

Ser Leu Ala Val Glu Phe Ala Pro Phe Ala Arg Val Asn Ser Val Ser
        355                 360                 365

Pro Gly Tyr Ile Asn Thr Glu Ile Ser Asp Phe Val Pro Gln Gly Thr
    370                 375                 380

Gln Asn Lys Trp Trp Ser Leu Val Pro Leu Gly Arg Gly Gly Glu Thr
385                 390                 395                 400
```

```
Ala Glu Leu Val Gly Ala Tyr Leu Phe Leu Ala Ser Asp Ala Gly Ser
            405                 410                 415

Tyr Ala Thr Gly Thr Asp Ile Ile Val Asp Gly Gly Tyr Thr Leu Pro
            420                 425                 430

<210> SEQ ID NO 8
<211> LENGTH: 1299
<212> TYPE: DNA
<213> ORGANISM: Artificial Sequence
<220> FEATURE:
<223> OTHER INFORMATION: omp-crs (mutant; P14A, N20S, S42N, T190A,
      A194V, E234G) fusion
<220> FEATURE:
<221> NAME/KEY: variation
<222> LOCATION: (1)..(1296)

<400> SEQUENCE: 8
atgaaagcta ctaaactggt actgggtgcc gtcatcctgg gctcaacgct gctggcgggc     60
tgctcgtcaa atgcgaaaat cgatcaaggt atcaatccgt atgtcggctt tgaaatgggc    120
tatgattggc tgggtcgtat gccgtacaaa ggcagcgttg aaaacggtgc ctataaagca    180
cagggcgtcc aactgaccgc gaaactgggt tatccgatta ccgatgacct ggatatctac    240
acgcgtctgg gcgtatggt gtggcgtgca gacaccaaaa gtaacgttta cggcaaaaat    300
catgatacgg tgtttccc ggtctttgcc ggcggtgtgg aatatgcaat taccccggaa     360
atcgctacgc gtctggaata ccagtggacc aacaatattg cgacgcaca taccatcggt    420 acgcgcccgg ataatggcat tccgggtatg ctaaaaact tttccaatgt cggatatcct    480
gccccggcgc cagctcatac caaaagcgaa tcactgcagg tactggatct gttcaaactg    540
aacggcaaag tcgcgtctat caccggtagc aactcaggca ttggttacgc gctggccgag    600
gcttttgcgc aggttggcgc agacgttgcg atctggtata cagccatga tgccaccggt    660 aaagcagagg ccctggctaa aaatatggc gtaaaagtca aggcttataa agctaatgtc    720
agttcgagtg atgcggtgaa acagactatt gagcagcaga tcaaggattt tggccacctg    780
gacatagttg tggcgaacgc aggcatcccc tggactaagg gtgcatacat cgatcaggat    840
gacgataaac ctttgacca ggtggttgac gtcgacctga aggcgtagg ctatgtagca    900 aaacatgcgg gtcgccattt tcgtgaacgt ttcgaaaaag aaggcaaaaa gggcgccttg    960
gtctttacgc cttccatgtc gggtcacatc gttaacgtgc cgcaatttca gcggcctac    1020 aatgcggtca aggcaggcgt gcgtcatttc gcaaagtccc tggccgtgga atttgctcct    1080
ttcgcacgtg ttaactctgt atctcctggc tatattaata ccgagatctc tgatttcgtc    1140
ccgcaaggaa cacagaataa atggtggagc ttagttccat gggccgtgg cggggaaact    1200 gcggaattag ttggtgccta cctgttcctg gcaagtgatg cgggctccta cgccacgggc    1260
acggatatca ttgtggacgg cggctacacg ctgccgtag                         1299

<210> SEQ ID NO 9
<211> LENGTH: 410
<212> TYPE: PRT
<213> ORGANISM: Artificial Sequence
<220> FEATURE:
<223> OTHER INFORMATION: omp-gdh (wild type) fusion
<220> FEATURE:
<221> NAME/KEY: VARIANT
<222> LOCATION: (21)..(410)

<400> SEQUENCE: 9

Met Lys Ala Thr Lys Leu Val Leu Gly Ala Val Ile Leu Gly Ser Thr
1               5                   10                  15
```

-continued

```
Leu Leu Ala Gly Cys Ser Ser Asn Ala Lys Ile Asp Gln Gly Ile Asn
         20                  25                  30
Pro Tyr Val Gly Phe Glu Met Gly Tyr Asp Trp Leu Gly Arg Met Pro
         35                  40                  45
Tyr Lys Gly Ser Val Glu Asn Gly Ala Tyr Lys Ala Gln Gly Val Gln
 50                  55                  60
Leu Thr Ala Lys Leu Gly Tyr Pro Ile Thr Asp Asp Leu Asp Ile Tyr
 65                  70                  75                  80
Thr Arg Leu Gly Gly Met Val Trp Arg Ala Asp Thr Lys Ser Asn Val
                 85                  90                  95
Tyr Gly Lys Asn His Asp Thr Gly Val Ser Pro Val Phe Ala Gly Gly
             100                 105                 110
Val Glu Tyr Ala Ile Thr Pro Glu Ile Ala Thr Arg Leu Glu Tyr Gln
             115                 120                 125
Trp Thr Asn Asn Ile Gly Asp Ala His Thr Ile Gly Thr Arg Pro Asp
130                 135                 140
Asn Gly Ile Pro Gly Met Tyr Lys Asp Leu Glu Gly Lys Val Val Val
145                 150                 155                 160
Ile Thr Gly Ser Ser Thr Gly Leu Gly Lys Ala Met Ala Ile Arg Phe
                165                 170                 175
Ala Thr Glu Lys Ala Lys Val Val Asn Tyr Arg Ser Lys Glu Glu
            180                 185                 190
Glu Ala Asn Ser Val Leu Glu Glu Ile Lys Lys Val Gly Gly Glu Ala
            195                 200                 205
Ile Ala Val Lys Gly Asp Val Thr Val Glu Ser Asp Val Ile Asn Leu
        210                 215                 220
Val Gln Ser Ser Ile Lys Glu Phe Gly Lys Leu Asp Val Met Ile Asn
225                 230                 235                 240
Asn Ala Gly Met Glu Asn Pro Val Ser Ser His Glu Met Ser Leu Ser
                245                 250                 255
Asp Trp Asn Lys Val Ile Asp Thr Asn Leu Thr Gly Ala Phe Leu Gly
            260                 265                 270
Ser Arg Glu Ala Ile Lys Tyr Phe Val Glu Asn Asp Ile Lys Gly Thr
        275                 280                 285
Val Ile Asn Met Ser Ser Val His Glu Lys Ile Pro Trp Pro Leu Phe
        290                 295                 300
Val His Tyr Ala Ala Ser Lys Gly Gly Met Lys Leu Met Thr Glu Thr
305                 310                 315                 320
Leu Ala Leu Glu Tyr Ala Pro Lys Gly Ile Arg Val Asn Asn Ile Gly
                325                 330                 335
Pro Gly Ala Ile Asn Thr Pro Ile Asn Ala Glu Lys Phe Ala Asp Pro
            340                 345                 350
Glu Gln Arg Ala Asp Val Glu Ser Met Ile Pro Met Gly Tyr Ile Gly
        355                 360                 365
Glu Pro Glu Glu Ile Ala Ala Val Ala Ala Trp Leu Ala Ser Ser Glu
    370                 375                 380
Ala Ser Tyr Val Thr Gly Ile Thr Leu Phe Ala Asp Gly Gly Met Thr
385                 390                 395                 400
Gln Tyr Pro Ser Phe Gln Ala Gly Arg Gly
                405                 410

<210> SEQ ID NO 10
<211> LENGTH: 1233
```

<212> TYPE: DNA
<213> ORGANISM: Artificial Sequence
<220> FEATURE:
<223> OTHER INFORMATION: omp-gdh (wild type) fusion
<220> FEATURE:
<221> NAME/KEY: variation
<222> LOCATION: (1)..(1230)

<400> SEQUENCE: 10

```
atgaaagcta cgaaactggt tctgggtgct gttattctgg gttcaacgct gctggcgggc    60
tgctcctcaa atgcgaaaat cgaccaaggc attaacccgt atgtgggctt gaaatgggt   120
tacgattggc tgggtcgtat gccgtataaa ggcagtgttg aaaatggtgc ctacaaagca   180
cagggcgtcc aactgaccgc aaaactgggt tatccgatta ccgatgacct ggatatctac   240
acgcgtctgg cggtatggt gtggcgtgca gataccaaaa gcaacgttta tgcaaaaat    300
catgacacgg tgttttctcc ggtctttgcg ggcggtgtgg aatatgccat tacccccggaa  360
atcgcaacgc gtctggaata ccagtggacc aacaatattg gtgacgcaca ccatcggt    420
acgcgtccgg ataacggcat tccgggcatg tataaagacc tggaaggcaa agtggttgtc   480
attaccggta gctctacggg cctgggtaaa gcgatggcca tccgttttgc taccgaaaaa   540
gcgaaagtgg ttgtcaacta ccgctcaaaa gaagaagaag cgaacagcgt gctggaagaa   600
atcaaaaaag ttggcggtga agcaatcgct gtcaaaggcg acgttacggt cgaaagcgat   660
gttattaacc tggtccagag ttccatcaaa gaatttggca aactggatgt catgattaac   720
aatgcgggta tggaaaatcc ggtgtcatcg catgaaatgt cactgtcgga ctggaacaaa   780
gtgattgata ccaatctgac gggcgctttt ctgggttcac gtgaagccat caaatacttc   840
gttgaaaacg atatcaaagg caccgtcatc aatatgagct ctgtgcatga aaaaatcccg   900
tggccgctgt ttgtgcacta tcggccagc aaaggcggta tgaaactgat gaccgaaacg   960
ctggccctgg aatacgcacc gaaaggtatt cgtgtgaaca atatcggccc gggtgcgatt  1020
aacaccccga tcaatgctga aaattcgcg gaccccggaac agcgcgccga tgttgaaagt  1080
atgattccga tgggctatat cggtgaaccg gaagaaattg cagctgttgc ggcctggctg  1140
gccagttccg aagcatccta tgtcaccggc atcacgctgt tgccgatgg cggtatgacc  1200
cagtacccga gcttccaagc aggtcgcggc taa                               1233
```

<210> SEQ ID NO 11
<211> LENGTH: 410
<212> TYPE: PRT
<213> ORGANISM: Artificial Sequence
<220> FEATURE:
<223> OTHER INFORMATION: omp-gdh (mutant; S16A, E170K, P194T, A197K, E222D, S237C) fusion
<220> FEATURE:
<221> NAME/KEY: VARIANT
<222> LOCATION: (21)..(410)

<400> SEQUENCE: 11

Met Lys Ala Thr Lys Leu Val Leu Gly Ala Val Ile Leu Gly Ser Thr
1               5                   10                  15

Leu Leu Ala Gly Cys Ser Ser Asn Ala Lys Ile Asp Gln Gly Ile Asn
            20                  25                  30

Pro Tyr Val Gly Phe Glu Met Gly Tyr Asp Trp Leu Gly Arg Met Pro
        35                  40                  45

Tyr Lys Gly Ser Val Glu Asn Gly Ala Tyr Lys Ala Gln Gly Val Gln
    50                  55                  60

Leu Thr Ala Lys Leu Gly Tyr Pro Ile Thr Asp Asp Leu Asp Ile Tyr

```
            65                  70                  75                  80
        Thr Arg Leu Gly Gly Met Val Trp Arg Ala Asp Thr Lys Ser Asn Val
                         85                  90                  95
        Tyr Gly Lys Asn His Asp Thr Gly Val Ser Pro Val Phe Ala Gly Gly
                        100                 105                 110
        Val Glu Tyr Ala Ile Thr Pro Glu Ile Ala Thr Arg Leu Glu Tyr Gln
                        115                 120                 125
        Trp Thr Asn Asn Ile Gly Asp Ala His Thr Ile Gly Thr Arg Pro Asp
                130                 135                 140
        Asn Gly Ile Pro Gly Met Tyr Lys Asp Leu Glu Gly Lys Val Val Val
        145                 150                 155                 160
        Ile Thr Gly Ser Ala Thr Gly Leu Gly Lys Ala Met Ala Ile Arg Phe
                        165                 170                 175
        Ala Thr Glu Lys Ala Lys Val Val Val Asn Tyr Arg Ser Lys Glu Glu
                        180                 185                 190
        Glu Ala Asn Ser Val Leu Glu Glu Ile Lys Lys Val Gly Gly Glu Ala
                        195                 200                 205
        Ile Ala Val Lys Gly Asp Val Thr Val Glu Ser Asp Val Ile Asn Leu
                210                 215                 220
        Val Gln Ser Ser Ile Lys Glu Phe Gly Lys Leu Asp Val Met Ile Asn
        225                 230                 235                 240
        Asn Ala Gly Met Glu Asn Pro Val Ser Ser His Glu Met Ser Leu Ser
                        245                 250                 255
        Asp Trp Asn Lys Val Ile Asp Thr Asn Leu Thr Gly Ala Phe Leu Gly
                        260                 265                 270
        Ser Arg Glu Ala Ile Lys Tyr Phe Val Glu Asn Asp Ile Lys Gly Thr
                        275                 280                 285
        Val Ile Asn Met Ser Ser Val His Glu Lys Ile Pro Trp Pro Leu Phe
                290                 295                 300
        Val His Tyr Ala Ala Ser Lys Gly Gly Met Lys Leu Met Thr Lys Thr
        305                 310                 315                 320
        Leu Ala Leu Glu Tyr Ala Pro Lys Gly Ile Arg Val Asn Asn Ile Gly
                        325                 330                 335
        Pro Gly Ala Ile Asn Thr Thr Ile Asn Lys Glu Lys Phe Ala Asp Pro
                        340                 345                 350
        Glu Gln Arg Ala Asp Val Glu Ser Met Ile Pro Met Gly Tyr Ile Gly
                        355                 360                 365
        Glu Pro Asp Glu Ile Ala Ala Val Ala Ala Trp Leu Ala Ser Ser Glu
                370                 375                 380
        Ala Cys Tyr Val Thr Gly Ile Thr Leu Phe Ala Asp Gly Gly Met Thr
        385                 390                 395                 400
        Gln Tyr Pro Ser Phe Gln Ala Gly Arg Gly
                        405                 410

<210> SEQ ID NO 12
<211> LENGTH: 1233
<212> TYPE: DNA
<213> ORGANISM: Artificial Sequence
<220> FEATURE:
<223> OTHER INFORMATION: omp-gdh (mutant; S16A, E170K, P194T, A197K,
      E222D, S237C) fusion
<220> FEATURE:
<221> NAME/KEY: variation
<222> LOCATION: (1)..(1230)

<400> SEQUENCE: 12
```

```
atgaaagcta ctaaactggt actgggtgcc gtcatcctgg gctcaacgct gctggcgggc      60
tgctcgtcaa atgcgaaaat cgatcaaggt atcaatccgt atgtcggctt tgaaatgggc     120
tatgattggc tgggtcgtat gccgtacaaa ggcagcgttg aaaacggtgc ctataaagca     180
cagggcgtcc aactgaccgc gaaactgggt tatccgatta ccgatgacct ggatatctac     240
acgcgtctgg gcggtatggt gtggcgtgca gacaccaaaa gtaacgttta cggcaaaaat     300
catgatacgg tgtttccccc ggtctttgcc ggcggtgtgg aatatgcaat taccccggaa     360
atcgctacgc gtctggaata ccagtggacc aacaatattg gcgacgcaca taccatcggt     420
acgcgcccgg ataatggcat tccgggtatg tataaagacc tggaaggcaa agtggttgtc     480
attactggta gcgctacggg cctgggtaaa gcgatggcca tccgttttgc taccgaaaaa     540
gcgaaagtgg ttgtcaacta ccgctcaaaa gaagaagaag cgaacagcgt gctggaagaa     600
atcaaaaaag ttggcggtga agcaatcgct gtcaaaggcg acgttacggt cgaaagcgat     660
gttattaacc tggtccagag ttccatcaaa gaatttggca aactggatgt catgattaac     720
aatgcgggta tggaaaatcc ggtgtcatcg catgaaatgt cactgtcgga ctggaacaaa     780
gtgattgata ccaatctgac gggcgctttt ctgggttcac gtgaagccat caaatacttc     840
gttgaaaacg atatcaaagg caccgtcatc aatatgagct ctgtgcatga aaaatcccg      900
tggccgctgt ttgtgcacta tgcggccagc aaaggcggta tgaaactgat gaccaaaacg     960
ctggccctgg aatacgcacc gaaaggtatt cgtgtgaaca atatcggccc gggtgcgatt    1020
aacaccacga tcaataaaga aaaattcgcg gacccggaac agcgcgccga tgttgaaagt    1080
atgattccga tgggctatat cggtgaaccg gacgaaattg cagctgttgc ggcctggctg    1140
gccagttccg aagcatgcta tgtcaccggc atcacgctgt ttgccgatgg cggtatgacc    1200
cagtaccccga gcttccaagc aggtcgcggc tga                               1233
```

<210> SEQ ID NO 13
<211> LENGTH: 291
<212> TYPE: PRT
<213> ORGANISM: Candida magnoliae
<220> FEATURE:
<221> NAME/KEY: VARIANT
<222> LOCATION: (1)..(283)
<223> OTHER INFORMATION: crs (wild type)

<400> SEQUENCE: 13

Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Val Asp Val Asp Leu

```
                130             135             140
Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro Leu Glu His His His
        275                 280                 285

His His His
    290

<210> SEQ ID NO 14
<211> LENGTH: 876
<212> TYPE: DNA
<213> ORGANISM: Candida magnoliae
<220> FEATURE:
<221> NAME/KEY: variation
<222> LOCATION: (1)..(849)
<223> OTHER INFORMATION: crs (wild type)

<400> SEQUENCE: 14
atggcgaaaa acttctctaa tgtggaatat ccggcaccgc cgccggcaca caccaaaaac      60
gaaagcctgc aagtgctgga tctgtttaaa ctgaatggca agttgcgtc tattacgggt     120 agctctagtg gcatcggtta tgcgctggcc gaagcattcg ctcaagttgg cgctgacgtc    180
gcgatttggt acaacagcca cgatgcgacc ggcaaagcgg aagcgctggc gaaaaaatat    240
ggtgttaaag tcaaagccta caaagcaaat gtctcctcat cggatgccgt gaaacagacc    300
attgaacagc aaatcaaaga ctttggccat ctggatattg tggttgctaa cgcgggcatc    360
ccgtggacga agggtgcgta tattgaccag gatgacgata acacttcga tcaagtcgtg    420 gacgtggatc tgaaaggcgt gggttacgtt gctaaacatg cgggtcgtca ctttcgtgaa    480
cgcttcgaaa agaaggcaa aaaaggtgcc ctggttttta ccgcatcaat gtcgggccat    540
atcgtgaacg ttccgcagtt ccaagccacg tataatgcgg ccaaagcagg tgtccgtcac    600
tttgctaaaa gtctggcggt ggaatttgcc ccgttcgcac gcgtcaacag cgtgtctccg    660
ggctacatca acaccgaaat ctcagatttc gttccgcagg aaacgcaaaa taatggtgg    720 tcgctggtcc cgctgggtcg cggcggtgaa accgctgaac tggttggtgc gtatctgttc    780
ctggcttcag acgcaggctc gtacgcgacc ggtacggaca ttatcgtgga tggcggttat    840
acgctgccgc tcgagcacca ccaccaccac cactga                              876

<210> SEQ ID NO 15
<211> LENGTH: 291
<212> TYPE: PRT
<213> ORGANISM: Candida magnoliae
```

<220> FEATURE:
<221> NAME/KEY: VARIANT
<222> LOCATION: (1)..(283)
<223> OTHER INFORMATION: crs (mutant; P14A, S42N, A194V, I275V)

<400> SEQUENCE: 15

```
Met Ala Lys Asn Phe Ser Asn Val Glu Tyr Pro Ala Pro Ala Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Asn Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Asp Val Asp Leu
    130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Val Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Val Val Asp Gly Gly Tyr Thr Leu Pro Leu Glu His His His
        275                 280                 285

His His His
    290
```

<210> SEQ ID NO 16
<211> LENGTH: 876
<212> TYPE: DNA
<213> ORGANISM: Candida magnoliae
<220> FEATURE:
<221> NAME/KEY: variation
<222> LOCATION: (1)..(849)
<223> OTHER INFORMATION: crs (mutant; P14A, S42N, A194V, I275V)

<400> SEQUENCE: 16

```
atggcgaaaa acttctctaa tgtggaatat ccagcaccgg cgccggcaca caccaaaaac    60
gaaagcctgc aagtgctgga tctgtttaaa ctgaatggca agttgcgtc tatcacgggt   120
```

-continued

```
agcaatagtg gtatcggtta tgcgctggcc gaagcattcg ctcaagttgg cgctgacgtc      180
gcgatttggt acaacagcca cgatgcgacc ggcaaagcgg aagcgctggc gaaaaaatat      240
ggtgttaaag tcaaagccta caaagcaaat gtctcctcat cggatgccgt gaaacagacc      300
attgaacagc aaatcaaaga ctttggccat ctggatattg tggttgctaa cgcgggcatc      360
ccgtggacga agggtgcgta tattgaccag gatgacgata acacttcga tcaagtcgtg      420 gacgtggatc tgaaaggcgt gggttacgtt gctaaacatg cgggtcgtca ctttcgtgaa      480
cgcttcgaaa agaaggcaa aaaaggtgcc ctggttttta ccgcatcaat gtcgggccat      540
atcgtgaacg ttccgcagtt ccaagccacg tataacgcag tcaaagcagg tgtccgtcac      600
tttgctaaaa gtctggcggt ggaatttgcc ccgttcgcac gcgtcaacag cgtgtctccg      660
ggctacatca acaccgaaat ctcagatttc gttccgcagg aaacgcaaaa taatggtgg      720 tcgctggtcc cgctgggtcg cggcggtgaa accgctgaac tggttggtgc gtatctgttc      780
ctggcttcag acgcaggctc gtacgcgacc ggtacggaca ttgtcgtgga tggcggttat      840
acgctgccgc tcgagcacca ccaccaccac cactga                                876
```

<210> SEQ ID NO 17
<211> LENGTH: 291
<212> TYPE: PRT
<213> ORGANISM: Candida magnoliae
<220> FEATURE:
<221> NAME/KEY: VARIANT
<222> LOCATION: (1)..(283)
<223> OTHER INFORMATION: crs (mutant; P14A, S42N, V147A, A194V, E234G)

<400> SEQUENCE: 17

```
Met Ala Lys Asn Phe Ser Asn Val Glu Tyr Pro Ala Pro Ala Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Asn Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80

Gly Val Lys Val Lys Ala Tyr Lys Ala Asn Val Ser Ser Ser Asp Ala
                85                  90                  95

Val Lys Gln Thr Ile Glu Gln Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Val Asp Val Asp Leu
    130                 135                 140

Lys Gly Ala Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Val Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
```

```
Thr Glu Ile Ser Asp Phe Val Pro Gln Glu Thr Gln Asn Arg Trp Trp
225                 230                 235                 240

Ser Leu Val Pro Leu Gly Arg Gly Gly Glu Thr Ala Glu Leu Val Gly
                245                 250                 255

Ala Tyr Leu Phe Leu Ala Ser Asp Ala Gly Ser Tyr Ala Thr Gly Thr
                260                 265                 270

Asp Ile Ile Val Asp Gly Gly Tyr Thr Leu Pro Leu Glu His His His
            275                 280                 285

His His His
        290

<210> SEQ ID NO 18
<211> LENGTH: 876
<212> TYPE: DNA
<213> ORGANISM: Candida magnoliae
<220> FEATURE:
<221> NAME/KEY: variation
<222> LOCATION: (1)..(849)
<223> OTHER INFORMATION: crs (mutant; P14A, S42N, V147A, A194V, E234G)

<400> SEQUENCE: 18
atggcgaaaa acttctctaa tgtggaatat ccagcaccgg cgccggcaca caccaaaaac     60
gaaagcctgc aagtgctgga tctgtttaaa ctgaatggca agttgcgtc tatcacgggt    120 agcaatagtg gtatcggtta tgcgctggcc gaagcattcg ctcaagttgg cgctgacgtc    180
gcgatttggt acaacagcca cgatgcgacc ggcaaagcgg aagcgctggc gaaaaaatat    240
ggtgttaaag tcaaagccta caaagcaaat gtctcctcat cggatgccgt gaaacagacc    300
attgaacagc aaatcaaaga cttggccat ctggatattg tggttgctaa cgcgggcatc    360
ccgtggacga agggtgcgta tattgaccag gatgacgata aacacttcga tcaagtcgtg    420
gacgtggatc tgaaaggcgc gggttacgtt gctaaacatg cgggtcgtca ctttcgtgaa    480
cgcttcgaaa agaaggcaa aaaaggtgcc ctggttttta ccgcatcaat gtcgggccat    540
atcgtgaacg ttccgcagtt ccaagccacg tataacgcag tcaaagcagg tgtccgtcac    600
tttgctaaaa gtctggcggt ggaatttgcc ccgttcgcac gcgtcaacag cgtgtctccg    660
ggctacatca acaccgaaat ctcagatttc gttccgcagg aaacgcaaaa tagatggtgg    720
tcgctggtcc cgctgggtcg cggcggtgaa accgctgaac tggttggtgc gtatctgttc    780
ctggcttcag acgcaggctc gtacgcgacc ggtacggaca ttatcgtgga tggcggttat    840
acgctgccgc tcgagcacca ccaccaccac cactga                              876

<210> SEQ ID NO 19
<211> LENGTH: 291
<212> TYPE: PRT
<213> ORGANISM: Candida magnoliae
<220> FEATURE:
<221> NAME/KEY: VARIANT
<222> LOCATION: (1)..(283)
<223> OTHER INFORMATION: crs (mutant; P14A, N20S, S42N, T190A, A194V,
      E234G)

<400> SEQUENCE: 19

Met Ala Lys Asn Phe Ser Asn Val Gly Tyr Pro Ala Pro Ala Pro Ala
1               5                   10                  15

His Thr Lys Ser Glu Ser Leu Gln Val Leu Asp Leu Phe Lys Leu Asn
                20                  25                  30

Gly Lys Val Ala Ser Ile Thr Gly Ser Asn Ser Gly Ile Gly Tyr Ala
```

```
                35                  40                  45
Leu Ala Glu Ala Phe Ala Gln Val Gly Ala Asp Val Ala Ile Trp Tyr
 50                  55                  60
Asn Ser His Asp Ala Thr Gly Lys Ala Glu Ala Leu Ala Lys Lys Tyr
 65                  70                  75                  80
Gly Val Lys Val Lys Ala Tyr Lys Ala Asn Val Ser Ser Ser Asp Ala
                 85                  90                  95
Val Lys Gln Thr Ile Glu Gln Gln Ile Lys Asp Phe Gly His Leu Asp
                100                 105                 110
Ile Val Val Ala Asn Ala Gly Ile Pro Trp Thr Lys Gly Ala Tyr Ile
                115                 120                 125
Asp Gln Asp Asp Asp Lys His Phe Asp Gln Val Val Asp Val Asp Leu
130                 135                 140
Lys Gly Val Gly Tyr Val Ala Lys His Ala Gly Arg His Phe Arg Glu
145                 150                 155                 160
Arg Phe Glu Lys Glu Gly Lys Lys Gly Ala Leu Val Phe Thr Ala Ser
                165                 170                 175
Met Ser Gly His Ile Val Asn Val Pro Gln Phe Gln Ala Ala Tyr Asn
                180                 185                 190
Ala Val Lys Ala Gly Val Arg His Phe Ala Lys Ser Leu Ala Val Glu
                195                 200                 205
Phe Ala Pro Phe Ala Arg Val Asn Ser Val Ser Pro Gly Tyr Ile Asn
210                 215                 220
Thr Glu Ile Ser Asp Phe Val Pro Gln Gly Thr Gln Asn Lys Trp Trp
225                 230                 235                 240
Ser Leu Val Pro Leu Gly Arg Gly Gly Glu Thr Ala Glu Leu Val Gly
                245                 250                 255
Ala Tyr Leu Phe Leu Ala Ser Asp Ala Gly Ser Tyr Ala Thr Gly Thr
                260                 265                 270
Asp Ile Ile Val Asp Gly Gly Tyr Thr Leu Pro Leu Glu His His His
                275                 280                 285
His His His
    290

<210> SEQ ID NO 20
<211> LENGTH: 876
<212> TYPE: DNA
<213> ORGANISM: Candida magnoliae
<220> FEATURE:
<221> NAME/KEY: variation
<222> LOCATION: (1)..(849)
<223> OTHER INFORMATION: crs (mutant; P14A, N20S, S42N, T190A, A194V,
      E234G)

<400> SEQUENCE: 20
atggctaaaa actttttccaa tgtcggatat cctgccccgg cgccagctca taccaaaagc      60
gaatcactgc aggtactgga tctgttcaaa ctgaacggca agtcgcgtc tatcaccggt     120 agcaactcag gcattggtta cgcgctggcc gaggcttttg cgcaggttgg cgcagacgtt     180
gcgatctggt ataacagcca tgatgccacc ggtaaagcag aggccctggc taaaaaatat     240
ggcgtaaaag tcaaggctta taagctaat gtcagttcga gtgatgcggt gaaacagact     300
attgagcagc agatcaagga ttttggccac ctggacatag ttgtggcgaa cgcaggcatc     360
ccctggacta gggtgcata catcgatcag gatgacgata acattttttga ccaggtggtt     420 gacgtcgacc tgaaaggcgt aggctatgta gcaaaacatg cgggtcgcca tttttcgtgaa     480
```

```
cgtttcgaaa aagaaggcaa aagggcgcc ttggtcttta cggcttccat gtcgggtcac    540
atcgttaacg tgccgcaatt tcaggcggcc tacaatgcgg tcaaggcagg cgtgcgtcat    600
ttcgcaaagt ccctggccgt ggaatttgct cctttcgcac gtgttaactc tgtatctcct    660
ggctatatta ataccgagat ctctgatttc gtcccgcaag gaacacagaa taaatggtgg    720
agcttagttc cattgggccg tgcggggaa actgcggaat tagttggtgc ctacctgttc    780
ctggcaagtg atgcgggctc ctacgccacg ggcacggata tcattgtgga cggcggctac    840
acgctgccgc tcgagcacca ccaccaccac cactga                              876
```

<210> SEQ ID NO 21
<211> LENGTH: 269
<212> TYPE: PRT
<213> ORGANISM: Bacillus megaterium
<220> FEATURE:
<221> NAME/KEY: VARIANT
<222> LOCATION: (1)..(261)
<223> OTHER INFORMATION: gdh (wild type)

<400> SEQUENCE: 21

```
Met Tyr Lys Asp Leu Glu Gly Lys Val Val Ile Thr Gly Ser Ser
1               5                  10                  15

Thr Gly Leu Gly Lys Ala Met Ala Ile Arg Phe Ala Thr Glu Lys Ala
            20                  25                  30

Lys Val Val Val Asn Tyr Arg Ser Lys Glu Glu Glu Ala Asn Ser Val
        35                  40                  45

Leu Glu Glu Ile Lys Lys Val Gly Gly Glu Ala Ile Ala Val Lys Gly
    50                  55                  60

Asp Val Thr Val Glu Ser Asp Val Ile Asn Leu Val Gln Ser Ser Ile
65                  70                  75                  80

Lys Glu Phe Gly Lys Leu Asp Val Met Ile Asn Asn Ala Gly Met Glu
                85                  90                  95

Asn Pro Val Ser Ser His Glu Met Ser Leu Ser Asp Trp Asn Lys Val
            100                 105                 110

Ile Asp Thr Asn Leu Thr Gly Ala Phe Leu Gly Ser Arg Glu Ala Ile
        115                 120                 125

Lys Tyr Phe Val Glu Asn Asp Ile Lys Gly Thr Val Ile Asn Met Ser
    130                 135                 140

Ser Val His Glu Lys Ile Pro Trp Pro Leu Phe Val His Tyr Ala Ala
145                 150                 155                 160

Ser Lys Gly Gly Met Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Glu Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Ser Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly Leu Glu His His His His His His
            260                 265
```

<210> SEQ ID NO 22

```
<211> LENGTH: 810
<212> TYPE: DNA
<213> ORGANISM: Bacillus megaterium
<220> FEATURE:
<221> NAME/KEY: variation
<222> LOCATION: (1)..(783)
<223> OTHER INFORMATION: gdh (wild type)

<400> SEQUENCE: 22
atgtataaag acctggaagg caaagtggtt gtcattaccg gtagctctac gggcctgggt     60
aaagcgatgg ccatccgttt tgctaccgaa aaagcgaaag tggttgtcaa ctaccgctca    120
aaagaagaag aagcgaacag cgtgctggaa gaaatcaaaa agttggcgg tgaagcaatc     180
gctgtcaaag cgacgttac ggtcgaaagc gatgttatta acctggtcca gagttccatc    240
aaagaatttg gcaaactgga tgtcatgatt aacaatgcgg gtatggaaaa tccggtgtca    300
tcgcatgaaa tgtcactgtc ggactggaac aaagtgattg ataccaatct gacgggcgct    360
tttctgggtt cacgtgaagc catcaaatac ttcgttgaaa acgatatcaa aggcaccgtc    420
atcaatatga gctctgtgca tgaaaaaatc ccgtggccgc tgtttgtgca ctatgcggcc    480
agcaaaggcg gtatgaaact gatgaccgaa acgctggccc tggaatacgc accgaaaggt    540
attcgtgtga caatatcgg cccgggtgcg attaacaccc cgatcaatgc tgaaaaattc    600
gcggacccgg aacagcgcgc cgatgttgaa agtatgattc cgatgggcta tcggtgaa     660
ccggaagaaa ttgcagctgt tgcggcctgg ctggccagtt ccgaagcatc ctatgtcacc    720
ggcatcacgc tgtttgccga tggcggtatg acccagtacc cgagcttcca agcaggtcgc    780
ggcctcgagc accaccacca ccaccactga                                     810

<210> SEQ ID NO 23
<211> LENGTH: 269
<212> TYPE: PRT
<213> ORGANISM: Bacillus megaterium
<220> FEATURE:
<221> NAME/KEY: VARIANT
<222> LOCATION: (1)..(263)
<223> OTHER INFORMATION: gdh (mutant; S16A, E170K, P194T, A197K, E222D,
      S237C)

<400> SEQUENCE: 23

Met Tyr Lys Asp Leu Glu Gly Lys Val Val Ile Thr Gly Ser Ala
1               5                   10                  15

Thr Gly Leu Gly Lys Ala Met Ala Ile Arg Phe Ala Thr Glu Lys Ala
                20                  25                  30

Lys Val Val Val Asn Tyr Arg Ser Lys Glu Glu Glu Ala Asn Ser Val
            35                  40                  45

Leu Glu Glu Ile Lys Lys Val Gly Gly Glu Ala Ile Ala Val Lys Gly
        50                  55                  60

Asp Val Thr Val Glu Ser Asp Val Ile Asn Leu Val Gln Ser Ser Ile
65                  70                  75                  80

Lys Glu Phe Gly Lys Leu Asp Val Met Ile Asn Asn Ala Gly Met Glu
                85                  90                  95

Asn Pro Val Ser Ser His Glu Met Ser Leu Ser Asp Trp Asn Lys Val
            100                 105                 110

Ile Asp Thr Asn Leu Thr Gly Ala Phe Leu Gly Ser Arg Glu Ala Ile
        115                 120                 125

Lys Tyr Phe Val Glu Asn Asp Ile Lys Gly Thr Val Ile Asn Met Ser
    130                 135                 140

Ser Val His Glu Lys Ile Pro Trp Pro Leu Phe Val His Tyr Ala Ala
```

```
145                 150                 155                 160
Ser Lys Gly Gly Met Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Thr Ile Asn Lys Glu Lys Phe Ala Asp Pro Glu Gln Arg Ala Asp
            195                 200                 205

Val Glu Ser Met Ile Pro Met Gly Tyr Ile Gly Glu Pro Asp Glu Ile
        210                 215                 220

Ala Ala Val Ala Ala Trp Leu Ala Ser Ser Glu Ala Cys Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly Leu Glu His His His His His His
                260                 265
```

<210> SEQ ID NO 24
<211> LENGTH: 810
<212> TYPE: DNA
<213> ORGANISM: Bacillus megaterium
<220> FEATURE:
<221> NAME/KEY: variation
<222> LOCATION: (1)..(783)
<223> OTHER INFORMATION: gdh (mutant; S16A, E170K, P194T, A197K, E222D, S237C)

<400> SEQUENCE: 24

```
atgtataaag acctggaagg caaagtggtt gtcattactg gtagcgctac gggcctgggt      60
aaagcgatgg ccatccgttt tgctaccgaa aaagcgaaag tggttgtcaa ctaccgctca     120
aaagaagaag aagcgaacag cgtgctggaa gaaatcaaaa agttggcgg tgaagcaatc     180
gctgtcaaag gcgacgttac ggtcgaaagc gatgttatta acctggtcca gagttccatc     240
aaagaatttg gcaaactgga tgtcatgatt aacaatgcgg gtatgaaaa tccggtgtca     300
tcgcatgaaa tgtcactgtc ggactggaac aaagtgattg ataccaatct gacgggcgct     360
tttctgggtt cacgtgaagc catcaaatac ttcgttgaaa acgatatcaa aggcaccgtc     420
atcaatatga gctctgtgca tgaaaaaatc ccgtggccgc tgtttgtgca ctatgcggcc     480
agcaaaggcg gtatgaaact gatgaccaaa acgctggccc tggaatacgc accgaaaggt     540
attcgtgtga acaatatcgg cccgggtgcg attaacacca cgatcaataa agaaaaattc     600
gcggacccgg aacagcgcgc cgatgttgaa agtatgattc cgatgggcta tatcggtgaa     660
ccggacgaaa ttgcagctgt tgcggcctgg ctggccagtt ccgaagcatg ctatgtcacc     720
ggcatcacgc tgtttgccga tggcggtatg acccagtacc cgagcttcca agcaggtcgc     780
ggcctcgagc accaccacca ccaccactga                                      810
```

<210> SEQ ID NO 25
<211> LENGTH: 37
<212> TYPE: DNA
<213> ORGANISM: Artificial Sequence
<220> FEATURE:
<223> OTHER INFORMATION: crs1F
<220> FEATURE:
<221> NAME/KEY: primer_bind
<222> LOCATION: (1)..(37)

<400> SEQUENCE: 25

```
aattgcgagc atatggcgaa aaacttctct aatgtgg                               37
```

```
<210> SEQ ID NO 26
<211> LENGTH: 30
<212> TYPE: DNA
<213> ORGANISM: Artificial Sequence
<220> FEATURE:
<223> OTHER INFORMATION: crs1R
<220> FEATURE:
<221> NAME/KEY: primer_bind
<222> LOCATION: (1)..(30)

<400> SEQUENCE: 26
cagtactaac tcgagcggca gcgtataacc                                      30

<210> SEQ ID NO 27
<211> LENGTH: 36
<212> TYPE: DNA
<213> ORGANISM: Artificial Sequence
<220> FEATURE:
<223> OTHER INFORMATION: oc1F
<220> FEATURE:
<221> NAME/KEY: primer_bind
<222> LOCATION: (1)..(36)

<400> SEQUENCE: 27
tatcgcattc catgggcaaa gctactaaac tggtac                               36

<210> SEQ ID NO 28
<211> LENGTH: 33
<212> TYPE: DNA
<213> ORGANISM: Artificial Sequence
<220> FEATURE:
<223> OTHER INFORMATION: oc1R
<220> FEATURE:
<221> NAME/KEY: primer_bind
<222> LOCATION: (1)..(33)

<400> SEQUENCE: 28
gttatgttca agcttttacg gcagggtata acc                                  33

<210> SEQ ID NO 29
<211> LENGTH: 31
<212> TYPE: DNA
<213> ORGANISM: Artificial Sequence
<220> FEATURE:
<223> OTHER INFORMATION: ogF
<220> FEATURE:
<221> NAME/KEY: primer_bind
<222> LOCATION: (1)..(31)

<400> SEQUENCE: 29
ggattgatgc atatgaaagc tacgaaactg g                                    31

<210> SEQ ID NO 30
<211> LENGTH: 34
<212> TYPE: DNA
<213> ORGANISM: Artificial Sequence
<220> FEATURE:
<223> OTHER INFORMATION: ogR
<220> FEATURE:
<221> NAME/KEY: primer_bind
<222> LOCATION: (1)..(34)

<400> SEQUENCE: 30
atattctagc tcgagttaac cgcggcctgc ttgg                                 34

<210> SEQ ID NO 31
<211> LENGTH: 32
<212> TYPE: DNA
```

```
<213> ORGANISM: Artificial Sequence
<220> FEATURE:
<223> OTHER INFORMATION: gdhF
<220> FEATURE:
<221> NAME/KEY: primer_bind
<222> LOCATION: (1)..(32)

<400> SEQUENCE: 31
acgcgtgcac atatgtataa agacctggaa gg                              32

<210> SEQ ID NO 32
<211> LENGTH: 31
<212> TYPE: DNA
<213> ORGANISM: Artificial Sequence
<220> FEATURE:
<223> OTHER INFORMATION: gdhR
<220> FEATURE:
<221> NAME/KEY: primer_bind
<222> LOCATION: (1)..(31)

<400> SEQUENCE: 32
atgtagtatc tcgaggccgc tacctgcttg g                               31
```